(12) United States Patent
Mochizuki et al.

(10) Patent No.: US 9,765,369 B2
(45) Date of Patent: Sep. 19, 2017

(54) METHOD FOR PRODUCING 1,5-PENTAMETHYLENEDIAMINE, MUTANT LYSINE DECARBOXYLASE, METHOD FOR PRODUCING 1,5-PENTAMETHYLENE DIISOCYANATE AND METHOD FOR PRODUCING POLYISOCYANATE COMPOSITION

(71) Applicant: MITSUI CHEMICALS, INC., Tokyo (JP)

(72) Inventors: Daisuke Mochizuki, Mobara (JP); Tadashi Araki, Chiba (JP); Akiko Natsuji, Mobara (JP); Tomomi Sakai, Tokyo (JP); Tomonori Hidesaki, Singapore (SG)

(73) Assignee: MITSUI CHEMICALS, INC., Tokyo (JP)

( * ) Notice: Subject to any disclaimer, the term of this patent is extended or adjusted under 35 U.S.C. 154(b) by 38 days.

(21) Appl. No.: 14/372,386

(22) PCT Filed: Jan. 17, 2013

(86) PCT No.: PCT/JP2013/050862
§ 371 (c)(1),
(2) Date: Jul. 15, 2014

(87) PCT Pub. No.: WO2013/108859
PCT Pub. Date: Jul. 25, 2013

(65) Prior Publication Data
US 2015/0132808 A1 May 14, 2015

(30) Foreign Application Priority Data

Jan. 18, 2012 (JP) .................................. 2012-008173

(51) Int. Cl.
*C12P 13/00* (2006.01)
*C12N 9/88* (2006.01)
*C07C 209/68* (2006.01)
*C07C 263/10* (2006.01)

(52) U.S. Cl.
CPC .......... *C12P 13/001* (2013.01); *C07C 209/68* (2013.01); *C07C 263/10* (2013.01); *C12N 9/88* (2013.01); *C12P 13/00* (2013.01); *C12Y 401/01018* (2013.01)

(58) Field of Classification Search
None
See application file for complete search history.

(56) References Cited

U.S. PATENT DOCUMENTS 8,758,764 B2 * 6/2014 Masignani ......... A61K 39/0258
424/185.1
2013/0079486 A1 3/2013 Hidesaki et al.

FOREIGN PATENT DOCUMENTS

| EP | 2 543 736 A1 | 1/2013 |
| JP | 2002-223770 A | 8/2002 |
| JP | 2004-000114 A | 1/2004 |
| JP | 2004-208646 A | 7/2004 |
| JP | 2009-207495 A | 9/2009 |
| JP | 2011-201863 A | 10/2011 |
| WO | WO 2011/108473 A1 | 9/2011 |
| WO | WO-2013/108860 A1 | 7/2013 |

OTHER PUBLICATIONS

Parkhill et al. (Nature, vol. 413, Oct. 2001, pp. 848-852).*
International Preliminary Report on Patentability received in corresponding application No. PCT/JP2013/050862 mailed Jul. 31, 2014 (with English translation).
International Search Report dated Apr. 16, 2013 issued in Application No. PCT/JP2013/050862.
Meng, et al., "Nucleotide Sequence of the *Escherichia coli* cad Operon: a System for Neutralization of Low Extracellular pH," J. Bacteriol., 1992, vol. 174, No. 8, p. 2659-2669.
Qian, et al., "Metabolic Engineering of *Escherichia coli* for the Production of Cadaverine: A Five Carbon Diamine," Biotechnol. Bioeng., 2011, vol. 108, No. 1, p. 93-103.
Sabo, et al., "Purification and Physical Properties of Inducible *Escherichia coli* Lysine Decarboxylase," Biochemistry, 1974, vol. 13, No. 4, p. 662-670.
Takatsuka et al., "Gene Cloning and Molecular Characterization of Lysine Decarboxylase from Selenomonas ruminantium Delineate Its Evolutionary Relationship to Ornithine Decarboxylases from Eukaryotes," J. Bacteriol., 2000, vol. 182, No. 23, P. 6732-6741.
Takatsuka et al., "Novel Characteristics of *Selenomonas ruminantium* Lysine Decarboxylase Capable of Decarboxylating Both L-Lysine and L-Ornithine," Biosci. Biotechnol. Biochem., 1999, 63 (6), p. 1063-1069.
Takatsuka, et al., "Identification of the Amino Acid Residues Conferring Substrate Specificity upon *Selenomonas ruminantium* Lysine Decarboxylase," Biosci. Biotechnol. Biochem., 1999, 63 (10), p. 1843-1846.
Iwanami's Biological Dictionary, 4th Edition, R. Yasugi et al. (ed.), Iwanami Shoten, Publishers, p. 1151 (Mar. 21, 1996).
Notification of Reasons for Refusal issued on Jun. 16, 2015 in Japanese Patent Application No. 2013-554351.
Hans Leemhuis et al., "Directed Evolution of Enzymes: Library Screening Strategies", IUBMB Life, 61 (3), pp. 222-228, Mar. 2009.
Supplementary Partial European Search Report issued in European Patent Application No. 13738315.4 dated Sep. 28, 2015.
M. Lemonnier et al., "Expression of the second lysine decarboxylase gene of *Escherichia coli*", Microbiology, vol. 144, No. 3, Mar. 1, 1998, pp. 751-760.
Kikuchi Yoshimi et al., "Characterization of a second lysine decarboxylase isolated from *Escherichia coli*", Microbiology, vol. 179, No. 14, Jul. 1, 1997, pp. 4486-4492.
Usheer Kanjee et al., Linkage between the bacterial acid stress and stringent responses: the structure of the inducible lysine decarboxylase, The Embo Journal, vol. 30, No. 5, Mar. 2, 2011, pp. 931-944.

* cited by examiner

*Primary Examiner* — Hope Robinson
(74) *Attorney, Agent, or Firm* — Foley & Lardner LLP

(57) ABSTRACT

A mutant lysine decarboxylase produced by replacing at least one of the amino acids in SEQ ID NO:4 with another amino acid.

5 Claims, 2 Drawing Sheets

METHOD FOR PRODUCING 1,5-PENTAMETHYLENEDIAMINE, MUTANT LYSINE DECARBOXYLASE, METHOD FOR PRODUCING 1,5-PENTAMETHYLENE DIISOCYANATE AND METHOD FOR PRODUCING POLYISOCYANATE COMPOSITION

CROSS-REFERENCE TO RELATED PATENT APPLICATIONS

This application is the National Phase of PCT/JP2013/050862, filed Jan. 17, 2013, which claims priority to Japanese Application No. 2012-008173, filed Jan. 18, 2012.

TECHNICAL FIELD

The present invention relates to a method for producing 1,5-pentamethylenediamine, mutant lysine decarboxylase, a method for producing 1,5-pentamethylene diisocyanate, and a method for producing a polyisocyanate composition.

BACKGROUND ART

The mutant lysine decarboxylase according to [4] or [5], wherein at least one or more of the following replacement 1,5-Pentamethylenediamine is diamine known to be produced by decarboxylation of lysine, i.e., amino acid, and recently, has been gaining attention as biomass-derived polymer materials and intermediates for agricultural chemicals and pharmaceutical products.

As a method for producing 1,5-pentamethylenediamine, for example, a method described in patent document 1 below is known. In this method, amino acid lysine is allowed to react with *Escherichia coli*-derived lysine decarboxylase for the production.

Although the document describes that the enzyme amount to be used is not restricted, an appropriate amount of necessary enzyme is, in the case of purified enzyme, 25 mg/L to 70 mg/L, and in the case of catalyst resting bacterial cell, 5 g/L to 15 g/L of enzyme. Furthermore, Examples show that 0.97M of 1,5-pentamethylenediamine is produced from 1M of lysine neutralized with adipic acid by using 50 mg/L of purified enzyme with reaction at 45° C. and for 48 hours. However, generally, production of purified enzyme involves a large amount of costs, and therefore preferably, catalyst resting bacterial cell is used as a catalyst for polymer material production. Also, the document shows that 6.6 g/L of 1,5-pentamethylenediamine is produced from a fermentation liquid containing 10 g/L of lysine using 50 mg/L of purified enzyme and performing reaction at 45° C. for 24 hours.

Furthermore, according to Sabo et al., purified *Escherichia coli*-derived lysine decarboxylase has a specific activity of, per 1 mg of enzyme, 900 to 1100 µmol/min (for example, non-patent document 1 below).

Furthermore, TAKATSUKA et al. shows, with the specific activity of *Selenomonas ruminantium*-derived lysine decarboxylase, per 1 kg of enzyme, 0.198 mol of 1,5-pentamethylenediamine is produced for one second (for example, non-patent document 2 below).

This is an activity producing 11.88 µmol of 1,5-pentamethylenediamine per 1 mg of enzyme for one minute, and activity of lysine decarboxylase per enzyme is, relative to the *Escherichia coli*-derived one, about 1/100.

Furthermore, a method in which improvement in activity by modification of *Selenomonas ruminantium*-derived lysine decarboxylase gene is known (for example, see non-patent document 3 below).

Non-patent document 3 shows that changes in amino acids at two positions achieve an increase in Kcat at a rate of 1.3 times.

CITATION LIST

Patent Document

Patent Document 1
Japanese Unexamined Patent Publication No. 2009-207495

Non-Patent Document

Non-patent document 1: Sabo, D. L. et al., Biochemistry 13 (1974) pp. 662-670.
Non-patent document 2: TAKATSUKA et al., Bioscience, Biotechnology, and Biochemistry Vol. 63 (1999), No. 6 pp. 1063-1069
Non-patent document 3: TAKATSUKA et al., Bioscience, Biotechnology, and Biochemistry Vol. 63 (1999), No. 10 pp. 1843-1846

SUMMARY OF THE INVENTION

Problem to be Solved by the Invention

For low-cost production of 1,5-pentamethylenediamine, it is obvious that production of a 1,5-pentamethylenediamine accumulated amount with a higher concentration should be achieved in a short period of time with a smaller amount of enzyme, or catalyst resting bacterial cell, or treated substance thereof. However, it has been found that when the purified enzyme, or a catalyst resting bacterial cell amount, or a treated amount is decreased in reaction that produces 1,5-pentamethylenediamine from lysine, reaction does not advance even if the reaction time is extended.

That is, the present invention aims to solve the phenomenon that a small amount of purified enzyme, catalyst resting bacterial cell, or catalyst inactivated bacterial cell hinders the advancement of reaction, and to provide a method for producing a high concentration 1,5-pentamethylenediamine for a short period of time.

Furthermore, the present invention also aims to provide a catalyst that realizes a 1,5-pentamethylenediamine accumulated amount with a higher concentration for a short period of time with a smaller amount of enzyme, or catalyst resting bacterial cell, or treated substance thereof, and to provide a method for producing a high concentration 1,5-pentamethylenediamine for a short period of time using the catalyst.

Furthermore, the present invention also aims to provide a method for producing 1,5-pentamethylene diisocyanate and a polyisocyanate composition efficiently.

Means for Solving the Problem

To solve the above-described problems, the present inventors diligently conducted researches in a method for producing 1,5-pentamethylenediamine, and as a result, found that by producing 1,5-pentamethylenediamine with a reaction solution containing a substance that prevents deactivation of lysine decarboxylation when L-lysine decarboxylase acts on an aqueous solution of L-lysine, 1,5-pentamethylenediamine can be produced efficiently.

Furthermore, the present inventors diligently conducted researches, and found out mutant lysine decarboxylase, or bacterial cell that expresses such enzyme that significantly and efficiently produces 1,5-pentamethylenediamine by introducing a mutation into a specific portion of lysine decarboxylase. Furthermore, the present inventors found out industrially advantageous production of 1,5-pentamethylenediamine with the use of the lysine decarboxylase.

That is, the present invention relates to the following:

[1] A mutant lysine decarboxylase, wherein in the amino acid sequence shown in SEQ ID NO: 4 of the sequence listing, at least one of the amino acids in the amino acid sequence is replaced with another amino acid that allows for increase in activity;

[2] The mutant lysine decarboxylase of [1], wherein the amino acid to be replaced with another amino acid is present in a decamer forming domain and/or an activation region domain;

[3] The mutant lysine decarboxylase of [2], wherein the decamer forming domain is a wing domain and/or a linker domain, and the activation region domain is a pyridoxal phosphate enzyme co-domain and/or a substrate entrance/exit;

[4] The mutant lysine decarboxylase according to [2] or [3], wherein in the amino acid sequence shown in SEQ ID NO: 4 of the sequence listing, the amino acid present in the decamer forming domain includes at least one of amino acids at positions 14, 28, 39, 64, 67, 70, 75, 79, 83, 84, 85, 88, 89, 94, 95, 98, 99, 104, 112, 119, 137, 138, 139, 143, 145, 148, and 182, and the amino acid present in the activation region domain includes at least one of amino acids at positions 184, 253, 262, 286, 290, 295, 303, 317, 335, 352, 353, 386, 430, 443, 446, 460, 466, 471, 475, 506, 524, 539, 544, 546, 553, 623, 626, 636, 646, 648, and 711;

[5] The mutant lysine decarboxylase of [3] or [4], wherein in the amino acid sequence shown in SEQ ID NO: 4 of the sequence listing, the amino acid present in the wing domain includes at least one of amino acids at positions 14, 28, 39, 64, 67, 70, 75, 79, 83, 84, 85, 88, 89, 94, 95, 98, 99, 104, 112, and 119, the amino acid present in the linker domain includes at least one of amino acids at positions 137, 138, 139, 143, 145, 148, and 182, the amino acid present in the pyridoxal phosphate enzyme co-domain includes at least one of amino acids at positions 184, 253, 262, 286, 290, 295, 303, 317, 335, 352, 353, and 386, and the amino acid present in the substrate entrance/exit includes at least one of amino acids at positions 430, 443, 446, 460, 466, 471, 475, 506, 524, 539, 544, 546, 553, 623, 626, 636, 646, 648, and 711;

[6] The mutant lysine decarboxylase according to [4] or [5], wherein at least one or more of the following replacement is performed in the amino acid sequence shown in SEQ ID NO: 4 of the sequence listing:

of the amino acids present in the decamer forming domain, amino acid at position 14 is changed from Phe to Gln, amino acid at position 28 is changed from Arg to Ile, amino acid at position 39 is changed from Arg to Ile, amino acid at position 39 is changed from Arg to Val, amino acid at position 64 is changed from Leu to Lys, amino acid at position 67 is changed from Cys to Thr, amino acid at position 67 is changed from Cys to Leu, amino acid at position 70 is changed from Ile to Leu, amino acid at position 70 is changed from Ile to Pro, amino acid at position 75 is changed from Glu to Pro, amino acid at position 75 is changed from Glu to His, amino acid at position 79 is changed from Leu to Ile, amino acid at position 83 is changed from Ala to Leu, amino acid at position 83 is changed from Ala to Ile, amino acid at position 84 is changed from Asn to Asp, amino acid at position 84 is changed from Asn to Thr, amino acid at position 85 is changed from Thr to Pro, amino acid at position 88 is changed from Thr to Lys, amino acid at position 88 is changed from Thr to Arg, amino acid at position 88 is changed from Thr to Asn, amino acid at position 89 is changed from Leu to Phe, amino acid at position 94 is changed from Asn to Ile, amino acid at position 95 is changed from Asp to Pro, amino acid at position 98 is changed from Leu to Ile, amino acid at position 99 is changed from Gln to Thr, amino acid at position 104 is changed from Glu to Asn, amino acid at position 104 is changed from Glu to Lys, amino acid at position 112 is changed from Asp to Glu, amino acid at position 119 is changed from Gln to Asn, amino acid at position 119 is changed from Gln to Ile, amino acid at position 119 is changed from Gln to Thr, amino acid at position 119 is changed from Gln to Ser, amino acid at position 137 is changed from Phe to Val, amino acid at position 138 is changed from Lys to Ile, amino acid at position 139 is changed from Tyr to Val, amino acid at position 139 is changed from Tyr to Cys, amino acid at position 139 is changed from Tyr to Thr, amino acid at position 139 is changed from Tyr to Ser, amino acid at position 143 is changed from Tyr to Asn, amino acid at position 145 is changed from Gly to Glu, amino acid at position 148 is changed from Tyr to Arg, amino acid at position 148 is changed from Cys to Ser, amino acid at position 148 is changed from Cys to Ala, and amino acid at position 182 is changed from Ile to Met;

of the amino acids present in the activation region domain, amino acid at position 184 is changed from Val to Ala, amino acid at position 253 is changed from Met to Leu, amino acid at position 262 is changed from Phe to Tyr, amino acid at position 286 is changed from Ala to Asp, amino acid at position 290 is changed from Lys to His, amino acid at position 295 is changed from Ala to Ser, amino acid at position 303 is changed from Ile to Thr, amino acid at position 317 is changed from Phe to Gln, amino acid at position 335 is changed from Pro to Ala, amino acid at position 352 is changed from Gly to Ala, amino acid at position 353 is changed from Arg to His, amino acid at position 386 is changed from Glu to Ser, amino acid at position 430 is changed from Glu to Phe, amino acid at position 443 is changed from Arg to Met, amino acid at position 446 is changed from Ser to Tyr, amino acid at position 446 is changed from Ser to Gln, amino acid at position 460 is changed from Asp to Ile, amino acid at position 460 is changed from Asp to Asn, amino acid at position 460 is changed from Asp to Cys, amino acid at position 460 is changed from Asp to Gln, amino acid at position 460 is changed from Asp to Pro, amino acid at position 460 is changed from Asp to Ser, amino acid at position 466 is changed from Pro to Asn, amino acid at position 466 is changed from Pro to Gly, amino acid at position 466 is changed from Pro to Ser, amino acid at position 471 is changed from Ser to Tyr, amino acid at position 475 is changed from Gly to Asn, amino acid at position 506 is changed from Asp to Pro, amino acid at position 524 is changed from Val to Leu, amino acid at position 524 is changed from Val to Leu, amino acid at position 539 is changed from Ile to Cys, amino acid at position 539 is changed from Ile to Leu, amino acid at position 544 is changed from Thr to Ala, amino acid at position 544 is changed from Thr to Ser, amino acid at position 544 is changed from Thr to Pro, amino acid at position 546 is changed from Ala to Ser, amino acid at position 553 is changed from Leu to Val, amino acid at position 623 is changed from Ala to Cys, amino acid at position 623 is changed from Ala to Phe, amino acid at position 623 is changed from Ala to Gln, amino acid at position 626 is changed from Lys to Val, amino acid at position 636 is changed from Tyr to Cys, amino acid at position 636 is changed from Tyr to Pro, amino acid at position 646 is changed from Ala to Leu, amino acid at position 646 is changed from Ala to Ile, amino acid at position 648 is changed from Met to Ser, amino acid at position 710 is changed from Lys to Thr, and amino acid at position 711 is changed from Glu to Asp;

[7] The mutant lysine decarboxylase of [5] or [6], wherein at least one or more of the following replacement is performed in the amino acid sequence shown in SEQ ID NO: 4 of the sequence listing:

of the amino acids present in the wing domain, amino acid at position 14 is changed from Phe to Gln, amino acid at position 28 is changed from Arg to Ile, amino acid at position 39 is changed from Arg to Ile, amino acid at position 39 is changed from Arg to Val, amino acid at position 64 is changed from Leu to Lys, amino acid at position 67 is changed from Cys to Thr, amino acid at position 67 is changed from Cys to Leu, amino acid at position 70 is changed from Ile to Leu, amino acid at position 70 is changed from Ile to Pro, amino acid at position 75 is changed from Glu to Pro, amino acid at position 75 is changed from Glu to His, amino acid at position 79 is changed from Leu to Ile, amino acid at position 83 is changed from Ala to Leu, amino acid at position 83 is changed from Ala to Ile, amino acid at position 84 is changed from Asn to Asp, amino acid at position 84 is changed from Asn to Thr, amino acid at position 85 is changed from Thr to Pro, amino acid at position 88 is changed from Thr to Lys, amino acid at position 88 is changed from Thr to Arg, amino acid at position 88 is changed from Thr to Asn, amino acid at position 89 is changed from Leu to Phe, amino acid at position 94 is changed from Asn to Ile, amino acid at position 95 is changed from Asp to Pro, amino acid at position 98 is changed from Leu to Ile, amino acid at position 99 is changed from Gln to Thr, amino acid at position 104 is changed from Glu to Asn, amino acid at position 104 is changed from Glu to Lys, amino acid at position 112 is changed from Asp to Glu, amino acid at position 119 is changed from Gln to Asn, amino acid at position 119 is changed from Gln to Ile, amino acid at position 119 is changed from Gln to Thr, and amino acid at position 119 is changed from Gln to Ser, of the amino acids present in the linker domain, amino acid at position 137 is changed from Phe to Val, amino acid at position 138 is changed from Lys to Ile, amino acid at position 139 is changed from Tyr to Val, amino acid at position 139 is changed from Tyr to Cys, amino acid at position 139 is changed from Tyr to Thr, amino acid at position 139 is changed from Tyr to Ser, amino acid at position 139 is changed from Tyr to Asn, amino acid at position 143 is changed from Gly to Glu, amino acid at position 145 is changed from Tyr to Arg, amino acid at position 148 is changed from Cys to Ser, and amino acid at position 148 is changed from Cys to Ala, and amino acid at position 182 is changed from Ile to Met, of the amino acids present in the pyridoxal phosphate enzyme co-domain, amino acid at position 184 is changed from Val to Ala, amino acid at position 253 is changed from Met to Leu, amino acid at position 262 is changed from Phe to Tyr, amino acid at position 286 is changed from Ala to Asp, amino acid at position 290 is changed from Lys to His, amino acid at position 295 is changed from Ala to Ser, amino acid at position 303 is changed from Ile to Thr, amino acid at position 317 is changed from Phe to Gln, amino acid at position 335 is changed from Pro to Ala, amino acid at position 352 is changed from Gly to Ala, amino acid at position 353 is changed from Arg to His, and amino acid at position 386 is changed from Glu to Ser, and of the amino acids present in the substrate entrance/exit, amino acid at position 430 is changed from Glu to Phe, amino acid at position 443 is changed from Arg to Met, amino acid at position 446 is changed from Ser to Tyr, amino acid at position 446 is changed from Ser to Gln, amino acid at position 460 is changed from Asp to Ile, amino acid at position 460 is changed from Asp to Asn, amino acid at position 460 is changed from Asp to Cys, amino acid at position 460 is changed from Asp to Gln, amino acid at position 460 is changed from Asp to Pro, amino acid at position 460 is changed from Asp to Ser, amino acid at position 466 is changed from Pro to Asn, amino acid at position 466 is changed from Pro to Gly, amino acid at position 466 is changed from Pro to Ser, amino acid at position 471 is changed from Ser to Tyr, amino acid at position 475 is changed from Gly to Asn, amino acid at position 506 is changed from Asp to Pro, amino acid at position 524 is changed from Val to Leu, amino acid at position 524 is changed from Val to Leu, amino acid at position 539 is changed from Ile to Cys, amino acid at position 539 is changed from Ile to Leu, amino acid at position 544 is changed from Thr to Ala, amino acid at position 544 is changed from Thr to Ser, amino acid at position 544 is changed from Thr to Pro, amino acid at position 546 is changed from Ala to Ser, amino acid at position 553 is changed from Leu to Val, amino acid at position 623 is changed from Ala to Cys, amino acid at position 623 is changed from Ala to Phe, amino acid at position 623 is changed from Ala to Gln, amino acid at position 626 is changed from Lys to Val, amino acid at position 636 is changed from Tyr to Cys, amino acid at position 636 is changed from Tyr to Pro, amino acid at position 646 is changed from Ala to Leu, amino acid at position 646 is changed from Ala to Ile, amino acid at position 648 is changed from Met to Ser, amino acid at position 710 is changed from Lys to Thr, and amino acid at position 711 is changed from Glu to Asp;

[8] The mutant lysine decarboxylase in accordance with any of [1] to [7], wherein in the amino acid sequence shown in SEQ ID NO: 4 of the sequence listing, amino acids at positions 290, 335, 475, and 711 are replaced with other amino acids;

[9] The mutant lysine decarboxylase in accordance with any of [1] to [7], wherein in the amino acid sequence shown in SEQ ID NO: 4 of the sequence listing, the amino acids at positions 286, 290, 335, 475, and 711 are replaced with other amino acids;

[10] The mutant lysine decarboxylase in accordance with any of [1] to [7], wherein in the amino acid sequence shown in SEQ ID NO: 4 of the sequence listing, the amino acids at positions 148 and 646 are replaced with other amino acids;

[11] The mutant lysine decarboxylase in accordance with any of [1] to [7], wherein in the amino acid sequence shown in SEQ ID NO: 4 of the sequence listing, the amino acids at positions 471 and 626 are replaced with other amino acids;

[12] The mutant lysine decarboxylase in accordance with any of [1] to [7], wherein in the amino acid sequence shown in SEQ ID NO: 4 of the sequence listing, the amino acids at positions 626 and 646 are replaced with other amino acids;

[13] A method for producing 1,5-pentamethylenediamine, the method comprising subjecting L-lysine and/or its salt to lysine decarboxylation with a mutant lysine decarboxylase in the presence of a substance that prevents deceleration or stoppage of lysine decarboxylation, wherein in the mutant lysine decarboxylase, at least one of the amino acids in the amino acid sequence shown in SEQ ID NO: 4 of the sequence listing is replaced with another amino acid;

[14] The method for producing 1,5-pentamethylenediamine in accordance with [13], wherein 5 units to 165 units per 1 g of lysine of the mutant lysine decarboxylase are used, or 5 μg to 165 μg per 1 g of lysine on the purified enzyme basis of the mutant lysine decarboxylase is used;

[15] The method for producing 1,5-pentamethylenediamine in accordance with [13] or [14], wherein the substance that prevents deceleration or stoppage of lysine decarboxylation is a microorganism fermentation liquid, a treated microorganism fermentation liquid, or a component contained therein;

[16] The method for producing 1,5-pentamethylenediamine in accordance with any of [13] to [15], wherein the substance that prevents deceleration or stoppage of lysine decarboxylation is a component contained in the fermentation liquid at the time of lysine production, or in a treated fermentation liquid at the time of lysine production;

[17] The method for producing 1,5-pentamethylenediamine in accordance with any of [13] to [16], wherein the substance that prevents deceleration or stoppage of lysine decarboxylation is a component contained in a culture solution in which microorganism is cultured;

[18] The method for producing 1,5-pentamethylenediamine in accordance with any of [13] to [17], wherein the substance that prevents deceleration or stoppage of lysine decarboxylation is a microorganism or a treated microorganism;

[19] The method for producing 1,5-pentamethylenediamine in accordance with [17] or [18], wherein the microorganism is procaryotes and/or eucaryotes;

[20] The method for producing 1,5-pentamethylenediamine in accordance with any of [17] to [19], wherein the microorganism is lysine-producing bacteria;

[21] The method for producing 1,5-pentamethylenediamine in accordance with any of [13] to [17], wherein the substance that prevents deceleration or stoppage of lysine decarboxylation is a compound that can be a carbon source of the microorganism;

[22] The method for producing 1,5-pentamethylenediamine in accordance with [21], wherein the compound that can be a carbon source of the microorganism is at least one selected from the group consisting of corn steep liquor, blackstrap molasses, saccharides, and amino acids;

[23] The method for producing 1,5-pentamethylenediamine in accordance with any of [13] to [17], wherein the substance that prevents deceleration or stoppage of reaction is a mixture of the microorganism and the compound that can be a carbon source of the microorganism;

[24] A method for producing 1,5-pentamethylene diisocyanate, including isocyanization of 1,5-pentamethylenediamine or its salt obtained by the method in any of [13] to [23];

[25] A method for producing a polyisocyanate composition, the method including: modifying 1,5-pentamethylene diisocyanate obtained by the method of [24] so that the 1,5-pentamethylene diisocyanate contains at least one functional group of (a) to (e) below,
(a) an isocyanurate group,
(b) an allophanate group,
(c) a biuret group,
(d) a urethane group, and
(e) a urea group.

Effects of the Invention

The present invention provides a method of producing a high-concentration 1,5-pentamethylenediamine for a short period of time: the method of the present invention solves the phenomenon of not advancing reaction when the amount of purified enzyme, catalyst resting bacterial cell, or catalyst inactivated bacterial cell is smaller than before, improves the reaction velocity, and furthermore, the present invention allows for efficient production of 1,5-pentamethylene diisocyanate and a polyisocyanate composition by using such 1,5-pentamethylenediamine.

EMBODIMENT OF THE INVENTION

Figure 1:
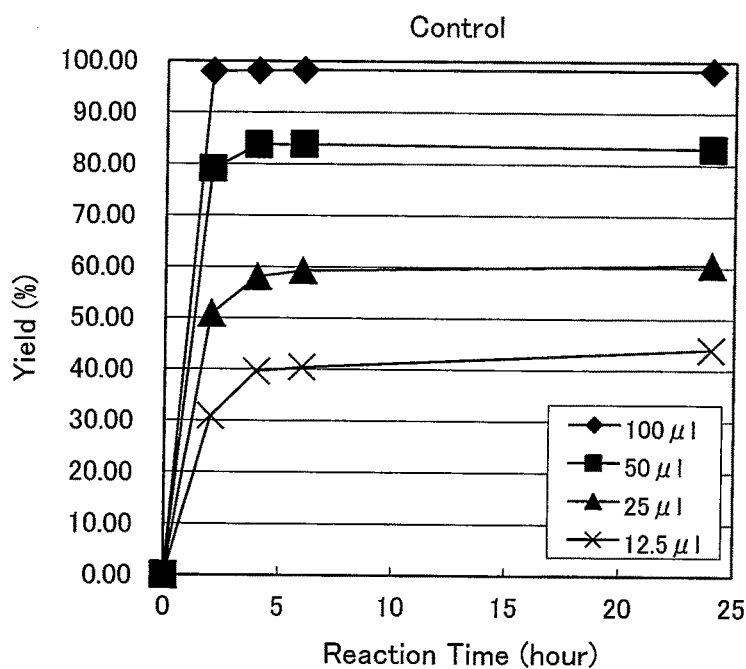
FIG. 1 is a graph illustrating reaction efficiency of lysine decarboxylation in ion-exchange water.

The present invention is described in detail below.
(1) Lysine Decarboxylase
Lysine decarboxylase in the present invention is an enzyme that is classified in enzyme number EC4.1.1.18 of Enzyme Nomenclature Committee of International Union of Biochemistry (I.U.B.), requires pyridoxal phosphate (PLP) as coenzyme, and catalyzes reaction that produces 1,5-pentamethylenediamine (also noted as pentane 1,5-diamine and 1,5-pentamethylenediamine) and carbon dioxide from L-lysine (also noted as lysine); a bacterial cell that highly produces this enzyme with a technique such as genetic recombination; and treated substances thereof. Lysine decarboxylase of the present invention is derived, without particular limitation, for example, from known organisms. Examples of lysine decarboxylase include, to be more specific, those derived from microorganisms including *Bacillus halodurans*, *Bacillus subtilis*, *Escherichia coli*, *Vibrio cholerae*, *Vibrio parahaemolyticus*, *Streptomyces coelicolor*, *Streptomyces pilosus*, *Eikenella corrodens*, *Eubacterium acidaminophilum*, *Salmonella typhimurium*, *Hafnia alvei*, *Neisseria meningitidis*, *Thermoplasma acidophilum*, *Pyrococcus abyssi*, and *Corynebacterium glutamicum*. In view of safety, preferably, lysine decarboxylase derived from *Escherichia coli* is used.

The gene to be expressed is not particularly limited as long as similar effects can be exhibited, but *Escherichia coli*-derived cadA (GenBank Accession No. AP009048) is suitable.
(2) Lysine Decarboxylase Activity
In the present invention, lysine decarboxylase activity means activity of catalyzing the reaction of lysine decarboxylation and conversion to 1,5-pentamethylenediamine.

In the present invention, the activity can be calculated by determining the amount of 1,5-pentamethylenediamine produced from lysine with a high-performance liquid chromatography (HPLC).

The unit of activity is as follows: the activity of producing 1 μmol of 1,5-pentamethylenediamine for 1 minute is regarded as 1 unit (U), and bacterial cell activity is shown with enzyme activity (U/mg dry cells) per 1 mg of dry bacterial cell-based weight. The dry bacterial cell-based weight of the bacterial cell is the weight of bacterial cells that are dry and do not contain moisture. The dry bacterial cell-based weight of bacterial cells can be obtained, for example, by separating bacterial cells from a liquid containing bacterial cells (bacterial cell liquid) by a method such as centrifugal separation or filtration, drying the bacterial cells until the weight is a constant weight, and measuring the weight. The measurement can be performed in accordance with the method by Sabo et al.

(3) Substance that Prevents Deceleration or Stoppage of Reaction

The substance that prevents deceleration or stoppage of reaction of the present invention is a substance in the reaction solution excluding L-lysine, PLP, lysine decarboxylase, water, inorganic acids that are used for adjusting pH, bases, and dicarboxylic acids; and is a substance that has effects of preventing the phenomenon of quick drop or stoppage of reaction velocity of lysine decarboxylation when L-lysine decarboxylase acts on aqueous solution of L-lysine: in other words, a substance that accelerates lysine decarboxylation in the reaction system. Examples include a culture solution in which a microorganism is cultured, a microorganism, a carbon source that can be used by the microorganism, and a lysine fermentation liquid.

That is, as is described later, when lysine is produced by fermenting glucose using cultured microorganism, the fermentation liquid (lysine fermentation liquid) at the time of lysine production contains a culture solution in which a microorganism is cultured, and the culture solution contains a microorganism and a carbon source that can be used by the microorganism.

The bacterial cell in the present invention is categorized into several types. To avoid misunderstanding, in the present invention, the bacterial cell of the present invention is defined as follows. "Catalyst bacterial cell" is defined as a bacterial cell that produces lysine decarboxylase with high productivity, and has a higher lysine decarboxylation activity than that of wild strain. Furthermore, living catalyst bacterial cells are named as "catalyst living bacterial cell", catalyst bacterial cells that are in stoppage of growth is named as "catalyst resting bacterial cell", and catalyst bacterial cells that are incapable of growth are named "catalyst inactivated bacterial cell". The bacterial cell that produces 10 g/L or more of lysine from glucose in the culture solution is named "lysine-producing bacteria".

The "microorganism" in the present invention is general bacterial cell other than the catalyst bacterial cell, and the lysine-producing bacteria is regarded as included in the microorganism. The type of the microorganism is not particularly limited, and suitable examples include yeast, *Corynebacterium*, *Brevibacterium*, and *Escherichia coli*. *Corynebacterium* is particularly highly effective. The suitable concentration changes in accordance with the composition of the reaction solution, but for example, when the reaction solution is composed of only water, PLP, enzyme, and lysine hydrochloride, and in the case of *Escherichia coli*, a viable cell count of $1 \times 10^8$/ml or more is a suitable concentration. In the case of yeast, a viable cell count of $1 \times 10^7$/ml or more is a suitable concentration. In the case of *Corynebacterium*, a viable cell count of $1 \times 10^6$/ml or more is a suitable concentration. The upper limit is not particularly limited, as long as lysine as substrate is dissolved and the reaction solution has flowability, but generally, based on bacterial cell wet weight, 500 g/L or less. Furthermore, when an additive that can be a carbon source for the microorganism is present in the reaction solution, the microorganism concentration can be reduced. For example, when 0.5 g/L of molasses or corn steep liquor (CSL) is mixed, in the case of *Corynebacterium*, a viable cell count of $1 \times 10^3$/ml or more is a suitable concentration. Furthermore, when the reaction solution contains centrifugal separation supernatant of the fermentation liquid, or the reaction solution is the centrifugal separation supernatant of the fermentation liquid itself, 50/ml or more is a suitable concentration. However, when the fermentation liquid is used, it is effective to perform reaction while lysine-producing bacteria remains before centrifugal separation, and then remove catalyst bacterial cell along with the lysine-producing bacteria by, for example, centrifugal separation after the completion of the reaction. Furthermore, the reaction can be started before completion of lysine fermentation.

The treated microorganism in the present invention refers to, for example, the microorganism in resting state and starts growing when in growable condition, such as dry yeast, alcohol fermentation starter, and cryopreserved bacterial cell.

The compound that can be a carbon source of a microorganism of the present invention is not particularly limited, as long as the carbon source can be used for microorganism growth. Suitable examples include corn steep liquor, yeast extracts, molasses, saccharides, polypeptones, and amino acids. Corn steep liquor and yeast extracts are particularly effective. Suitable concentrations are as follows: in the case of yeast extracts and corn steep liquor, 1 g/L or more, in the case of polypeptone, 5 g/L or more, and in the case of molasses, 10 g/L or more are effective. When these are mixed with *Corynebacterium*, the concentration can be further low to bring out effects, for example, when *Corynebacterium* of a viable cell count of $1 \times 10^3$/ml or more is mixed, they can bring out effects with 0.5 g/L.

The fermentation liquid at lysine production of the present invention is a liquid in which culture is performed for a predetermined time period after planting lysine-producing bacteria in a culture solution, and contains 10 g/L or more of lysine and lysine-producing bacteria.

The treated fermentation liquid at the time of lysine production in the present invention refers to a concentrated or diluted fermentation liquid at the time of lysine production; a fermentation liquid supernatant in which lysine-producing bacteria is removed by centrifugal separation from the fermentation liquid at the time of lysine production; its concentrate; and its dilution.

When the fermentation liquid or treated liquid thereof at the time of lysine production in the present invention is added to a reaction solution, at least 5 vol %, preferably 20 vol %, even more preferably 50 vol % or more of the reaction solution is added.

The medium used in the fermentation liquid at the time of lysine production in the present invention is a general medium containing a carbon source, a nitrogen source, inorganic ion, and as necessary, other organic micronutrient. Examples of carbon sources include carbohydrates such as glucose, lactose, galactose, fructose, sucrose, blackstrap molasses, and starch hydrolysate; alcohols such as ethanol and inositol; and organic acids such as acetic acid, fumaric acid, citric acid, and succinic acid. Examples of nitrogen sources include inorganic ammonium salts such as ammonium sulfate, ammonium nitrate, ammonium chloride, ammonium phosphate, and ammonium acetate; organic nitrogen such as ammonia, peptone, meat extracts, yeast extracts, yeast extracts, corn steep liquor, and soybean hydrolysate; ammonia gas; and ammonia water. As inorganic ion, for example, potassium phosphate, magnesium sulfate, iron ion, and manganese ion are added in a small amount. As organic micronutrient, a required substance such as vitamin B1 or yeast extracts can be contained in a suitable amount as necessary. The culture is preferably performed under aerobic conditions by, for example, shaking culture, and aerated and agitated culture for 16 to 72 hours, and the culture temperature is controlled to 30° C. to 45° C., and pH during culture is set to 5 to 9. For the pH adjustment, an inorganic or organic, acidic or alkaline substance, and furthermore, for example, ammonia gas can be used.

The microorganism used for the fermentation liquid at the time of lysine production in the present invention may be a wild strain, or may be a constructed strain that is artificially bred from the wild strain as long as the microorganism is capable of producing L-lysine.

Examples include those microorganisms belonging to genus *Corynebacterium*, genus *Brevibacterium*, genus *Microbacterium*, and genus *Escherichia*. Those microorganisms belonging to genus *Corynebacterium*, genus *Brevibacterium*, and genus *Microbacterium* are preferable.

(4) Mutant Lysine Decarboxylase

Mutant lysine decarboxylase in the present invention is defined as a lysine decarboxylase having a mutation in which at least one amino acid is replaced with another amino acid in the amino acid sequence of a wild type lysine decarboxylase using mainly genetical modification technology, and having an improved enzyme activity of lysine decarboxylase itself. Mutant lysine decarboxylase is included in the range of the present invention.

The amino acids in the amino acid sequence correspond to the amino acid residue in the lysine decarboxylase, and they are in corresponding relation to each other. In the following, when amino acids are mentioned, they represent amino acids shown in the amino acid sequence, and when the amino acid residues are mentioned, they represent the amino acid residues contained in the lysine decarboxylase.

In the present invention, the method for preparing a mutant lysine decarboxylase gene may be any known method of introducing a mutation, and generally, a known method can be used. Examples of the methods include site-specific mutation method (Kramer, W. and frita, H. J., Methods in Enzymology, 1987, vol. 154, page 350), recombinant PCR method (PCR Technology, Stockton Press, 1989), a method in which nucleic acid at specific portion is chemically synthesized, a method in which gene is treated with hydroxyamine, and a method in which a strain having gene is subjected to ultraviolet ray irradiation, and a method in which treatment with chemical substance such as nitrosoguanidine and nitrous acid.

Of those methods for introducing a mutation, preferably, the site-specific mutation method is used. To be specific, a method is used in which site-specific replacement is caused based on a wild type lysine decarboxylase gene using a commercially available kit.

When amino acid residue is inserted, deleted, or replaced, the positions of the insertion, deletion, or replacement may be at any position as long as lysine decarboxylation activity is not lost. The number of the inserted, deleted, or replaced amino acid residues is one amino acid residue or two amino acid residues or more, and for example, one amino acid residue to ten amino acid residues, preferably, one amino acid residue to five amino acid residues.

In the present invention, in those descriptions relating to the sequences of amino acid sequence and base sequence that code for mutant lysine decarboxylase, or the sequence of primer, the matters mentioned based on the complementary relation of these also apply to the sequence complementary to the sequences and also to sequences complementary to the sequences unless otherwise noted. When the matters of the present invention is applied to the sequence complementary to the sequences, within the range of commonsense to those in the art, the whole description is interpreted as applied to the sequence complementary to the sequence described in the description.

To be specific, in the present invention, in the mutant lysine decarboxylase, at least one of the amino acids in the amino acid sequence is replaced with another amino acid that allows for increase in activity in the amino acid sequence shown in SEQ ID NO: 4 of the sequence listing.

The amino acid sequence shown in SEQ ID NO: 4 in the sequence listing is an amino acid sequence of protein produced by a DNA sequence shown in SEQ ID NO: 3 in the sequence listing, and setting methionine at N-terminal as the amino acid at position 1, amino acids at positions 1 to 129 correspond to a wing domain, and amino acids at positions 130 to 183 correspond to a linker domain, and those amino acids at positions 1 to 183 form a decamer forming domain. The amino acids at positions 184 to 417 correspond to a pyridoxal phosphate enzyme (PLP enzyme) co-domain, the amino acids at positions 418 to 715 correspond to a substrate entrance/exit, and those amino acids at positions 184 to 715 form an activation region domain.

In the mutant lysine decarboxylase in the present invention, in the amino acid sequence shown in SEQ ID NO: 4 of the sequence listing, the amino acid present in the decamer forming domain and/or activation region domain is replaced with other amino acids, and in particular, the amino acid present in the wing domain and/or the linker domain in the decamer forming domain and/or the amino acid present in the pyridoxal phosphate enzyme co-domain and/or the substrate entrance/exit in the activation region domain are replaced with other amino acid.

That is, in the mutant lysine decarboxylase, amino acid residue corresponding to the amino acid in the above-described amino acid sequence is replaced with another amino acid residue.

As the mutant lysine decarboxylase, preferably used is a mutant enzyme in which at least one or more of the amino acid residues at positions of 137, 138, 286, 290, 295, 303, 317, 335, 352, 353, 386, 443, 466, 475, 553, and 711; and the amino acid residues at positions of 14, 28, 39, 64, 67, 70, 75, 79, 83, 84, 85, 88, 89, 94, 95, 98, 99, 104, 112, 119, 139, 143, 145, 148, 182, 184, 253, 262, 430, 446, 460, 471, 506, 524, 539, 544, 546, 623, 626, 636, 646, and 648 are replaced with other amino acid residue.

The mutant enzyme in which at least one or more of the amino acid residues at positions of 137, 138, 286, 290, 295, 303, 317, 335, 352, 353, 386, 443, 466, 475, 553, and 711; and amino acid residues at positions 14, 28, 39, 64, 67, 70, 75, 79, 83, 84, 85, 88, 89, 94, 95, 98, 99, 104, 112, 119, 139, 143, 145, 148, 182, 184, 253, 262, 430, 446, 460, 471, 506, 524, 539, 544, 546, 623, 626, 636, 646, and 648 are replaced with other amino acid residues is, in the present invention, a mutant enzyme having a sequence in which setting the N-terminal methionine as amino acid at position 1 of the amino acid sequence (SEQ ID NO: 4 of sequence listing), of the protein produced from the DNA sequence shown in SEQ ID NO: 3 in the sequence listing, at least one or more of amino acids at positions 137, 138, 286, 290, 295, 303, 317, 335, 352, 353, 386, 443, 466, 475, 553, and 711; and amino acids at positions 14, 28, 39, 64, 67, 70, 75, 79, 83, 84, 85, 88, 89, 94, 95, 98, 99, 104, 112, 119, 139, 143, 145, 148, 182, 184, 253, 262, 430, 446, 460, 471, 506, 524, 539, 544, 546, 623, 626, 636, 646, and 648 are replaced with amino acids that are different from the original amino acids sequence. However, the one in which amino acid at position 89 is changed to arginine is excluded. There is no limitation as long as the amino acid sequence after the change has better characteristics than before the change, for example, improvement in specific activity, characteristics of resistance to pH changes during reaction, resistance to reaction product, and alleviation of inhibition. However, the amino acid sequence produced by the sequences shown in Tables 1 to 6 is particularly preferable.

Preferable mutant lysine decarboxylase is, to be more specific, mutant lysine decarboxylase in which at least one or more of the following replacement is performed in the amino acid sequence shown in SEQ ID NO: 4 of the sequence listing, of the amino acids present in the decamer forming domain, amino acid at position 14 is changed from Phe to Gln, amino acid at position 28 is changed from Arg to Ile, amino acid at position 39 is changed from Arg to Ile, amino acid at position 39 is changed from Arg to Val, amino acid at position 64 is changed from Leu to Lys, amino acid at position 67 is changed from Cys to Thr, amino acid at position 67 is changed from Cys to Leu, amino acid at position 70 is changed from Ile to Leu, amino acid at position 70 is changed from Ile to Pro, amino acid at position 75 is changed from Glu to Pro, amino acid at position 75 is changed from Glu to His, amino acid at position 79 is changed from Leu to Ile, amino acid at position 83 is changed from Ala to Leu, amino acid at position 83 is changed from Ala to Ile, amino acid at position 84 is changed from Asn to Asp, amino acid at position 84 is changed from Asn to Thr, amino acid at position 85 is changed from Thr to Pro, amino acid at position 88 is changed from Thr to Lys, amino acid at position 88 is changed from Thr to Arg, amino acid at position 88 is changed from Thr to Asn, amino acid at position 89 is changed from Leu to Phe, amino acid at position 94 is changed from Asn to Ile, amino acid at position 95 is changed from Asp to Pro, amino acid at position 98 is changed from Leu to Ile, amino acid at position 99 is changed from Gln to Thr, amino acid at position 104 is changed from Glu to Asn, amino acid at position 104 is changed from Glu to Lys, amino acid at position 112 is changed from Asp to Glu, amino acid at position 119 is changed from Gln to Asn, amino acid at position 119 is changed from Gln to Ile, amino acid at position 119 is changed from Gln to Thr, amino acid at position 119 is changed from Gln to Ser, amino acid at position 137 is changed from Phe to Val, amino acid at position 138 is changed from Lys to Ile, amino acid at position 139 is changed from Tyr to Val, amino acid at position 139 is changed from Tyr to Cys, amino acid at position 139 is changed from Tyr to Thr, amino acid at position 139 is changed from Tyr to Ser, amino acid at position 139 is changed from Tyr to Asn, amino acid at position 143 is changed from Gly to Glu, amino acid at position 145 is changed from Tyr to Arg, amino acid at position 148 is changed from Cys to Ser, amino acid at position 148 is changed from Cys to Ala, and amino acid at position 182 is changed from Ile to Met, and of the amino acids present in the activation region domain, amino acid at position 184 is changed from Val to Ala, amino acid at position 253 is changed from Met to Leu, amino acid at position 262 is changed from Phe to Tyr, amino acid at position 286 is changed from Ala to Asp, amino acid at position 290 is changed from Lys to His, amino acid at position 295 is changed from Ala to Ser, amino acid at position 303 is changed from Ile to Thr, amino acid at position 317 is changed from Phe to Gln, amino acid at position 335 is changed from Pro to Ala, amino acid at position 352 is changed from Gly to Ala, amino acid at position 353 is changed from Arg to His, amino acid at position 386 is changed from Glu to Ser, amino acid at position 430 is changed from Glu to Phe, amino acid at position 443 is changed from Arg to Met, amino acid at position 446 is changed from Ser to Tyr, amino acid at position 446 is changed from Ser to Gln, amino acid at position 460 is changed from Asp to Ile, amino acid at position 460 is changed from Asp to Asn, amino acid at position 460 is changed from Asp to Cys, amino acid at position 460 is changed from Asp to Gln, amino acid at position 460 is changed from Asp to Pro, amino acid at position 460 is changed from Asp to Ser, amino acid at position 466 is changed from Pro to Asn, amino acid at position 466 is changed from Pro to Gly, amino acid at position 466 is changed from Pro to Ser, amino acid at position 471 is changed from Ser to Tyr, amino acid at position 475 is changed from Gly to Asn, amino acid at position 506 is changed from Asp to Pro, amino acid at position 524 is changed from Val to Leu, amino acid at position 524 is changed from Val to Leu, amino acid at position 539 is changed from Ile to Cys, amino acid at position 539 is changed from Ile to Leu, amino acid at position 544 is changed from Thr to Ala, amino acid at position 544 is changed from Thr to Ser, amino acid at position 544 is changed from Thr to Pro, amino acid at position 546 is changed from Ala to Ser, amino acid at position 553 is changed from Leu to Val, amino acid at position 623 is changed from Ala to Cys, amino acid at position 623 is changed from Ala to Phe, amino acid at position 623 is changed from Ala to Gln, amino acid at position 626 is changed from Lys to Val, amino acid at position 636 is changed from Tyr to Cys, amino acid at position 636 is changed from Tyr to Pro, amino acid at position 646 is changed from Ala to Leu, amino acid at position 646 is changed from Ala to Ile, amino acid at position 648 is changed from Met to Ser, amino acid at position 710 is changed from Lys to Thr, and amino acid at position 711 is changed from Glu to Asp.

To be more specific, in the mutant lysine decarboxylase, at least one or more of the following replacement is performed in the amino acid sequence shown in SEQ ID NO: 4 of the sequence listing:

of the amino acids present in the wing domain, amino acid at position 14 is changed from Phe to Gln, amino acid at position 28 is changed from Arg to Ile, amino acid at position 39 is changed from Arg to Ile, amino acid at position 39 is changed from Arg to Val, amino acid at position 64 is changed from Leu to Lys, amino acid at position 67 is changed from Cys to Thr, amino acid at position 67 is changed from Cys to Leu, amino acid at position 70 is changed from Ile to Leu, amino acid at position 70 is changed from Ile to Pro, amino acid at position 75 is changed from Glu to Pro, amino acid at position 75 is changed from Glu to His, amino acid at position 79 is changed from Leu to Ile, amino acid at position 83 is changed from Ala to Leu, amino acid at position 83 is changed from Ala to Ile, amino acid at position 84 is changed from Asn to Asp, amino acid at position 84 is changed from Asn to Thr, amino acid at position 85 is changed from Thr to Pro, amino acid at position 88 is changed from Thr to Lys, amino acid at position 88 is changed from Thr to Arg, amino acid at position 88 is changed from Thr to Asn, amino acid at position 89 is changed from Leu to Phe, amino acid at position 94 is changed from Asn to Ile, amino acid at position 95 is changed from Asp to Pro, amino acid at position 98 is changed from Leu to Ile, amino acid at position 99 is changed from Gln to Thr, amino acid at position 104 is changed from Glu to Asn, amino acid at position 104 is changed from Glu to Lys, amino acid at position 112 is changed from Asp to Glu, amino acid at position 119 is changed from Gln to Asn, amino acid at position 119 is changed from Gln to Ile, amino acid at position 119 is changed from Gln to Thr, amino acid at position 119 is changed from Gln to Ser;

of the amino acids present in the linker domain, amino acid at position 137 is changed from Phe to Val, amino acid at position 138 is changed from Lys to Ile, amino acid at position 139 is changed from Tyr to Val, amino acid at position 139 is changed from Tyr to Cys, amino acid at position 139 is changed from Tyr to Thr, amino acid at position 139 is changed from Tyr to Ser, amino acid at position 139 is changed from Tyr to Asn, amino acid at position 143 is changed from Gly to Glu, amino acid at position 145 is changed from Tyr to Arg, amino acid at position 148 is changed from Cys to Ser, amino acid at position 148 is changed from Cys to Ala, amino acid at position 182 is changed from Ile to Met;

of the amino acids present in the pyridoxal phosphate enzyme co-domain, amino acid at position 184 is changed from Val to Ala, amino acid at position 253 is changed from Met to Leu, amino acid at position 262 is changed from Phe to Tyr, amino acid at position 286 is changed from Ala to Asp, amino acid at position 290 is changed from Lys to His, amino acid at position 295 is changed from Ala to Ser, amino acid at position 303 is changed from Ile to Thr, amino acid at position 317 is changed from Phe to Gln, amino acid at position 335 is changed from Pro to Ala, amino acid at position 352 is changed from Gly to Ala, amino acid at position 353 is changed from Arg to His, amino acid at position 386 is changed from Glu to Ser; and of the amino acids present in the substrate entrance/exit, amino acid at position 430 is changed from Glu to Phe, amino acid at position 443 is changed from Arg to Met, amino acid at position 446 is changed from Ser to Tyr, amino acid at position 446 is changed from Ser to Gln, amino acid at position 460 is changed from Asp to Ile, amino acid at position 460 is changed from Asp to Asn, amino acid at position 460 is changed from Asp to Cys, amino acid at position 460 is changed from Asp to Gln, amino acid at position 460 is changed from Asp to Pro, amino acid at position 460 is changed from Asp to Ser, amino acid at position 466 is changed from Pro to Asn, amino acid at position 466 is changed from Pro to Gly, amino acid at position 466 is changed from Pro to Ser, amino acid at position 471 is changed from Ser to Tyr, amino acid at position 475 is changed from Gly to Asn, amino acid at position 506 is changed from Asp to Pro, amino acid at position 524 is changed from Val to Leu, amino acid at position 524 is changed from Val to Leu, amino acid at position 539 is changed from Ile to Cys, amino acid at position 539 is changed from Ile to Leu, amino acid at position 544 is changed from Thr to Ala, amino acid at position 544 is changed from Thr to Ser, amino acid at position 544 is changed from Thr to Pro, amino acid at position 546 is changed from Ala to Ser, amino acid at position 553 is changed from Leu to Val, amino acid at position 623 is changed from Ala to Cys, amino acid at position 623 is changed from Ala to Phe, amino acid at position 623 is changed from Ala to Gln, amino acid at position 626 is changed from Lys to Val, amino acid at position 636 is changed from Tyr to Cys, amino acid at position 636 is changed from Tyr to Pro, amino acid at position 646 is changed from Ala to Leu, amino acid at position 646 is changed from Ala to Ile, amino acid at position 648 is changed from Met to Ser, amino acid at position 710 is changed from Lys to Thr, amino acid at position 711 is changed from Glu to Asp.

Preferable mutant lysine decarboxylase is a mutant enzyme in which, in the activation region domain, to be specific, amino acid residues at positions 290, 335, 475, and 711; amino acid residues at positions 286, 290, 335, 475, and 711; amino acid residues at positions 148 and 646; amino acid residues at positions 471 and 626; and amino acid residues at positions 626 and 646 are replaced with other amino acid residues.

The mutant enzyme in which the amino acid residues at positions 290, 335, 475, and 711 are replaced with other amino acid residues in the present invention refers to a mutant enzyme having a sequence in which four amino acids at positions 290, 335, 475, and 711 are replaced with amino acids that are different from the original amino acids, setting N-terminal methionine of the amino acid sequence of the protein produced from the DNA sequence shown in SEQ ID NO: 3 in the sequence listing as amino acid at position 1.

The mutant enzyme in which the amino acid residues at positions 286, 290, 335, 475, and 711 are replaced with other amino acid residues in the present invention refers to a mutant enzyme having a sequence in which five amino acids at positions 286, 290, 335, 475, and 711 are replaced with amino acids that are different from the original amino acids, setting the N-terminal methionine of the amino acid sequence of the protein produced from the DNA sequence shown in SEQ ID NO: 3 in the sequence listing as amino acid at position 1.

The mutant enzyme in which the amino acid residues at positions 148 and 646 are replaced with other amino acid residues in the present invention refers to a mutant enzyme having a sequence in which two amino acids at positions 148 and 646 are replaced with amino acids that are different from the original amino acids, setting the N-terminal methionine of the amino acid sequence of the protein produced from the DNA sequence shown in SEQ ID NO: 3 in the sequence listing as amino acid at position 1.

The mutant enzyme in which the amino acid residues at positions 471 and 626 are replaced with other amino acid residues in the present invention refers to a mutant enzyme having a sequence in which two amino acids at 471 and 626 are replaced with amino acids that are different from the original amino acids, setting the N-terminal methionine of the amino acid sequence of the protein produced from the DNA sequence shown in SEQ ID NO: 3 in the sequence listing as amino acid at position 1.

The mutant enzyme in which the amino acid residues at positions 626 and 646 are replaced with other amino acid residues in the present invention refers to a mutant enzyme having a sequence in which two amino acids at positions 626 and 646 are replaced with amino acids that are different from the original amino acids, setting the N-terminal methionine of the amino acid sequence of the protein produced from the DNA sequence shown in SEQ ID NO: 3 in the sequence listing as amino acid at position 1.

The amino acid sequence after the change is not particularly limited, as long as better characteristics than that of the enzyme in the original sequence are present. However, the amino acid sequences produced from the sequences of Tables 1 to 6 are particularly preferable.

In the description above, the changed mutant lysine decarboxylase is described as those in which amino acids in the amino acid sequence are changed. However, the changed mutant lysine decarboxylase can be shown as those in which the base sequence that codes for amino acids is changed.

Examples of such mutant lysine decarboxylase include mutant lysine decarboxylase in which at least one or more of the following replacement is performed in the amino acid sequence shown in SEQ ID NO: 3 of the sequence listing:

of the amino acids present in the decamer forming domain, the base sequence that codes for Phe of amino acid at position 14 is changed from TTT to CAA, the base sequence that codes for Gln, the base sequence that codes for Leu of amino acid at position 22 is changed from CTT to TTG, the base sequence that codes for Leu, the base sequence that codes for Arg of amino acid at position 28 is changed from CGT to ATT, the base sequence that codes for Ile, the base sequence that codes for Arg of amino acid at position 39 is changed from CGT to ATA, the base sequence that codes for Ile, the base sequence that codes for Arg of amino acid at position 39 is changed from CGT to ATC, the base sequence that codes for Ile, the base sequence that codes for Arg of amino acid at position 39 is changed from CGT to GTG, the base sequence that codes for Val, the base sequence that codes for Leu of amino acid at position 64 is changed from CTC to AAA, the base sequence that codes for Lys, the base sequence that codes for Cys of amino acid at position 67 is changed from TGC to ACC, the base sequence that codes for Thr, the base sequence that codes for Cys of amino acid at position 67 is changed from TGC to TTA, the base sequence that codes for Leu, the base sequence that codes for Ile of amino acid at position 70 is changed from ATT to TTG, the base sequence that codes for Leu, the base sequence that codes for Ile of amino acid at position 70 is changed from ATT to CTG, the base sequence that codes for Leu, the base sequence that codes for Ile of amino acid at position 70 is changed from ATT to CCG, the base sequence that codes for Pro, the base sequence that codes for Glu of amino acid at position 75 is changed from GAG to CCC, the base sequence that codes for Pro, the base sequence that codes for Glu of amino acid at position 75 is changed from GAG to CAC, the base sequence that codes for His, the base sequence that codes for Leu of amino acid at position 79 is changed from TTG to ATA, the base sequence that codes for Ile, the base sequence that codes for Ala of amino acid at position 83 is changed from GCT to CTG, the base sequence that codes for Leu, the base sequence that codes for Ala of amino acid at position 83 is changed from GCT to CTA, the base sequence that codes for Leu, the base sequence that codes for Ala of amino acid at position 83 is changed from GCT to CTT, the base sequence that codes for Leu, the base sequence that codes for Ala of amino acid at position 83 is changed from GCT to ATA, the base sequence that codes for Ile, the base sequence that codes for Ala of amino acid at position 83 is changed from GCT to GCC, the base sequence that codes for Ala, the base sequence that codes for Asn of amino acid at position 84 is changed from AAT to GAC, the base sequence that codes for Asp, the base sequence that codes for Asn of amino acid at position 84 is changed from AAT to ACA, the base sequence that codes for Thr, the base sequence that codes for Thr of amino acid at position 85 is changed from ACG to CCA, the base sequence that codes for Pro, the base sequence that codes for Thr of amino acid at position 88 is changed from ACT to AAA, the base sequence that codes for Lys, the base sequence that codes for Thr of amino acid at position 88 is changed from ACT to AAG, the base sequence that codes for Lys, the base sequence that codes for Thr of amino acid at position 88 is changed from ACT to AGA, the base sequence that codes for Arg, the base sequence that codes for Thr of amino acid at position 88 is changed from ACT to AAT, the base sequence that codes for Asn, the base sequence that codes for Leu of amino acid at position 89 is changed from CTC to TTT, the base sequence that codes for Phe, the base sequence that codes for Asn of amino acid at position 94 is changed from AAT to ATC, the base sequence that codes for Ile, the base sequence that codes for Asp of amino acid at position 95 is changed from GAC to CCG, the base sequence that codes for Pro, the base sequence that codes for Leu of amino acid at position 98 is changed from TTA to ATA, the base sequence that codes for Ile, the base sequence that codes for Gln of amino acid at position 99 is changed from CAG to ACT, the base sequence that codes for Thr, the base sequence that codes for Glu of amino acid at position 104 is changed from GAA to AAT, the base sequence that codes for Asn, the base sequence that codes for Glu of amino acid at position 104 is changed from GAA to AAA, the base sequence that codes for Lys, the base sequence that codes for Asp of amino acid at position 112 is changed from GAT to GAG, the base sequence that codes for Glu, the base sequence that codes for Gln of amino acid at position 119 is changed from CAG to AAC, the base sequence that codes for Asn, the base sequence that codes for Gln of amino acid at position 119 is changed from CAG to AAT, the base sequence that codes for Asn, the base sequence that codes for Gln of amino acid at position 119 is changed from CAG to ATT, the base sequence that codes for Ile, the base sequence that codes for Gln of amino acid at position 119 is changed from CAG to ACC, the base sequence that codes for Thr, the base sequence that codes for Gln of amino acid at position 119 is changed from CAG to AGT, the base sequence that codes for Ser, the base sequence that codes for Phe of amino acid at position 137 is changed from TTT to GTC, the base sequence that codes for Val, the base sequence that codes for Lys of amino acid at position 138 is changed from AAA to ATC, the base sequence that codes for Ile, the base sequence that codes for Tyr of amino acid at position 139 is changed from TAT to GTA, the base sequence that codes for Val, the base sequence that codes for Tyr of amino acid at position 139 is changed from TAT to GTG, the base sequence that codes for Val, the base sequence that codes for Tyr of amino acid at position 139 is changed from TAT to TGC, the base sequence that codes for Cys, the base sequence that codes for Tyr of amino acid at position 139 is changed from TAT to ACA, the base sequence that codes for Thr, the base sequence that codes for Tyr of amino acid at position 139 is changed from TAT to TCT, the base sequence that codes for Ser, the base sequence that codes for Tyr of amino acid at position 139 is changed from TAT to AGT, the base sequence that codes for Ser, the base sequence that codes for Tyr of amino acid at position 139 is changed from TAT to AAC, the base sequence that codes for Asn, the base sequence that codes for Gly of amino acid at position 143 is changed from GGT to GAA, the base sequence that codes for Glu, the base sequence that codes for Tyr of amino acid at position 145 is changed from TAT to CGT, the base sequence that codes for Arg, the base sequence that codes for Tyr of amino acid at position 145 is changed from TAT to AGA, the base sequence that codes for Arg, the base sequence that codes for Cys of amino acid at position 148 is changed from TGT to AGT, the base sequence that codes for Ser, the base sequence that codes for Cys of amino acid at position 148 is changed from TGT to TCT, the base sequence that codes for Ser, the base sequence that codes for Cys of amino acid at position 148 is changed from TGT to TCC, the base sequence that codes for Ser, the base sequence that codes for Cys of amino acid at position 148 is changed from TGT to TCA, the base sequence that codes for Ser, the base sequence that codes for Cys of amino acid at position 148 is changed from TGT to GCG, the base sequence that codes for Ala, the base sequence that codes for Cys of amino acid at position 148 is changed from TGT to GCA, the base sequence that codes for Ala, the base sequence that codes for Ile of amino acid at position 182 is changed from ATT to ATG, the base sequence that codes for Met; and of the amino acids present in the activation region domain, the base sequence that codes for Val of amino acid at position 184 is changed from GTA to GCC, the base sequence that codes for Ala, the base sequence that codes for Val of amino acid at position 184 is changed from GTA to GCA, the base sequence that codes for Ala, the base sequence that codes for Met of amino acid at position 253 is changed from ATG to CTA, the base sequence that codes for Leu, the base sequence that codes for Phe of amino acid at position 262 is changed from TTC to TAT, the base sequence that codes for Tyr, the base sequence that codes for Ala of amino acid at position 286 is changed from GCT to GAC, the base sequence that codes for Asp, the base sequence that codes for Lys of amino acid at position 290 is changed from AAA to CAC, the base sequence that codes for His, the base sequence that codes for Ala of amino acid at position 295 is changed from GCA to TCA, the base sequence that codes for Ser, the base sequence that codes for Ile of amino acid at position 303 is changed from ATT to ACA, the base sequence that codes for Thr, the base sequence that codes for Phe of amino acid at position 317 is changed from TTC to CAG, the base sequence that codes for Gln, the base sequence that codes for Pro of amino acid at position 335 is changed from CCT to GCT, the base sequence that codes for Ala, the base sequence that codes for Gly of amino acid at position 352 is changed from GGC to GCA, the base sequence that codes for Ala, the base sequence that codes for Arg of amino acid at position 353 is changed from CGT to CAT, the base sequence that codes for His, the base sequence that codes for Glu of amino acid at position 386 is changed from GAA to TCC, the base sequence that codes for Ser, the base sequence that codes for Glu of amino acid at position 430 is changed from GAA to TTC, the base sequence that codes for Phe, the base sequence that codes for Arg of amino acid at position 443 is changed from AGA to ATG, the base sequence that codes for Met, the base sequence that codes for Ser of amino acid at position 446 is changed from TCT to TAC, the base sequence that codes for Tyr, the base sequence that codes for Ser of amino acid at position 446 is changed from TCT to CAA, the base sequence that codes for Gln, the base sequence that codes for Asp of amino acid at position 460 is changed from GAT to ATT, the base sequence that codes for Ile, the base sequence that codes for Asp of amino acid at position 460 is changed from GAT to AAT, the base sequence that codes for Asn, the base sequence that codes for Asp of amino acid at position 460 is changed from GAT to TGT, the base sequence that codes for Cys, the base sequence that codes for Asp of amino acid at position 460 is changed from GAT to CAG, the base sequence that codes for Gln, the base sequence that codes for Asp of amino acid at position 460 is changed from GAT to CCC, the base sequence that codes for Pro, the base sequence that codes for Asp of amino acid at position 460 is changed from GAT to CCT, the base sequence that codes for Pro, the base sequence that codes for Asp of amino acid at position 460 is changed from GAT to CCG, the base sequence that codes for Pro, the base sequence that codes for Asp of amino acid at position 460 is changed from GAT to TCA, the base sequence that codes for Ser, the base sequence that codes for Pro of amino acid at position 466 is changed from CCG to AAC, the base sequence that codes for Asn, the base sequence that codes for Pro of amino acid at position 466 is changed from CCG to GGC, the base sequence that codes for Gly, the base sequence that codes for Pro of amino acid at position 466 is changed from CCG to TCT, the base sequence that codes for Ser, the base sequence that codes for Ser of amino acid at position 471 is changed from AGC to TAT, the base sequence that codes for Tyr, the base sequence that codes for Gly of amino acid at position 475 is changed from GGC to AAT, the base sequence that codes for Asn, the base sequence that codes for Asp of amino acid at position 506 is changed from GAC to CCA, the base sequence that codes for Pro, the base sequence that codes for Val of amino acid at position 524 is changed from GTT to TTA, the base sequence that codes for Leu, the base sequence that codes for Val of amino acid at position 524 is changed from GTT to CTG, the base sequence that codes for Leu, the base sequence that codes for Ile of amino acid at position 539 is changed from ATC to TGC, the base sequence that codes for Cys, the base sequence that codes for Ile of amino acid at position 539 is changed from ATC to CTT, the base sequence that codes for Leu, the base sequence that codes for Ile of amino acid at position 539 is changed from ATC to CTA, the base sequence that codes for Leu, the base sequence that codes for Thr of amino acid at position 544 is changed from ACC to GCG, the base sequence that codes for Ala, the base sequence that codes for Thr of amino acid at position 544 is changed from ACC to GCT, the base sequence that codes for Ala, the base sequence that codes for Thr of amino acid at position 544 is changed from ACC to TCT, the base sequence that codes for Ser, the base sequence that codes for Thr of amino acid at position 544 is changed from ACC to TCC, the base sequence that codes for Ser, the base sequence that codes for Thr of amino acid at position 544 is changed from ACC to CCT, the base sequence that codes for Pro, the base sequence that codes for Thr of amino acid at position 544 is changed from ACC to CCG, the base sequence that codes for Pro, the base sequence that codes for Ala of amino acid at position 546 is changed from GCA to AGC, the base sequence that codes for Ser, the base sequence that codes for Leu of amino acid at position 553 is changed from CTG to GTA, the base sequence that codes for Val, the base sequence that codes for Ala of amino acid at position 623 is changed from GCA to TGT, the base sequence that codes for Cys, the base sequence that codes for Ala of amino acid at position 623 is changed from GCA to TTT, the base sequence that codes for Phe, the base sequence that codes for Ala of amino acid at position 623 is changed from GCA to TTC, the base sequence that codes for Phe, the base sequence that codes for Ala of amino acid at position 623 is changed from GCA to CAG, the base sequence that codes for Gln, the base sequence that codes for Lys of amino acid at position 626 is changed from AAA to GTG, the base sequence that codes for Val, the base sequence that codes for Tyr of amino acid at position 636 is changed from TAC to TGT, the base sequence that codes for Cys, the base sequence that codes for Tyr of amino acid at position 636 is changed from TAC to CCC, the base sequence that codes for Pro, the base sequence that codes for Ala of amino acid at position 646 is changed from GCC to TTG, the base sequence that codes for Leu, the base sequence that codes for Ala of amino acid at position 646 is changed from GCC to ATC, the base sequence that codes for Ile, the base sequence that codes for Met of amino acid at position 648 is changed from ATG to TCT, the base sequence that codes for Ser, the base sequence that codes for Met of amino acid at position 648 is changed from ATG to TCC, the base sequence that codes for Ser, the base sequence that codes for Lys of amino acid at position 710 is changed from AAA to ACG, the base sequence that codes for Thr, the base sequence that codes for Glu of amino acid at position 711 is changed from GAA to GAC, the base sequence that codes for Asp.

To be more specific, examples include mutant lysine decarboxylase in which at least one or more of the following replacement is performed in the amino acid sequence shown in SEQ ID NO: 3 of the sequence listing:

of the amino acids present in the wing domain, the base sequence that codes for Phe of amino acid at position 14 is changed from TTT to CAA, the base sequence that codes for Gln, the base sequence that codes for Leu of amino acid at position 22 is changed from CTT to TTG, the base sequence that codes for Leu, the base sequence that codes for Arg of amino acid at position 28 is changed from CGT to ATT, the base sequence that codes for Ile, the base sequence that codes for Arg of amino acid at position 39 is changed from CGT to ATA, the base sequence that codes for Ile, the base sequence that codes for Arg of amino acid at position 39 is changed from CGT to ATC, the base sequence that codes for Ile, the base sequence that codes for Arg of amino acid at position 39 is changed from CGT to GTG, the base sequence that codes for Val, the base sequence that codes for Leu of amino acid at position 64 is changed from CTC to AAA, the base sequence that codes for Lys, the base sequence that codes for Cys of amino acid at position 67 is changed from TGC to ACC, the base sequence that codes for Thr, the base sequence that codes for Cys of amino acid at position 67 is changed from TGC to TTA, the base sequence that codes for Leu, the base sequence that codes for Ile of amino acid at position 70 is changed from ATT to TTG, the base sequence that codes for Leu, the base sequence that codes for Ile of amino acid at position 70 is changed from ATT to CTG, the base sequence that codes for Leu, the base sequence that codes for Ile of amino acid at position 70 is changed from ATT to CCG, the base sequence that codes for Pro, the base sequence that codes for Glu of amino acid at position 75 is changed from GAG to CCC, the base sequence that codes for Pro, the base sequence that codes for Glu of amino acid at position 75 is changed from GAG to CAC, the base sequence that codes for His, the base sequence that codes for Leu of amino acid at position 79 is changed from TTG to ATA, the base sequence that codes for Ile, the base sequence that codes for Ala of amino acid at position 83 is changed from GCT to CTG, the base sequence that codes for Leu, the base sequence that codes for Ala of amino acid at position 83 is changed from GCT to CTA, the base sequence that codes for Leu, the base sequence that codes for Ala of amino acid at position 83 is changed from GCT to CTT, the base sequence that codes for Leu, the base sequence that codes for Ala of amino acid at position 83 is changed from GCT to ATA, the base sequence that codes for Ile, the base sequence that codes for Ala of amino acid at position 83 is changed from GCT to GCC, the base sequence that codes for Ala, the base sequence that codes for Asn of amino acid at position 84 is changed from AAT to GAC, the base sequence that codes for Asp, the base sequence that codes for Asn of amino acid at position 84 is changed from AAT to ACA, the base sequence that codes for Thr, the base sequence that codes for Thr of amino acid at position 85 is changed from ACG to CCA, the base sequence that codes for Pro, the base sequence that codes for Thr of amino acid at position 88 is changed from ACT to AAA, the base sequence that codes for Lys, the base sequence that codes for Thr of amino acid at position 88 is changed from ACT to AAG, the base sequence that codes for Lys, the base sequence that codes for Thr of amino acid at position 88 is changed from ACT to AGA, the base sequence that codes for Arg, the base sequence that codes for Thr of amino acid at position 88 is changed from ACT to AAT, the base sequence that codes for Asn, the base sequence that codes for Leu of amino acid at position 89 is changed from CTC to TTT, the base sequence that codes for Phe, the base sequence that codes for Asn of amino acid at position 94 is changed from AAT to ATC, the base sequence that codes for Ile, the base sequence that codes for Asp of amino acid at position 95 is changed from GAC to CCG, the base sequence that codes for Pro, the base sequence that codes for Leu of amino acid at position 98 is changed from TTA to ATA, the base sequence that codes for Ile, the base sequence that codes for Gln of amino acid at position 99 is changed from CAG to ACT, the base sequence that codes for Thr, the base sequence that codes for Glu of amino acid at position 104 is changed from GAA to AAT, the base sequence that codes for Asn, the base sequence that codes for Glu of amino acid at position 104 is changed from GAA to AAA, the base sequence that codes for Lys, the base sequence that codes for Asp of amino acid at position 112 is changed from GAT to GAG, the base sequence that codes for Glu, the base sequence that codes for Gln of amino acid at position 119 is changed from CAG to AAC, the base sequence that codes for Asn, the base sequence that codes for Gln of amino acid at position 119 is changed from CAG to AAT, the base sequence that codes for Asn, the base sequence that codes for Gln of amino acid at position 119 is changed from CAG to ATT, the base sequence that codes for Ile, the base sequence that codes for Gln of amino acid at position 119 is changed from CAG to ACC, the base sequence that codes for Thr, the base sequence that codes for Gln of amino acid at position 119 is changed from CAG to AGT, the base sequence that codes for Ser; of the amino acids present in the linker domain, the base sequence that codes for Phe of amino acid at position 137 is changed from TTT to GTC, the base sequence that codes for Val, the base sequence that codes for Lys of amino acid at position 138 is changed from AAA to ATC, the base sequence that codes for Ile, the base sequence that codes for Tyr of amino acid at position 139 is changed from TAT to GTA, the base sequence that codes for Val, the base sequence that codes for Tyr of amino acid at position 139 is changed from TAT to GTG, the base sequence that codes for Val, the base sequence that codes for Tyr of amino acid at position 139 is changed from TAT to TGC, the base sequence that codes for Cys, the base sequence that codes for Tyr of amino acid at position 139 is changed from TAT to ACA, the base sequence that codes for Thr, the base sequence that codes for Tyr of amino acid at position 139 is changed from TAT to TCT, the base sequence that codes for Ser, the base sequence that codes for Tyr of amino acid at position 139 is changed from TAT to AGT, the base sequence that codes for Ser, the base sequence that codes for Tyr of amino acid at position 139 is changed from TAT to AAC, the base sequence that codes for Asn, the base sequence that codes for Gly of amino acid at position 143 is changed from GGT to GAA, the base sequence that codes for Glu, the base sequence that codes for Tyr of amino acid at position 145 is changed from TAT to CGT, the base sequence that codes for Arg, the base sequence that codes for Tyr of amino acid at position 145 is changed from TAT to AGA, the base sequence that codes for Arg, the base sequence that codes for Cys of amino acid at position 148 is changed from TGT to AGT, the base sequence that codes for Ser, the base sequence that codes for Cys of amino acid at position 148 is changed from TGT to TCT, the base sequence that codes for Ser, the base sequence that codes for Cys of amino acid at position 148 is changed from TGT to TCC, the base sequence that codes for Ser, the base sequence that codes for Cys of amino acid at position 148 is changed from TGT to TCA, the base sequence that codes for Ser, the base sequence that codes for Cys of amino acid at position 148 is changed from TGT to GCG, the base sequence that codes for Ala, the base sequence that codes for Cys of amino acid at position 148 is changed from TGT to GCA, the base sequence that codes for Ala, the base sequence that codes for Ile of amino acid at position 182 is changed from ATT to ATG, the base sequence that codes for Met;

of the amino acids present in the pyridoxal phosphate enzyme co-domain, the base sequence that codes for Val of amino acid at position 184 is changed from GTA to GCC, the base sequence that codes for Ala, the base sequence that codes for Val of amino acid at position 184 is changed from GTA to GCA, the base sequence that codes for Ala, the base sequence that codes for Met of amino acid at position 253 is changed from ATG to CTA, the base sequence that codes for Leu, the base sequence that codes for Phe of amino acid at position 262 is changed from TTC to TAT, the base sequence that codes for Tyr, the base sequence that codes for Ala of amino acid at position 286 is changed from GCT to GAC, the base sequence that codes for Asp, the base sequence that codes for Lys of amino acid at position 290 is changed from AAA to CAC, the base sequence that codes for His, the base sequence that codes for Ala of amino acid at position 295 is changed from GCA to TCA, the base sequence that codes for Ser, the base sequence that codes for Ile of amino acid at position 303 is changed from ATT to ACA, the base sequence that codes for Thr, the base sequence that codes for Phe of amino acid at position 317 is changed from TTC to CAG, the base sequence that codes for Gln, the base sequence that codes for Pro of amino acid at position 335 is changed from CCT to GCT, the base sequence that codes for Ala, the base sequence that codes for Gly of amino acid at position 352 is changed from GGC to GCA, the base sequence that codes for Ala, the base sequence that codes for Arg of amino acid at position 353 is changed from CGT to CAT, the base sequence that codes for His, the base sequence that codes for Glu of amino acid at position 386 is changed from GAA to TCC, the base sequence that codes for Ser; and of the amino acids present in the substrate entrance/exit, the base sequence that codes for Glu of amino acid at position 430 is changed from GAA to TTC, the base sequence that codes for Phe, the base sequence that codes for Arg of amino acid at position 443 is changed from AGA to ATG, the base sequence that codes for Met, the base sequence that codes for Ser of amino acid at position 446 is changed from TCT to TAC, the base sequence that codes for Tyr, the base sequence that codes for Ser of amino acid at position 446 is changed from TCT to CAA, the base sequence that codes for Gln, the base sequence that codes for Asp of amino acid at position 460 is changed from GAT to ATT, the base sequence that codes for Ile, the base sequence that codes for Asp of amino acid at position 460 is changed from GAT to AAT, the base sequence that codes for Asn, the base sequence that codes for Asp of amino acid at position 460 is changed from GAT to TGT, the base sequence that codes for Cys, the base sequence that codes for Asp of amino acid at position 460 is changed from GAT to CAG, the base sequence that codes for Gln, the base sequence that codes for Asp of amino acid at position 460 is changed from GAT to CCC, the base sequence that codes for Pro, the base sequence that codes for Asp of amino acid at position 460 is changed from GAT to CCT, the base sequence that codes for Pro, the base sequence that codes for Asp of amino acid at position 460 is changed from GAT to CCG, the base sequence that codes for Pro, the base sequence that codes for Asp of amino acid at position 460 is changed from GAT to TCA, the base sequence that codes for Ser, the base sequence that codes for Pro of amino acid at position 466 is changed from CCG to AAC, the base sequence that codes for Asn, the base sequence that codes for Pro of amino acid at position 466 is changed from CCG to GGC, the base sequence that codes for Gly, the base sequence that codes for Pro of amino acid at position 466 is changed from CCG to TCT, the base sequence that codes for Ser, the base sequence that codes for Ser of amino acid at position 471 is changed from AGC to TAT, the base sequence that codes for Tyr, the base sequence that codes for Gly of amino acid at position 475 is changed from GGC to AAT, the base sequence that codes for Asn, the base sequence that codes for Asp of amino acid at position 506 is changed from GAC to CCA, the base sequence that codes for Pro, the base sequence that codes for Val of amino acid at position 524 is changed from GTT to TTA, the base sequence that codes for Leu, the base sequence that codes for Val of amino acid at position 524 is changed from GTT to CTG, the base sequence that codes for Leu, the base sequence that codes for Ile of amino acid at position 539 is changed from ATC to TGC, the base sequence that codes for Cys, the base sequence that codes for Ile of amino acid at position 539 is changed from ATC to CTT, the base sequence that codes for Leu, the base sequence that codes for Ile of amino acid at position 539 is changed from ATC to CTA, the base sequence that codes for Leu, the base sequence that codes for Thr of amino acid at position 544 is changed from ACC to GCG, the base sequence that codes for Ala, the base sequence that codes for Thr of amino acid at position 544 is changed from ACC to GCT, the base sequence that codes for Ala, the base sequence that codes for Thr of amino acid at position 544 is changed from ACC to TCT, the base sequence that codes for Ser, the base sequence that codes for Thr of amino acid at position 544 is changed from ACC to TCC, the base sequence that codes for Ser, the base sequence that codes for Thr of amino acid at position 544 is changed from ACC to CCT, the base sequence that codes for Pro, the base sequence that codes for Thr of amino acid at position 544 is changed from ACC to CCG, the base sequence that codes for Pro, the base sequence that codes for Ala of amino acid at position 546 is changed from GCA to AGC, the base sequence that codes for Ser, the base sequence that codes for Leu of amino acid at position 553 is changed from CTG to GTA, the base sequence that codes for Val, the base sequence that codes for Ala of amino acid at position 623 is changed from GCA to TGT, the base sequence that codes for Cys, the base sequence that codes for Ala of amino acid at position 623 is changed from GCA to TTT, the base sequence that codes for Phe, the base sequence that codes for Ala of amino acid at position 623 is changed from GCA to TTC, the base sequence that codes for Phe, the base sequence that codes for Ala of amino acid at position 623 is changed from GCA to CAG, the base sequence that codes for Gln, the base sequence that codes for Lys of amino acid at position 626 is changed from AAA to GTG, the base sequence that codes for Val, the base sequence that codes for Tyr of amino acid at position 636 is changed from TAC to TGT, the base sequence that codes for Cys, the base sequence that codes for Tyr of amino acid at position 636 is changed from TAC to CCC, the base sequence that codes for Pro, the base sequence that codes for Ala of amino acid at position 646 is changed from GCC to TTG, the base sequence that codes for Leu, the base sequence that codes for Ala of amino acid at position 646 is changed from GCC to ATC, the base sequence that codes for Ile, the base sequence that codes for Met of amino acid at position 648 is changed from ATG to TCT, the base sequence that codes for Ser, the base sequence that codes for Met of amino acid at position 648 is changed from ATG to TCC, the base sequence that codes for Ser, the base sequence that codes for Lys of amino acid at position 710 is changed from AAA to ACG, the base sequence that codes for Thr, the base sequence that codes for Glu of amino acid at position 711 is changed from GAA to GAC, the base sequence that codes for Asp.

The base sequence after the change is not particularly limited as long as characteristics are better than the enzyme of the original sequence, but the base sequences produced with the sequences shown in Tables 1 to 6 are particularly preferable.

(5) Production Method of Mutant Lysine Decarboxylase

In the production method of the mutant lysine decarboxylase in the present invention (in the following, also simply referred to as "production method"), a transformant is cultured, and the mutant lysine decarboxylase is collected from the at least any of the cultured transformant and the culture of the transformant.

The transformant is a transformant that is transformed with an expression vector containing nucleic acid expressed with a base sequence that codes for the amino acid sequence of the mutant lysine decarboxylase.

In the production method of the mutant lysine decarboxylase in the present invention, the mutant lysine decarboxylase is produced by cultivating a transformant transformed with an expression vector containing nucleic acid expressed with a base sequence that codes for the amino acid sequence of the mutant lysine decarboxylase. With this production method, even under harsh conditions where enzymes are easily inactivated, stable activities are shown, and the mutant lysine decarboxylase that does not significantly decrease initial velocity of reaction even relative to a corresponding wild type lysine decarboxylase can be produced at low costs.

In the following, steps that can be included in the production method are described, but the production method of the mutant lysine decarboxylase of the present invention is sufficient as long as it includes a step of culturing a transformant transformed with an expression vector containing nucleic acid expressed with a base sequence that codes for the amino acid sequence of the mutant lysine decarboxylase (host cell culture step), and a step of collecting the mutant lysine decarboxylase from at least any of cultured transformant and the culture of the transformant (mutant lysine decarboxylase collection step), and as necessary, other steps may further be included.

(6) Transformant Culture Step

The transformant culture step is a step of culturing a transformant transformed with an expression vector containing nucleic acid expressed with a base sequence that codes for the amino acid sequence of the mutant lysine decarboxylase.

[Transformant]

In the production method of the present invention, the transformant is not particularly limited as long as the transformant is transformed with an expression vector containing nucleic acid expressed with a base sequence that codes for the amino acid sequence of the mutant lysine decarboxylase.

Examples of transformants include those having host cells derived from cells of, for example, bacteria, yeast, actinomycete, and filamentous bacterium, and preferably, those having host cells derived from cells of *Escherichia coli* and *Corynebacterium* bacteria.

[Nucleic Acid]

The nucleic acid is expressed with a base sequence that codes for the amino acid sequence of the mutant lysine decarboxylase.

The base sequence that codes for the amino acid sequence of the mutant lysine decarboxylase can be synthesized by a method in which a mutation site is introduced into a base sequence that codes for a corresponding wild type lysine decarboxylase.

[Expression Vector]

The expression vector is not particularly limited as long as the nucleic acid expressed with the base sequence that codes for the amino acid sequence of the mutant lysine decarboxylase is included, but in view of improvement in transformation efficiency and translation efficiency, plasmid vectors and phage vectors having a structure shown below are more preferable.

[Basic Structure of Expression Vector]

The expression vector is not particularly limited as long as the expression vector contains a base sequence that codes for the mutant lysine decarboxylase, and is capable of transforming the host cell. As necessary, other than the base sequence, a base sequence (in the following, also may be simply referred to as "other region") that forms other regions may also be contained.

Examples of the other region include a control region that is necessary for the transformant to produce the mutant lysine decarboxylase, and a region that is necessary for autonomous replication.

Furthermore, in view of allowing easy selection of the transformant, a base sequence that codes for a selection gene that can be a selection marker may further be included.

Examples of the control region that is necessary for producing the mutant lysine decarboxylase include a promoter sequence (including operator sequence that controls transcription), a ribosome binding sequence (SD sequence), and a transcription termination sequence.

[Expression Vector when Prokaryotes are Used as Host Cell]

When prokaryotes are used as the host cell, the expression vector preferably include, in addition to the base sequence that codes for the mutant lysine decarboxylase, in view of production efficiency of the mutant lysine decarboxylase, a promoter sequence. Furthermore, other than the promoter sequence, a ribosome binding sequence and a transcription termination sequence may be included.

Examples of the promoter sequence include *Escherichia coli*-derived trp promoter of tryptophan operon, lac promoter of lactose operon, lambda phage derived PL promoter and PR promoter, *Bacillus subtilis* derived gluconic acid synthesis enzyme promoter (gnt), alkaline protease promoter (apr), neutral protease promoter (npr), and α-amylase promoter (amy).

Also, an originally modified or designed promoter sequence such as tac promoter can be used.

Examples of the ribosome binding sequence include *Escherichia coli*-derived or *Bacillus subtilis* derived sequence, but is not particularly limited as long as the sequence functions in the desired host cell such as *Escherichia coli* and *Bacillus subtilis*.

Examples of the ribosome binding sequence include, of the sequences complementary to 3' terminal region of 16S ribosomal RNA, a consensus sequence having four or more bases arranged continuously made by DNA synthesis.

The transcription termination sequence is not absolutely necessary, but those not dependent on ρ-factor, for example, lipoprotein terminator and trp operon terminator may be used.

The sequence order of these control regions on the expression vector is not particularly limited, but in view of transcription efficiency, it is desirable that the sequence order is, from the 5' terminal side upstream, a promoter sequence, a ribosome binding sequence, a gene that codes for target protein, and a transcription termination sequence.

Specific examples of the expression vector that can be used are pBR322, pUC18, Bluescript II SK (+), pKK223-3, and pSC101 that have a region capable of autonomous replication in *Escherichia coli*; and pUB110, pTZ4, pC194, ρ11, φ1, φ105 that have a region capable of autonomous replication in *Bacillus subtilis*.

Examples of expression vectors that are capable of autonomous replication in two or more types of host include pHV14, TRp7, YEp7, and pBS7, and they can be used as expression vectors.

[Production Method of Transformant]

The transformant in the present invention can be produced by a known method. For example, in a method, the expression vector including the base sequence that codes for the mutant lysine decarboxylase of the present invention and as necessary the other regions as described above is developed, and the expression vector is transformed to a desired host cell. To be specific, a known general method in the field of molecular biology, biological engineering, and genetic engineering described in, for example, Sambrook, J., et. al., "Molecular Cloning A Laboratory Manual, 3rd Edition", Cold Spring Harbor Laboratory Press, (2001) can be used.

Furthermore, a method of introduction into chromosome using homologous recombination can be used.

The transformant in the present invention can be produced by, not only introduction of the expression vector into the host cell, but as necessary, a silent mutation can also be introduced so that codons less frequently used in the host cell can be frequently used.

In this way, the production amount of the protein derived from the mutant lysine decarboxylase introduced into the expression vector may be increased.

In the introduction of the silent mutation, the method, mutation site, and types of the base to be changed are not particularly limited as long as the codons of the expression vector are in accordance with the codon use frequency of the host cell.

[Cultivation Method of Transformant]

The medium that culture the transformant of the present invention contains a carbon source, a nitrogen source, and inorganic salts that can be utilized by the host, and as long as the medium can culture the transformant efficiently, any of a natural medium and a synthetic medium may be used.

Examples of carbon sources include saccharides such as glucose, lactose, galactose, fructose, arabinose, maltose, xylose, trehalose, ribose, and hydrolysate of starch; alcohols such as glycerol, mannitol, and sorbitol; and organic acids such as gluconic acid, fumaric acid, citric acid, and succinic acid.

Such a carbon source may be used singly, or may be used in combination.

Examples of nitrogen sources include inorganic ammonium salts such as ammonium sulfate, ammonium chloride, and ammonium phosphate; organic nitrogen such as soybean hydrolysate; ammonia gas; and ammonia water.

Such a nitrogen source may be used singly, or may be used in combination.

Examples of inorganic ions include sodium ions, magnesium ions, potassium ions, calcium ions, chloride ions, manganese ions, iron ions, phosphoric acid ions, and sulfuric acid ions.

Such an inorganic ion may be used singly, or may be used in combination.

To the medium, as necessary, other organic components (organic micronutrients) may be added, and examples of such organic components include various amino acids; vitamins such as vitamin B1; required substances of nucleic acids such as RNA; and yeast extracts.

Examples of such a medium include LB medium, YT medium, and M9 medium.

Of those examples of such a medium, preferably, LB medium is used.

The conditions for culture of transformant can be selected suitably depending on the types of the transformant, medium, and culture method, and are not particularly limited as long as the transformant grows and the mutant lysine decarboxylase of the present invention can be produced. For example, when *Escherichia coli* is cultured, culture can be performed until the protein content of a target protein having mutant lysine decarboxylase activity is the maximum under aerobic conditions, a culture temperature of, for example, 20 to 45° C., preferably 25 to 40° C., a culture pH of, for example, 5.0 to 8.5, preferably 6.5 to 8.0, and a culture period in a range of 1 to 7 days.

For example, the culture period is 12 to 72 hours, preferably 14 to 48 hours. For adjustment of pH, for example, inorganic or organic acidic or alkaline substances, or ammonia gas may be used.

The culturing can be performed, in a liquid medium containing the medium, by a general culture method such as shaking culture, aerated and agitated culture, continuous culture, and fed-batch culture.

The lysine decarboxylase collection step is a step in which the mutant lysine decarboxylase is collected from at least any of the cultured transformant and the culture of the transformant.

The mutant lysine decarboxylase of the present invention can be collected after culturing the transformed transformant by a method commonly used in this field.

When the mutant lysine decarboxylase of the present invention is secreted outside the transformed transformant, the culture of the transformant can be subjected to centrifugal separation and filtration so that a crude enzyme solution can be obtained easily. Furthermore, when the mutant lysine decarboxylase of the present invention is accumulated in the transformed transformant, the cultured transformant is collected by means such as centrifugal separation, and the collected transformant is suspended in water or a buffer solution, and the cell membrane of the transformant is broken by a known method such as lysozyme treatment, freeze thawing, and ultrasonic disruption, to collect the crude enzyme solution.

The crude enzyme solution can be condensed, for example, by ultrafiltration, and for example, an antiseptic can be added thereto for use as a condensed enzyme. Furthermore, powder enzyme of the mutant lysine decarboxylase can also be obtained by spray-drying after the condensation.

When the collected crude enzyme solution having lysine decarboxylase activity has to be separated and purified, for example, salting out with ammonium sulfate, organic solvent precipitation with alcohol, membrane separation such as dialysis and ultrafiltration, or a known chromatographic separation such as ion exchanger chromatography, reversed phase high-performance chromatography, affinity chromatography, and gel filtration chromatography can be conducted in a suitable combination.

The mutant lysine decarboxylase obtained as described above is included in the range of the present invention.

(7) Method for Producing 1,5-Pentamethylenediamine

The mutant lysine decarboxylase produced as described above can be used in substance production as an enzyme catalyst. For example, by allowing lysine to contact with the aforementioned mutant lysine decarboxylase, 1,5-pentamethylenediamine can be produced. That is, lysine; at least one selected from the group consisting of mutant lysine decarboxylase, a transformant that expresses mutant lysine decarboxylase, a treated transformant, and immobilized transformant and treated transformant; and a reaction solvent are mixed, and the lysine decarboxylase and lysine are brought into contact in the reaction solvent, thereby producing 1,5-pentamethylenediamine by lysine decarboxylation.

The lysine used as a material in the present invention may be a salt of lysine. Examples of lysine salts include hydrochloride, acetate, carbonate, hydrogen carbonate, sulfate, and nitrate.

Of such a lysine salt, preferably, lysine hydrochloride is used.

The lysine concentration in the reaction solvent is not particularly limited, and is, for example, 1 to 70 mass %, preferably 2 to 50 mass %.

In the presence of a substance that prevents deceleration or stoppage of reaction of the present invention, a necessary amount of mutant lysine decarboxylase is, when the lysine concentration in the reaction solvent is 10 mass % or less, 5 U or more and 165 U or less, even more preferably 20 U or more and 82.5 U or less per 1 g of lysine hydrochloride. On the purified enzyme basis, the necessary amount of mutant lysine decarboxylase is, when the lysine concentration in the reaction solvent is 10 mass % or less, 5 µg or more and 165 µg or less, even more preferably 20 µg or more and 82.5 µg or less per 1 g of lysine hydrochloride.

In the case of amount basis of catalyst resting bacterial cell or catalyst inactivated bacterial cell, when the lysine concentration in the reaction solvent is 10 mass % or less, 5 mg or more and 161 mg or less, even more preferably 5.4 mg or more and 80 mg or less per 100 g of lysine hydrochloride.

When the lysine concentration is more than 10 mass % and below 45 mass %, the necessary amount of mutant lysine decarboxylase per 1 g of lysine hydrochloride is 5 U or more and 165 U or less, more preferably 20 U or more and 110 U or less, and on the purified enzyme basis, the necessary amount of mutant lysine decarboxylase per 1 g of lysine hydrochloride is 5 µg or more and 165 µg or less, even more preferably 20 µg or more and 110 µg or less.

When the lysine concentration is 45 mass % or more, 5 U or more and 165 U or less, more preferably 100 U or more and 165 U or less per 1 g of lysine hydrochloride, and on the purified enzyme basis, the necessary amount of mutant lysine decarboxylase per 1 g of lysine hydrochloride is 5 µg or more and 165 µg or less, even more preferably 100 µg or more and 165 µg or less.

Examples of reaction solvents include water, aqueous mediums, organic solvents, and a mixture of water or an aqueous medium and an organic solvent.

Examples of aqueous mediums include a buffer solution such as a phosphoric acid buffer solution.

Examples of organic solvents include any organic solvents that do not hinder the reaction.

The conditions of lysine decarboxylation are as follows: a temperature of, for example, 28 to 55° C., preferably 35 to 45° C., and a time period of, for example, 0.1 to 72 hours, preferably 1 to 72 hours, more preferably, 12 to 36 hours. The reaction pH is, for example, 5.0 to 9.0, preferably 5.5 to 8.5.

The reaction may be conducted while shaking, stirring, or standing.

Decarboxylation of lysine is conducted in this manner, thereby converting to and producing 1,5-pentamethylenediamine.

1,5-pentamethylenediamine produced in the present invention may be a salt of 1,5-pentamethylenediamine.

Examples of salts of 1,5-pentamethylenediamine include hydrochloride, acetate, carbonate, hydrogen carbonate, sulfate, or nitrate of 1,5-pentamethylenediamine.

Of such salts of 1,5-pentamethylenediamine, preferably, hydrochloride is used.

In this reaction, the produced 1,5-pentamethylenediamine is alkaline, and therefore along with conversion of lysine to 1,5-pentamethylenediamine, the pH of the reaction solution may increase. In such a case, as necessary, an acidic substance (e.g., organic acid, and inorganic acid such as hydrochloric acid) can be added to adjust the pH.

In this reaction, as necessary, for example, vitamin $B_6$ and/or derivatives thereof can be added to the reaction liquid.

Examples of vitamin $B_6$ and/or its derivatives include pyridoxine, pyridoxamine, pyridoxal, and pyridoxal phosphate.

Such a vitamin $B_6$ and/or its derivative may be used singly, or may be used in combination.

Of the vitamin $B_6$ and/or its derivative, preferably, pyridoxal phosphate is used.

By adding vitamin $B_6$ and/or its derivative, production speed and reaction yield of 1,5-pentamethylenediamine can be improved. In this method, from the obtained aqueous solution of pentamethylenediamine, as necessary, a portion of water can be distilled off To be more specific, for example, the aqueous solution of pentamethylenediamine is heated (heat treated) using a distillation apparatus etc. equipped with a continuous multiple distillation column, a batch multiple distillation column, etc. under 0.1 kPa to normal pressure, thereby performing distillation. In this manner, an aqueous solution of pentamethylenediamine in which a portion of water is distilled off can be obtained.

The heating temperature is, for example, 25° C. or more and below 90° C., preferably 25° C. or more and 85° C. or less, more preferably, 25° C. or more and below 80° C., even more preferably, 30° C. or more and 70° C. or less.

When an aqueous solution of pentamethylenediamine is heated (heat treatment) at 90° C. or more, the extractability of pentamethylenediamine (or its salt) may be reduced.

(8) Method for Producing 1,5-Pentamethylene Diisocyanate

Furthermore, when the aqueous solution of pentamethylenediamine is heated (heat treatment) at 90° C. or more, and pentamethylene diisocyanate is produced using the pentamethylenediamine obtained from the aqueous solution, and further an isocyanate modified substance (described later) is produced from the pentamethylene diisocyanate, the reaction velocity may be low, and storage stability of the obtained isocyanate modified substance (described later) may be low.

Therefore, preferably, without heating (heat treatment) the aqueous solution of pentamethylenediamine at 90° C. or more, more preferably, without heating (heat treatment) at 80° C. or more, even more preferably, without heating (heat treatment) the aqueous solution of pentamethylenediamine, as is described later, pentamethylenediamine (or its salt) is extracted as is from the aqueous solution.

Then, in this method, preferably, pentamethylenediamine (or its salt) is extracted from the above-described aqueous solution of pentamethylenediamine. In the extraction, for example, liquid-liquid extraction method is used.

In the liquid-liquid extraction method, for example, the following methods are used: (1) a method in which by bringing an extractant (described later) into contact with the aqueous solution of pentamethylenediamine batchwise, semi-continuously, or continuously, and mixing and stirring them, pentamethylenediamine (or its salt) is extracted (partitioned) to the extractant (described later), and pentamethylenediamine (or its salt) is separated from the extractant (described later); (2) a method in which an aqueous solution of pentamethylenediamine and an extractant (described later) are supplied countercurrently and continuously to a column (spray column, staged extraction column) equipped with a porous plate, or a column (countercurrent differential extraction column, non-mixing staged extraction column: 5th edition, revised, Chemical Engineers Handbook, p 566 to 569, edited by Society of Chemical Engineers, Maruzen (1988)) equipped with filling, a nozzle, an orifice plate, a baffle, an injector and/or a static mixer, pentamethylenediamine (or its salt) is extracted (partitioned) to the extractant (described later), and thereafter, the extractant (described later) is allowed to flow out continuously, and pentamethylenediamine (or its salt) is separated from the extractant (described later), (3) a method in which an aqueous solution of pentamethylenediamine and an extractant (described later) are supplied countercurrently and continuously to a column (stirring staged extraction column: 5th edition, revised, Chemical Engineers Handbook, p 569 to 574, edited by Society of Chemical Engineers, Maruzen (1988)) equipped with a baffle plate and a stirring blade, pentamethylenediamine (or its salt) is extracted (partitioned) to the extractant (described later), thereafter, the extractant (described later) is allowed to flow out continuously, and pentamethylenediamine (or its salt) is separated from the extractant (described later); and (4) an extractant (described later) is brought into contact with an aqueous solution of pentamethylenediamine using a mixer settler extractor, or a centrifugal extraction apparatus (5th edition, revised, Chemical Engineers Handbook, p 563 to 566, and p 574, edited by Society of Chemical Engineers, Maruzen (1988)), pentamethylenediamine (or its salt) is extracted (partitioned) to the extractant (described later), and pentamethylenediamine (or its salt) is separated from the extractant (described later).

These liquid-liquid extraction methods may be used singly or in combination of two or more.

As the liquid-liquid extraction method, in view of production efficiency, preferably, a method in which pentamethylenediamine (or its salt) is extracted (partitioned) to the extractant (described later) continuously, to be more specific, for example, the above-described methods of (1) to (3) are used.

The mixing ratio of the aqueous solution of pentamethylenediamine to the extractant (described later) in the liquid-liquid extraction is, relative to 100 parts by mass of the aqueous solution of pentamethylenediamine (when the extraction is continuous, supplied amount per unit time. The same is applied below as well.), for example, 30 to 300 parts by mass of the extractant (described later), and in view of economy and productivity, preferably 50 to 200 parts by mass, more preferably 50 to 150 parts by mass, particularly preferably 80 to 120 parts by mass.

In the liquid-liquid extraction, the aqueous solution of pentamethylenediamine and the extractant (described later) are mixed, for example, using stirring blade, etc. under normal pressure (atmospheric pressure), at, for example, 5 to 60° C., preferably 10 to 60° C., more preferably 15 to 50° C., even more preferably 15 to 40° C., for, for example, 1 to 120 minutes, preferably 5 to 90 minutes, more preferably 5 to 60 minutes.

Examples of stirring blades include, without limitation, for example, propeller, flat blade, flat blade with angles, flat blade with pitch, flat blade disk turbine, blade with tilt disk turbine, bent blade, Pfaudler type stirring blades, blue margin type, dissolver, and anchor.

The number of revolution in the mixing is, for example, 5 to 3000 rpm, preferably 10 to 2000 rpm, more preferably 20 to 1000 rpm.

In this manner, pentamethylenediamine (or its salt) is extracted into the extractant (described later).

Next, in this method, the mixture of pentamethylenediamine (or its salt) and the extractant (described later) is allowed to stand for, for example, 5 to 300 minutes, preferably 10 to 240 minutes, more preferably 20 to 180 minutes, and thereafter, the extractant (pentamethylenediamine extract, that is, a mixture of the extractant (described later) and the pentamethylenediamine (or its salt)) in which pentamethylenediamine (or its salt) is extracted is taken out by a known method.

When the pentamethylenediamine (or its salt) cannot be sufficiently extracted by one liquid-liquid extraction, the liquid-liquid extraction can be conducted repeatedly a plurality of times (e.g., 2 to 5 times).

In this manner, the pentamethylenediamine (or its salt) in the aqueous solution of pentamethylenediamine can be extracted into the extractant (described later).

In the thus obtained extractant (mixture of the extractant (described later) and pentamethylenediamine (or its salt)), the pentamethylenediamine (or its salt) concentration is, for example, 0.2 to 40 mass %, preferably 0.3 to 35 mass %, more preferably 0.4 to 30 mass %, particularly preferably 0.8 to 25 mass %.

The yield (extraction rate) of pentamethylenediamine (or its salt) after the extraction is, based on lysine (or its salt), for example, 65 to 100 mol %, preferably 70 to 100 mol %, more preferably 80 to 100 mol %, particularly preferably 90 to 100 mol %.

In this method, as necessary, for example, pentamethylenediamine (or its salt) can also be isolated from the mixture of the obtained extractant (described later) and pentamethylenediamine (or its salt). The isolation of pentamethylenediamine (or its salt) is not particularly limited, and for example, the isolation of pentamethylenediamine (or its salt) can be performed by distilling the mixture of the extractant (described later) and pentamethylenediamine (or its salt), using a distillation apparatus including a continuous multistage distillation column, a batch multistage distillation column, etc. at, for example, 50 to 182° C., under 0.1 kPa to normal pressure, removing the extractant (described later).

In such an extraction, examples of extractants include non-halogen organic solvents.

The non-halogen organic solvent is an organic solvent that does not contain halogen atoms (fluorine, chlorine, bromine, iodine, etc.) in the molecule, for example, a non-halogen aliphatic organic solvent, a non-halogen alicyclic organic solvent, and a non-halogen aromatic organic solvent.

Examples of non-halogen aliphatic organic solvents include straight chain non-halogen aliphatic organic solvents, and branched non-halogen aliphatic organic solvents.

Examples of straight chain non-halogen aliphatic organic solvents include straight chain non-halogen aliphatic hydrocarbons, straight chain non-halogen aliphatic ethers, and straight chain non-halogen aliphatic alcohols.

Examples of straight chain non-halogen aliphatic hydrocarbons include n-hexane, n-heptane, n-nonane, n-decane, and n-dodecane.

Examples of straight chain non-halogen aliphatic ethers include diethylether, dibutylether, and dihexylether.

Examples of straight chain non-halogen aliphatic alcohols include straight chain monohydric alcohols having 1 to 3 carbon atoms (e.g., methanol, ethanol, n-propanol, isopropanol, etc.), straight chain monohydric alcohols having 4 to 7 carbon atoms (e.g., n-butanol, n-pentanol, n-hexanol, n-heptanol, etc.), and straight chain monohydric alcohols having 8 or more carbon atoms (e.g., n-octanol, n-nonanol, n-decanol, n-undecanol, n-dodecanol, etc.).

Examples of branched non-halogen aliphatic organic solvents include branched non-halogen aliphatic hydrocarbons, branched non-halogen aliphatic ethers, branched non-halogen aliphatic monohydric alcohols, and branched non-halogen aliphatic polyhydric alcohols.

Examples of branched non-halogen aliphatic hydrocarbons include 2-methylpentane, 2,2-dimethylbutane, 2,3-dimethylbutane, 2-methylhexane, 3-methylhexane, 2,3-dimethylpentane, 2,4-dimethylpentane, n-octane, 2-methylheptane, 3-methylheptane, 4-methylheptane, 3-ethylhexane, 2,2-dimethylhexane, 2,3-dimethylhexane, 2,4-dimethylhexane, 2,5-dimethylhexane, 3,3-dimethylhexane, 3,4-dimethylhexane, 2-methyl-3-ethylpentane, 3-methyl-3-ethylpentane, 2,3,3-trimethylpentane, 2,3,4-trimethylpentane, 2,2,3,3-tetramethylbutane, and 2,2,5-trimethylhexane.

Examples of branched non-halogen aliphatic ethers include diisopropylether and diisobutylether.

Examples of branched non-halogen aliphatic monohydric alcohols include branched monohydric alcohol having 4 to 7 carbon atoms (e.g., 2-butanol, isobutanol, tert-butanol, 2-pentanol, 3-pentanol, isopentanol, 2-methyl-1-butanol, 2-methyl-3-butanol, 2,2-dimethyl-1-propanol, tert-pentanol, 2-hexanol, 3-hexanol, isohexanol, 2-methyl-2-pentanol, 2-methyl-1-pentanol, 3-methyl-1-pentanol, 2-ethyl-1-butanol, 3,3-dimethyl-1-butanol, 2-heptanol, 3-heptanol, 4-heptanol, 5-methyl-1-hexanol, 4-methyl-1-hexanol, 3-methyl-1-hexanol, 2-ethyl-2-methyl-1-butanol, etc.); and branched monohydric alcohols having 8 or more carbon atoms (e.g., isooctanol, isononanol, isodecanol, 5-ethyl-2-nonanol, trimethylnonylalcohol, 2-hexyldecanol, 3,9-diethyl-6-tridecanol, 2-isoheptylisoundecanol, 2-octyldodecanol, etc.).

Examples of branched non-halogen aliphatic polyhydric alcohols include 2-ethyl-1,3-hexanediol.

These non-halogen aliphatic organic solvents may be used singly or in combination of two or more.

As the non-halogen aliphatic organic solvent, preferably, straight chain non-halogen aliphatic organic solvents, more preferably, straight chain non-halogen aliphatic alcohols are used.

When straight chain non-halogen aliphatic alcohols are used, pentamethylenediamine can be extracted in high yield.

As the non-halogen aliphatic organic solvent, preferably, monohydric alcohols having 4 to 7 carbon atoms (straight chain monohydric alcohol having 4 to 7 carbon atoms, branched monohydric alcohol having 4 to 7 carbon atoms) are used.

When monohydric alcohol having 4 to 7 carbon atoms is used, pentamethylenediamine or its salt can be extracted efficiently, and furthermore, impurity content proportion of pentamethylenediamine or its salt can be decreased.

Examples of non-halogen alicyclic organic solvents include non-halogen alicyclic hydrocarbons (e.g., cyclopentane, methylcyclopentane, cyclohexane, methylcyclohexane, ethylcyclohexane, p-menthane, bicyclohexyl, etc.).

These non-halogen alicyclic organic solvents may be used singly or in combination of two or more.

Examples of non-halogen aromatic organic solvents include non-halogen aromatic hydrocarbons (e.g., benzene, toluene, xylene, ethylbenzene, isopropylbenzene, 1,3,5-trimethylbenzene, 1,2,3,4-tetrahydronaphthalene, n-butylbenzene, sec-butylbenzene, tert-butylbenzene, ethylbenzene, etc.), and phenols (e.g., phenol, cresol, etc.).

These non-halogen aromatic organic solvents may be used singly or in combination of two or more.

Examples of non-halogen organic solvents also include a mixture of aliphatic hydrocarbons and aromatic hydrocarbons, and examples of such a mixture include petroleum ether and petroleum benzine.

These non-halogen organic solvents may be used singly or in combination of two or more.

As the extractant, in the range that does not inhibit excellent effects of the present invention, for example, halogen organic solvents (organic solvents containing halogen atoms in its molecule) can be used.

Examples of halogen organic solvents include halogen aliphatic hydrocarbons (e.g., chloroform, dichloromethane, carbon tetrachloride, tetrachloroethylene, etc.), and halogen aromatic hydrocarbons (e.g., chlorobenzene, dichlorobenzene, chlorotoluene, etc.).

These halogen organic solvents may be used singly or in combination of two or more.

On the other hand, if the halogen organic solvent is used as the extractant, when pentamethylene diisocyanate (described later) is produced by using the obtained pentamethylenediamine or its salt, and then the pentamethylene diisocyanate (described later) is allowed to react to produce an isocyanate modified substance (described later), or a polyurethane resin (described later), productivity and physical property (e.g., yellowing resistance, etc.) of the isocyanate modified substance (described later) may be poor.

Also in the case when a polyurethane resin is produced by allowing such pentamethylene diisocyanate (described later) or an isocyanate modified substance (described later) to react with an active hydrogen compound (described later), physical property (e.g., mechanical strength, chemical resistance, etc.) of the obtained polyurethane resin may be poor.

Therefore, as the extractant, preferably, a non-halogen organic solvent, more preferably, a non-halogen aliphatic organic solvent is used.

When pentamethylenediamine or its salt is extracted by using a non-halogen aliphatic organic solvent, when pentamethylene diisocyanate is produced by using such pentamethylenediamine or its salt, pentamethylene diisocyanate that allows efficient production of an isocyanate modified substance having excellent characteristics, or a polyurethane resin having excellent characteristics can be produced.

In the present invention, the boiling point of the extractant is, for example, 60 to 250° C., preferably 80 to 200° C., more preferably 90 to 150° C.

When the boiling point of the extractant is below the above-described lower limit, when obtaining pentamethylenediamine or its salt by extraction from the aqueous solution of pentamethylenediamine, separation from the extractant may become difficult.

On the other hand, when the boiling point of the extractant is more than the above-described upper limit, when obtaining pentamethylenediamine or its salt from a mixture of the extractant and pentamethylenediamine or its salt, consuming energy at the separation process may increase.

The method of obtaining pentamethylenediamine or its salt from the aqueous solution of pentamethylenediamine is not limited to the above-described extraction, and for example, a known isolation and purification method such as distillation can also be used.

From the thus obtained pentamethylenediamine, for example, amide, imide, and epoxy can be derived.

The present invention also include 1,5-pentamethylene diisocyanate (in the following, simply referred to as pentamethylene diisocyanate) produced from the thus obtained 1,5-pentamethylenediamine (or its salt).

1,5-Pentamethylene diisocyanate can be synthesized, for example, by a method by phosgenating 1,5-pentamethylenediamine (or its salt) (hereinafter may be referred to as phosgenation method), and a method by carbamation of 1,5-pentamethylenediamine (or its salt), and thereafter by thermal decomposition (hereinafter may be referred to as carbamation method).

The phosgenation method can be performed, to be more specific, by a method (hereinafter may be referred to as cold/hot two-stage phosgenation method) in which pentamethylenediamine is directly allowed to react with phosgene; or a method (hereinafter may be referred to as amine hydrochloride phosgenation method) in which hydrochloride of pentamethylenediamine is suspended in an inactive solvent (described later) to react with phosgene.

In the cold/hot two-stage phosgenation method, for example, first, an inactive solvent is introduced to a reactor capable of stirring and provided with a phosgene inlet tube, and then the pressure in the reaction system is set to, for example, normal pressure to 1.0 MPa, preferably normal pressure to 0.5 MPa, and the temperature is set to, for example, 0 to 80° C., preferably 0 to 60° C.

Examples of inactive solvents include aromatic hydrocarbons such as benzene, toluene, xylene, ethylbenzene, etc.; aliphatic acid esters such as ethyl acetate, butyl acetate, amyl acetate, etc.; aromatic carboxylic acid esters such as methyl salicylate, dimethyl phthalate, dibutyl phthalate, methyl benzoate, etc.; chlorinated aromatic hydrocarbons such as monodichlorobenzene, orthodichlorobenzene, trichlorobenzene, etc.; and chlorinated hydrocarbons such as chloroform, carbon tetrachloride, etc.

These inactive solvents may be used singly or in combination of two or more.

The blending amount (total amount) of the inactive solvent relative to 100 parts by mass of pentamethylenediamine as a material is, for example, 400 to 3000 parts by mass, preferably 500 to 2000 parts by mass.

Next, in this method, phosgene is introduced, for example, so that the amount of phosgene is 1 to 10 times mol, preferably 1 to 6 times mol relative to one amino group in pentamethylenediamine; and pentamethylenediamine dissolved in the above-described inactive solvent is added. During this time, the reaction liquid is kept at, for example, 0 to 80 to ° C., preferably 0 to 60 to ° C., and at the same time, generated hydrogen chloride is released outside of the reaction system via the reflux condenser (cold phosgenation reaction). The contents of the reactor are thus formed into a slurry.

In the cold phosgenation reaction, pentamethylenedicarbamoyl chloride and amine hydrochloride of pentamethylenediamine are produced.

Next, in this method, the pressure in the reaction system is set to, for example, normal pressure to 1.0 MPa, preferably 0.05 to 0.5 MPa, and the temperature is increased for, for example, 30 minutes to 5 hours, to a temperature range of, for example, 80 to 180° C. After the temperature increase, for example, the reaction is allowed to continue for 30 minutes to 8 hours, thereby dissolving the slurry liquid completely (hot phosgenation reaction).

In the hot phosgenation reaction, at the time of temperature increase and the high temperature reaction, the dissolved phosgene is evaporated and escapes outside the reaction system via the reflux condenser, and therefore phosgene is introduced appropriately until the reflux amount from the reflux condenser can be confirmed.

After the termination of the hot phosgenation reaction, an inactive gas such as nitrogen gas is introduced into the reaction system at, for example, 80 to 180° C., preferably 90 to 160° C., thereby purging dissolved excessive phosgene and hydrogen chloride.

In the hot phosgenation reaction, pentamethylenedicarbamoyl chloride produced in the cold phosgenation reaction is thermally decomposed, pentamethylene diisocyanate is produced, and furthermore, amine hydrochloride of pentamethylenediamine is phosgenated, thereby producing pentamethylene diisocyanate.

On the other hand, in the amine hydrochloride phosgenation method, the hydrochloride of pentamethylenediamine is dried sufficiently and finely pulverized, and thereafter, in the same reactor as the reactor of the above-described cold/hot two-stage phosgenation method, hydrochloride of pentamethylenediamine is stirred in the above-described inactive solvent, thereby dispersing the hydrochloride of pentamethylenediamine to form a slurry.

Next, in this method, the reaction temperature is maintained at, for example, 80 to 180° C., preferably 90 to 160° C., and the reaction pressure is maintained at, for example, normal pressure to 1.0 MPa, preferably 0.05 to 0.5 MPa, and phosgene is introduced for 1 to 10 hours so that the total phosgene amount is 1 to 10 times the stoichiometric amount.

Pentamethylene diisocyanate is synthesized in this manner.

The reaction progress can be assumed based on the amount of the hydrogen chloride gas generated, and when the undissolved slurry in the above-described inactive solvent disappeared and the reaction liquid became clear and homogeneous. The generated hydrogen chloride is released, for example, outside the reaction system via the reflux condenser. At the time of reaction termination, the dissolved excessive phosgene and hydrogen chloride are purged by the above-described method. Thereafter, cooling is performed, and the inactive solvent is distilled off under reduced pressure.

In pentamethylene diisocyanate, the hydrolyzable chlorine concentration (HC) tends to increase, and therefore when the HC has to be reduced in phosgenation method, for example, after phosgenation and solvent removal, the pentamethylene diisocyanate that was distilled off is heat treated at, for example, while passing through inert gas such as nitrogen, for example, 150° C. to 200° C., preferably 160 to 190° C., for example, for 1 to 8 hours, preferably 3 to 6 hours. Thereafter, by rectifying, the HC of pentamethylene diisocyanate can be significantly reduced.

In the present invention, the hydrolyzable chlorine concentration of pentamethylene diisocyanate is, for example, 100 ppm or less, preferably 80 ppm or less, more preferably, 60 ppm or less, even more preferably, 50 ppm or less.

The hydrolyzable chlorine concentration can be measured, for example, in conformity with the hydrolyzable chlorine testing method described in Annex 3 of JIS K-1556 (2000).

When the hydrolyzable chlorine concentration is more than 100 ppm, reaction velocity of trimerization (described later) decreases, and may require a large amount of trimerization catalyst (described later). When a large amount of trimerization catalyst (described later) is used, degree of yellowing of the obtained polyisocyanate composition (described later) may become high, and the number average molecular weight may become high, which may lead to a high viscosity.

When the hydrolyzable chlorine concentration is more than 100 ppm, in a storage step of the polyisocyanate composition (described later), and a production step of polyurethane resin (described later), viscosity and color may be significantly changed.

Examples of carbamation method include urea method.

In urea method, for example, first, carbamation of pentamethylenediamine is performed, thereby producing pentamethylenedicarbamate (PDC).

To be more specific, as reaction materials, pentamethylenediamine, urea and/or N-non-substitute carbamate, and alcohol are allowed to react with each other.

Examples of N-non-substitute carbamates include N-non-substitute carbamic acid aliphatic esters (e.g., methyl carbamate, ethyl carbamate, propyl carbamate, iso-propyl carbamate, butyl carbamate, iso-butyl carbamate, sec-butyl carbamate, tert-butyl carbamate, pentyl carbamate, iso-pentyl carbamate, sec-pentyl carbamate, hexyl carbamate, heptyl carbamate, octyl carbamate, 2-ethylhexyl carbamate, nonyl carbamate, decyl carbamate, isodecyl carbamate, dodecyl carbamate, tetradecyl carbamate, hexadecyl carbamate, etc.); and N-non-substitute carbamic acid aromatic esters (e.g., phenyl carbamate, tolyl carbamate, xylyl carbamate, biphenyl carbamate, naphthyl carbamate, anthryl carbamate, phenanthryl carbamate, etc.).

These N-non-substitute carbamates may be used singly or in combination of two or more.

As the N-non-substitute carbamate, preferably, N-non-substitute carbamic acid aliphatic esters are used.

Examples of alcohols include primary to tertiary monohydric alcohols, to be more specific, aliphatic alcohols and aromatic alcohols.

Examples of aliphatic alcohols include straight chain aliphatic alcohols (e.g., methanol, ethanol, n-propanol, n-butanol (1-butanol), n-pentanol, n-hexanol, n-heptanol, n-octanol (1-octanol), n-nonanol, n-decanol, n-dodecanol, n-tetradecanol, n-hexadecanol, etc.), and branched aliphatic alcohols (e.g., iso-propanol, iso-butanol, sec-butanol, tert-butanol, iso-pentanol, sec-pentanol, 2-ethylhexanol, iso-decanol, etc.).

Examples of aromatic alcohols include phenol, hydroxytoluene, hydroxyxylene, biphenylalcohol, naphthalenol, anthracenol, and phenanthrol.

These alcohols may be used singly or in combination of two or more.

As the alcohol, preferably, aliphatic alcohols, more preferably, straight chain aliphatic alcohols are used.

As the alcohol, preferably, above-described monohydric alcohols having 4 to 7 carbon atoms (straight chain monohydric alcohol having 4 to 7 carbon atoms, and branched monohydric alcohol having 4 to 7 carbon atoms) are used.

Furthermore, when an alcohol (monohydric alcohol having 4 to 7 carbon atoms, etc.) are used as the extractant in the above-described extraction, preferably, the alcohol is used as the reaction material alcohol.

Then, in this method, pentamethylenediamine, urea and/or N-non-substitute carbamate, and alcohol are blended, and preferably, the mixture is allowed to react in the liquid phase.

The mixing ratio of the pentamethylenediamine, urea and/or N-non-substitute carbamate, and alcohol is not particularly limited, and the ratio can be suitably selected in a comparatively wide range.

Usually, the blending amount of urea and N-non-substitute carbamate, and the blending amount (in mol) of the alcohol equal to or more than the amino group of pentamethylenediamine is sufficient, and therefore urea and/or the above-described N-non-substitute carbamate, and the alcohol itself can also be used as the reaction solvent in this reaction.

When an alcohol (monohydric alcohol having 4 to 7 carbon atoms, etc.) is used in the above-described extraction as the extractant, preferably, the alcohol is used as is as the reaction material and reaction solvent.

When urea and/or the above-described N-non-substitute carbamate, or alcohol are used also as the reaction solvent, as necessary, an excessive amount of urea and/or the above-described N-non-substitute carbamate, or alcohol are used, but with an overly excessive amount, consumption energy in the separation process after the reaction increases, and therefore industrially inappropriate.

Thus, in view of improving the yield of carbamate, the blending amount of urea and/or the above-described N-non-substitute carbamate relative to one amino group of pentamethylenediamine is, 0.5 to 20 times mol, preferably 1 to 10 times mol, more preferably 1 to 5 times mol, and the blending amount of alcohol relative to one amino group of pentamethylenediamine is, 0.5 to 100 times mol, preferably 1 to 20 times mol, more preferably 1 to 10 times mol.

In this method, a catalyst can also be used.

The catalyst is not particularly limited, and examples thereof include: a first group (in conformity with IUPAC Periodic Table of the Elements (version date 22 Jun. 2007). The same applies in the following.) metal compound (e.g., lithium methanolate, lithium ethanolate, lithium propanolato, lithium butanolato, sodium methanolate, potassium-tert-butanolato, etc.), a second group metal compound (e.g., magnesium methanolate, calcium methanolate, etc.), a third group metal compound (e.g., cerium (IV) oxide, uranyl acetate, etc.), a fourth group metal compound (titaniumtetraisopropanolato, titaniumtetrabutanolato, titanium tetrachloride, titaniumtetraphenolate, titanium naphthate, etc.), a fifth group metal compound (e.g., vanadium (III) chloride, vanadium acetylacetonate, etc.), a sixth group metal compound (e.g., chromium (III) chloride, molybdenum (VI) oxide, molybdenum acetyl acetonate, tungsten (VI) oxide, etc.), a seventh group metal compound (e.g., manganese (II) chloride, manganese (II) acetate, manganese (III) acetate, etc.), an eighth group metal compound (e.g., iron (II) acetate, iron (III) acetate, iron phosphate, iron oxalate, ferric (III) chloride, iron (III) bromide, etc.), a ninth group metal compound (e.g., cobalt acetate, cobalt chloride, cobalt sulfurate, cobalt naphthenate, etc.), a tenth group metal compound (e.g., nickel chloride, nickel acetate, nickel naphthenate, etc.), an eleventh group metal compound (e.g., copper (II) acetate, copper (II) sulfate, copper (II) nitrate, bis-(triphenyl-phosphineoxide)-copper (II) chroride, copper molybdate, silver acetate, gold acetate, etc.), a twelfth group metal compound (e.g., zinc oxide, zinc chloride, zinc acetate, zinc acetonyl acetate, zinc octanoate, zinc oxalate, zinc hexylate, zinc benzoate, zinc undecylate, etc.), a thirteen group metal compound (e.g., aluminum acetyl acetonate, aluminum-isobutyrate, aluminum trichloride, etc.), a fourteen group metal compound (e.g., tin (II) chloride, tin (IV) chloride, lead acetate, lead phosphate, etc.), and a fifteenth group metal compound (e.g., antimony (III) chloride, antimony (V) chloride, bismuth (III) chloride, etc.).

Examples of catalysts also include $Zn(OSO_2CF_3)_2$ (also indicated as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

These catalysts may be used singly or in combination of two or more.

The blending amount of the catalyst relative to 1 mol of pentamethylenediamine is, for example, 0.000001 to 0.1 mol, preferably, 0.00005 to 0.05 mol. When the blending amount of the catalyst is more than such a range, no additional significant reaction facilitating effects can be seen, and at the same time, the increase in the blending amount may increase costs. On the other hand, when the blending amount is smaller than such a range, reaction facilitating effects may not be obtained.

The catalyst may be added all at once, continuously, or dividedly and intermittently several times, any of which does not affect reaction activity, and is not limited.

In this reaction, the reaction solvent is not necessarily needed, but when the reaction materials are solid, or when reaction product deposits, for example, a solvent may be blended, which improves handleability.

Examples of solvents is not particularly limited as long as the solvent is inactive or low in reactivity relative to the reaction materials, i.e., pentamethylenediamine, urea and/or N-non-substitute carbamate, and alcohol, and to the reaction product, i.e., a urethane compound, and examples thereof include aliphatic hydrocarbons (e.g., hexane, pentane, petroleum ether, ligroin, cyclododecane, decalin, etc.), aromatic hydrocarbons (e.g., benzene, toluene, xylene, ethylbenzene, isopropylbenzene, butylbenzene, cyclohexylbenzene, tetralin, chlorobenzene, o-dichlorobenzene, methylnaphthalene, chloronaphthalene, dibenzyltoluene, triphenylmethane, phenylnaphthalene, biphenyl, diethylbiphenyl, triethylbiphenyl, etc.), ethers (e.g., diethylether, diisopropylether, dibutylether, anisole, diphenylether, tetrahydrofuran, ethylene glycol dimethyl ether, ethylene glycol diethyl ether, ethylene glycol dibutyl ether, diethylene glycol dimethyl ether, diethylene glycol diethyl ether, etc.), carbonates (e.g., dimethylcarbonate, diethylcarbonate, dipropylcarbonate, dibutylcarbonate, etc.), nitriles (e.g., acetonitrile, propionitrile, adiponitrile, benzonitrile, etc.), aliphatic halogenated hydrocarbons (e.g., methylene chloride, chloroform, 1,2-dichloroethane, 1,2-dichloropropane, 1,4-dichlorobutane, etc.), amides (e.g., dimethylformamide, dimethylacetamide, etc.), nitro compounds (e.g., nitromethane, nitrobenzene, etc.), N-methyl pyrrolidinone, N,N-dimethylimidazolidinone, and dimethyl sulfoxide.

Examples of reaction solvents further include the extractants in the above-described extraction.

Of these reaction solvents, in view of economy, and handleability, etc., aliphatic hydrocarbons and aromatic hydrocarbons are used preferably.

Examples of reaction solvents also include, preferably, the extractants in the above-described extraction.

By using the extractant as the reaction solvent, the extracted pentamethylene diisocyanate can be used as is in the carbamation reaction, achieving an improvement in handleability.

Such a reaction solvent may be used singly or in combination of two or more.

The blending amount of the reaction solvent is not particularly limited as long as the amount is an amount that allows the target product, i.e., pentamethylene dicarbamate to dissolve. However, the blending amount of the reaction solvent is preferably small as much as possible because of the following reasons: industrially, the reaction solvent has to be collected from the reaction liquid, and therefore the energy consumed for the collection is to be decreased as much as possible, and also when the blending amount is large, the reaction substrate concentration is decreased and the reaction velocity is decreased. To be more specific, the blending amount of the reaction solvent relative to 1 part by mass of pentamethylenediamine is, usually, in the range of 0.1 to 500 parts by mass, preferably 1 to 100 parts by mass.

In this reaction, the reaction temperature is suitably selected in the range of, for example, 100 to 350° C., preferably 150 to 300° C. When the reaction temperature is lower than the range, the reaction velocity may decrease, and when the reaction temperature is higher than the range, side reaction may increase and the yield of the target product, pentamethylene dicarbamate may decrease.

The reaction pressure is usually atmospheric pressure, but when the boiling point of components in the reaction liquid is lower than the reaction temperature, the pressure may be increased, or as necessary, decreased.

The reaction time is, for example, 0.1 to 20 hours, preferably 0.5 to 10 hours. When the reaction time is shorter than such a range, the yield of the target product, i.e., pentamethylene dicarbamate may decrease. On the other hand, the reaction time longer than such a range is inappropriate in view of industrial production.

In the reaction, with the above-described conditions, for example, the reaction vessel is charged with pentamethylenediamine, urea and/or N-non-substitute carbamate, alcohol, and as necessary, a catalyst, and a reaction solvent, and the mixture is stirred or mixed. Then, under mild conditions, pentamethylene dicarbamate is produced in a short period of time for low costs and at high yield.

The obtained pentamethylene dicarbamate corresponds to the above-described pentamethylenediamine, which is usually used as a material component, to be more specific, 1,5-pentamethylene dicarbamate is obtained.

In this reaction, ammonia is produced as a by-product.

In this reaction, when N-non-substitute carbamate is blended, and alcohol corresponding to its ester is produced as a by-product.

In this reaction, the reaction type can be any of batch processing and continuous processing.

In this reaction, preferably, reaction is conducted while ammonia produced as a by-product is discharged. Furthermore, when N-non-substitute carbamate is blended, reaction is conducted while discharging the alcohol produced as a by-product.

In this manner, production of the target product, i.e., pentamethylene dicarbamate is facilitated, and the yield can be further increased.

When the obtained pentamethylene dicarbamate is isolated, for example, pentamethylene dicarbamate may be separated from the reaction liquid including excessive (unreacted) urea and/or N-non-substitute carbamate, excessive (unreacted) alcohol, catalyst, pentamethylene dicarbamate, reaction solvent, ammonia produced as a by-product, alcohol produced as a by-product depending on the case, by a known separation refining method.

Then, in the method of producing pentamethylene diisocyanate, the obtained pentamethylene dicarbamate is thermally decomposed, thereby producing pentamethylene diisocyanate.

That is, in such a method of producing isocyanate, the obtained pentamethylene dicarbamate as described above is thermally decomposed, thus producing pentamethylene diisocyanate, and alcohol as a by-product.

The obtained pentamethylene diisocyanate corresponds to the above-described pentamethylenediamine, which is usually used as the material component, to be more specific, 1,5-pentamethylene diisocyanate is obtained.

As the alcohol, usually, alcohol that is the same type with the alcohol used as the material component is produced as a by-product.

The thermal decomposition is not particularly limited, for example, and a known decomposition method such as liquid phase method and gas phase method may be used.

In the gas phase method, pentamethylene diisocyanate and alcohol produced by thermal decomposition can be separated from the gaseous product mixture by fractional condensation. In the liquid phase method, pentamethylene diisocyanate and alcohol produced by thermal decomposition can be separated, for example, by distillation, or by using a solvent and/or an inactive gas as a support substance.

As the thermal decomposition, preferably, in view of workability, liquid phase method is used.

The thermal decomposition reaction of pentamethylene dicarbamate in the liquid phase method is reversible reaction, and thus preferably, in order to suppress reverse reaction (urethane reaction between pentamethylene diisocyanate and alcohol) of thermal decomposition reaction, pentamethylene dicarbamate is subjected to thermal decomposition, and at the same time, pentamethylene diisocyanate, and/or alcohol produced as a by-product are, for example, discharged as gases from the reaction mixture, and then these are separated.

Reaction conditions of thermal decomposition reaction are as follows: preferably, pentamethylene dicarbamate is excellently thermally decomposed; pentamethylene diisocyanate and alcohol produced in the thermal decomposition are evaporated, thereby avoiding equilibrium state of pentamethylene dicarbamate and pentamethylene diisocyanate; and further suppressing side reactions such as polymerization of pentamethylene diisocyanate.

As such reaction conditions, to be more specific, the thermal decomposition temperature is usually 350° C. or less, preferably 80 to 350° C., more preferably, 100 to 300° C. When the thermal decomposition temperature is lower than 80° C., a practical reaction velocity may not be achieved, and when the thermal decomposition temperature is more than 350° C., unfavorable side reactions such as polymerization of pentamethylene diisocyanate may be caused. The pressure at the time of thermal decomposition reaction is preferably a pressure that allows the produced alcohol to be evaporated relative to the above-described thermal decomposition reaction temperature, and in view of equipment and application, practically, preferably is 0.133 to 90 kPa.

Pentamethylene dicarbamate used in the thermal decomposition may be purified one. Alternatively, using a crude material of pentamethylene dicarbamate obtained by collecting excessive (unreacted) urea and/or N-non-substitute carbamate, excessive (unreacted) alcohol, catalyst, reaction solvent, ammonia produced as a by-product, and alcohol produced as a by-product depending on the case after the termination of the above-described reaction (that is, reaction between pentamethylenediamine, urea and/or N-non-substitute carbamate, and alcohol) and separating it therefrom, the thermal decomposition may be conducted afterwards.

Furthermore, as necessary, a catalyst and an inactive solvent may be added. These catalyst and inactive solvent may be added, although depending on the types of these, at any of the time of above-described reaction, before and after the distillation separation after the reaction, and before and after the separation of pentamethylene dicarbamate.

As the catalyst used in the thermal decomposition, one or more metal substance selected from Sn, Sb, Fe, Co, Ni, Cu, Zn, Cr, Ti, Pb, Mo, and Mn; or a metal compound such as oxide, halide, carboxylate, phosphate, and an organic metal compound of these used in urethane reaction between isocyanate and hydroxyl groups is used. Of these examples of catalysts, because Fe, Sn, Co, Sb, and Mn exhibit effects of suppressing by-products, they are preferably used.

Examples of metal catalysts of Sn include tin oxide, tin chloride, tin bromide, tin iodide, tin formate, tin acetate, tin oxalate, tin octylate, tin stearate, tin oleate, tin phosphate, dibutyltin dichloride, dibutyltin dilaurate, and 1,1,3,3-tetrabutyl-1,3-dilauryloxydistannoxane.

Examples of metal catalysts of Fe, Co, Sb, and Mn include acetate, benzoate, naphthenate, and acetylacetonato salt thereof The blending amount of the catalyst (metal substance or a compound thereof) relative to the reaction liquid is in the range of 0.0001 to 5 mass %, preferably in the range of 0.001 to 1 mass %.

The inactive solvent is not particularly limited, as long as the inactive solvent at least dissolves pentamethylene dicarbamate, is inactive relative to pentamethylene dicarbamate and isocyanate, and is stable at the temperature of thermal decomposition. However, to perform thermal decomposition reaction efficiently, its boiling point is preferably higher than that of the produced isocyanate. Examples of inactive solvents include esters such as dioctyl phthalate, didecyl phthalate, and didodecyl phthalate; and aromatic hydrocarbons and aliphatic hydrocarbons usually used as a heating medium such as dibenzyltoluene, triphenylmethane, phenylnaphthalene, biphenyl, diethylbiphenyl, and triethylbiphenyl.

The inactive solvent can also be obtained from commercially available products, and examples thereof include Barrel process oil B-01 (aromatic hydrocarbons, boiling point: 176° C.), Barrel process oil B-03 (aromatic hydrocarbons, boiling point: 280° C.), Barrel process oil B-04AB (aromatic hydrocarbons, boiling point: 294° C.), Barrel process oil B-05 (aromatic hydrocarbons, boiling point:

302° C.), Barrel process oil B-27 (aromatic hydrocarbons, boiling point: 380° C.), Barrel process oil B-28AN (aromatic hydrocarbons, boiling point: 430° C.), Barrel process oil B-30 (aromatic hydrocarbons, boiling point: 380° C.), Barrel therm 200 (aromatic hydrocarbons, boiling point: 382° C.), Barrel therm 300 (aromatic hydrocarbons, boiling point: 344° C.), Barrel therm 400 (aromatic hydrocarbons, boiling point: 390° C.), Barrel therm 1H (aromatic hydrocarbons, boiling point: 215° C.), Barrel therm 2H (aromatic hydrocarbons, boiling point: 294° C.), Barrel therm 350 (aromatic hydrocarbons, boiling point: 302° C.), Barrel therm 470 (aromatic hydrocarbons, boiling point: 310° C.), Barrel therm PA (aromatic hydrocarbons, boiling point: 176° C.), Barrel therm 330 (aromatic hydrocarbons, boiling point: 257° C.), Barrel therm 430 (aromatic hydrocarbons, boiling point: 291° C.), (all manufactured by Matsumura Oil Co., Ltd.), NeoSK-OIL1400 (aromatic hydrocarbons, boiling point: 391° C.), NeoSK-OIL1300 (aromatic hydrocarbons, boiling point: 291° C.), NeoSK-OIL330 (aromatic hydrocarbons, boiling point: 331° C.), NeoSK-OIL170 (aromatic hydrocarbons, boiling point: 176° C.), NeoSK-OIL240 (aromatic hydrocarbons, boiling point: 244° C.), KSK-OIL260 (aromatic hydrocarbons, boiling point: 266° C.), and KSK-OIL280 (aromatic hydrocarbons, boiling point: 303° C.), (all manufactured by Soken Technix's).

The blending amount of the inactive solvent relative to 1 part by mass of pentamethylene dicarbamate is in the rage of 0.001 to 100 parts by mass, preferably 0.01 to 80 parts by mass, more preferably 0.1 to 50 parts by mass.

The thermal decomposition reaction can be conducted in any of the batch reaction, in which pentamethylene dicarbamate, a catalyst, and an inactive solvent are charged at once, and the continuous reaction, in which pentamethylene dicarbamate is charged in an inactive solvent containing a catalyst under reduced pressure.

In the thermal decomposition, pentamethylene diisocyanate and alcohol are produced, and at the same time, for example, allophanate, amines, urea, carbonate, carbamate, carbon dioxide, etc. may be produced by side reaction, and therefore as necessary, the obtained pentamethylene diisocyanate is refined by a known method.

As the carbamation method, although not to be described in detail, in addition to the above-described urea method, a known carbonation method is also used: that is, a method in which pentamethylene diisocyanate is obtained by synthesizing pentamethylene dicarbamate from pentamethylenediamine, and dialkyl carbonate or diary' carbonate, and thermally decomposing the pentamethylene dicarbamate in the same manner as described above.

The purity of the thus obtained pentamethylene diisocyanate of the present invention is, for example, 95 to 100 mass %, preferably 97 to 100 mass %, more preferably 98 to 100 mass %, particularly preferably 99 to 100 mass %, most preferably 99.5 to 100 mass %.

To pentamethylene diisocyanate, for example, a stabilizer can also be added.

Examples of stabilizers include antioxidants, acid compounds, compounds containing sulfonamide groups, and organic phosphite.

Examples of antioxidants include hindered phenolic antioxidants, and specific examples include 2,6-di(t-butyl)-4-methylphenol, 2,4,6-tri-t-butylphenol, 2,2'-methylenebis-(4-methyl-6-t-butylphenol), 2,2'-thio-bis-(4-methyl-6-t-butylphenol), 4,4'-thio-bis(3-methyl-6-t-butylphenol), 4,4'-butylidene-bis-(6-t-butyl-3-methylphenol), 4,4'-methylidyne-bis-(2,6-di-t-butylphenol), 2,2'-methylene-bis-[4-methyl-6-(1-methylcyclohexyl)-phenol], tetrakis-[methylene-3-(3,5-di-t-butyl-4-hydroxyphenyl)-propionyl]-methane, 1,3,5-trimethyl-2,4,6-tris-(3,5-di-t-butyl-4-hydroxyphenyl)-propionyl-methane, 1,3,5-trimethyl-2,4,6-tris-(3,5-di-t-butyl-4-hydroxybenzyl)-benzene, N,N'-hexamethylene-bis-(3,5-di-t-butyl-4-hydroxyhydrocinnamic acid amide, 1,3,5-tris-(3,5-di-t-butyl-4-hydroxybenzyl)-isocyanurate, 1,1,3-tris-(5-t-butyl-4-hydroxy-2-methylphenyl)-butane, 1,3,5-tris-(3,5-di-t-butyl-4-hydroxybenzyl)-mesitylene, ethylene glycol-bis-[3,3-bis-(3'-t-butyl-4'-hydroxyphenyl)-butyrate, 2,2'-thiodiethyl-bis-3-(3,5-di-t-butyl-4-hydroxyphenyl)-propionate, di-(3-t-butyl-4'-hydroxy-5-methylphenyl)-dicyclopentadiene, 2,2'-methylene-bis-(4-methyl-6-cyclohexylphenol), 1,6-hexanediol-bis-(3,5-di-t-butyl-4-hydroxyphenyl)-propionate, 2,4-bis-(n-octylthio)-6-(4-hydroxy-3,5-di-t-butylanilino)-1,3,5-triazine, diethyl-3,5-di-t-butyl-4-hydroxybenzylphosphonate, triethylene glycol-bis-3-(t-butyl-4-hydroxy-5-methylphenyl)-propionate, and also include, for example, IRGANOX® 1010, IRGANOX® 1076, IRGANOX® 1098, IRGANOX® 1135, IRGANOX® 1726, IRGANOX® 245, IRGANOX® 3114, and IRGANOX® 3790 (all manufactured by BASF Japan Ltd., trade name).

These antioxidants may be used singly or in combination of two or more.

Examples of acid compounds include organic acid compounds, to be specific, phosphate, phosphite, hypophosphite, formic acid, acetic acid, propionic acid, hydroxyacetic acid, oxalic acid, lactic acid, citric acid, malic acid, sulfonic acid, sulfonate, phenol, enol, imide, and oxime.

These acid compounds may be used singly or in combination of two or more.

Examples of compounds containing sulfonamide groups include aromatic sulfonamides and aliphatic sulfonamides.

Examples of aromatic sulfonamides include benzene sulfonamide, dimethylbenzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethylethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in combination of two or more.

Examples of organic phosphites include organic diester phosphonate, and organic triester phosphonate, to be more specific, for example, monophosphites such as triethyl phosphite, tributyl phosphite, tris (2-ethylhexyl) phosphite, tridecyl phosphite, trilauryl phosphite, tris (tridecyl) phosphite, tristearyl phosphite, triphenyl phosphite, tris (nonylphenyl) phosphite, tris (2,4-di-t-butylphenyl) phosphite, diphenyldecyl phosphite, and diphenyl (tridecyl) phosphite; di, tri, or tetra phosphites derived from polyhydric alcohol such as distearyl•pentaerythrityl•diphosphite, di•dodecyl•pentaerythritol•diphosphite, di•tridecyl•pentaerythritol•diphosphite, dinonylphenyl•pentaerythritol•diphosphite, tetraphenyl•tetra•tridecyl•pentaerythrityl•tetra phosphite, tetraphenyl•dipropylene glycol•diphosphite, and tripentaerythritol•tri phosphite; and diphosphites derived from bisphenol compounds such as di•alkyl•bisphenol A•diphosphite having 1 to 20 carbons, and 4,4'-butylidene-bis(3-methyl-6-t-butylphenyl-di•tridecyl) phosphite; poly phosphites such as hydrogenated bisphenol A phosphite polymers (molecular weight 2400 to 3000); and tris (2,3-dichloropropyl) phosphate.

These organic phosphites may be used singly or in combination of two or more.

As the stabilizer, preferably, antioxidants, acid compounds, or a compound containing a sulfonamide group is used. More preferably, to pentamethylene diisocyanate, an antioxidant and an acid compound and/or a compound containing a sulfonamide group are blended so that pentamethylene diisocyanate contains these.

By adding these stabilizers, improvement in storage stability of an isocyanate modified substance (described later) obtained by using the pentamethylene diisocyanate can be achieved.

The mixing ratio of the stabilizer is not particularly limited, and is appropriately selected according to necessity and its application.

The mixing ratio of the antioxidant relative to 100 parts by mass of the pentamethylene diisocyanate is, to be specific, for example, 0.0005 to 0.05 parts by mass.

The mixing ratio of the acid compound and/or the compound containing a sulfonamide group (when used in combination, a total of these) relative to 100 parts by mass of pentamethylene diisocyanate is, for example, 0.0005 to 0.02 parts by mass.

In the present invention, a polyisocyanate composition is further contained.

The polyisocyanate composition is obtained, to be more specific, by modifying pentamethylene diisocyanate, and contains at least one of the functional group of (a) to (e) below.

(a) an isocyanurate group,
(b) an allophanate group,
(c) a biuret group,
(d) a urethane group, and
(e) a urea group.

The polyisocyanate composition containing the above-described functional group of (a) (isocyanurate group) is a trimer of pentamethylene diisocyanate, and for example, can be obtained by allowing pentamethylene diisocyanate to react in the presence of a known isocyanurate-forming catalyst, thereby allowing trimerization.

The polyisocyanate composition containing the above-described functional group of (b)(allophanate group) is an allophanate-modified substance of pentamethylene diisocyanate, and for example, can be obtained by allowing pentamethylene diisocyanate and a monoalcohol to react, and then further allowing them to react in the presence of a known allophanate-forming catalyst.

The polyisocyanate composition containing the above-described functional group of (c) (biuret group) is a biuret-modified substance of pentamethylene diisocyanate, and for example, can be obtained by allowing pentamethylene diisocyanate to react with, for example, water, tertiary alcohol (e.g., t-butylalcohol, etc.), or secondary amine (e.g., dimethylamine, diethylamine, etc.), and then further allowing them to react in the presence of a known biuretizing catalyst.

The polyisocyanate composition containing the above-described functional group of (d) (urethane group) is a polyol modified substance of pentamethylene diisocyanate, and can be obtained, for example, by reaction between pentamethylene diisocyanate and a polyol component (e.g., trimethylolpropane, etc. described later in detail).

The polyisocyanate composition containing the above-described functional group of (e) (urea group) is a polyamine modified substance of pentamethylene diisocyanate, and can be obtained, for example, by reaction between pentamethylene diisocyanate, and water, or a polyamine component (described later).

The polyisocyanate composition containing at least one of the functional groups of the above-described (a) to (e) is sufficient, and can contain two or more of the functional groups of the above-described (a) to (e). Such a polyisocyanate composition is produced by suitably combining the above-described reactions.

As the polyisocyanate composition, preferably, a trimer (polyisocyanate composition containing an isocyanurate group) of pentamethylene diisocyanate is used.

Trimer of pentamethylene diisocyanate further includes polyisocyanate having an iminooxadiazinedione group other than the isocyanurate group.

The polyurethane resin of the present invention can be obtained by allowing the above-described pentamethylene diisocyanate, and/or the above-described polyisocyanate composition, and an active hydrogen compound to react with each other.

Examples of active hydrogen compounds include a polyol component (component containing mainly polyol having two or more hydroxyl groups), and a polyamine component (compound containing mainly polyamine having two or more amino groups).

Examples of polyol component in the present invention include low-molecular-weight polyols and high-molecular weight polyols.

Low-molecular-weight polyols are compounds having two or more hydroxyl groups and a number average molecular weight of below 400, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, 3-methyl-1,5-pentanediol, 2,2,2-trimethyl-pentanediol, 3,3-dimethylolheptane, alkane (C7 to 20) diol, 1,3- or 1,4-cyclohexanedimethanol and a mixture thereof, 1,3- or 1,4-cyclohexanediol and a mixture thereof, hydrogenated bisphenol A, 1,4-dihydroxy-2-butene, 2,6-dimethyl-1-octene-3,8-diol, bisphenol A, diethylene glycol, triethylene glycol, and dipropylene glycol; trihydric alcohols such as glycerin, and trimethylolpropane; tetrahydric alcohols such as tetramethylolmethane (pentaerythritol), and diglycerol; pentahydric alcohol such as xylitol; hexahydric alcohols such as sorbitol, mannitol, allitol, iditol, dulcitol, altritol, inositol, and dipentaerythritol; heptahydric alcohol such as perseitol; and octahydric alcohols such as sucrose.

These low-molecular-weight polyols may be used singly or in combination of two or more.

High-molecular weight polyols are compounds having two or more hydroxyl groups and having a number average molecular weight of 400 or more, and examples thereof include polyetherpolyol, polyester polyol, polycarbonate polyol, polyurethane polyol, epoxy polyol, vegetable oil polyol, polyolefin polyol, acrylic polyol, and vinyl monomer-modified polyol.

Examples of polyether polyols include polypropylene glycol, and polytetramethylene ether glycol.

Examples of polypropylene glycols include addition polymerized product (including random and/or block copolymer of two or more alkylene oxides) of alkylene oxides such as ethylene oxide and propylene oxide using the above-described low-molecular-weight polyol or the aromatic/aliphatic polyamine as an initiator.

Examples of polytetramethylene ether glycols include ring-opening polymerized product obtained by cation polymerization of tetrahydrofuran, and noncrystalline polytetramethylene ether glycol obtained by copolymerizing polymerization unit of tetrahydrofuran and the above-described dihydric alcohol.

Examples of polyester polyols include a polycondensation product obtained by allowing the above-described low-molecular-weight polyol and polybasic acid to react under known conditions.

Examples of polybasic acids include saturated aliphatic dicarboxylic acids (C11 to 13) such as oxalic acid, malonic acid, succinic acid, methylsuccinic acid, glutaric acid, adipic acid, 1,1-dimethyl-1,3-dicarboxypropane, 3-methyl-3-ethylglutaric acid, azelaic acid, sebacic acid, etc.; unsaturated aliphatic dicarboxylic acids such as maleic acid, fumaric acid, itaconic acid, etc.; aromatic dicarboxylic acids such as orthophthalic acid, isophthalic acid, terephthalic acid, toluenedicarboxylic acid, naphthalenedicarboxylic acid, etc.; alicyclic dicarboxylic acids such as hexahydrophthalic acid, etc.; other carboxylic acids such as dimer acid, hydrogenated dimer acid, het acid, etc. and acid anhydrides derived from these carboxylic acids such as oxalic anhydride, succinic anhydride, maleic anhydride, phthalic anhydride, 2-alkyl (C12 to C18) succinic anhydride, tetrahydrophthalic anhydride, trimellitic anhydride, and hallides derived from these carboxylic acids such as oxalyl dichloride, adipoyl dichloride, and sebacoyl dichloride.

Examples of polyester polyols include plants derived polyester polyol, to be specific, vegetable oil polyester polyols obtained by condensation reaction of hydroxycarboxylic acid such as hydroxyl group-containing vegetable oil fatty acid (e.g., castor oil fatty acid containing ricinoleic acid, hydrogenated castor oil fatty acid containing 12-hydroxystearic acid, etc.) using the above-described low-molecular-weight polyol as an initiator under known conditions.

Examples of polyester polyols include polycaprolactone polyol, and polyvalerolactone polyol obtained by ring-opening polymerization of lactones such as ε-caprolactone, γ-valerolactone, etc. and lactides such as L-lactide, D-lactide using the above-described low-molecular-weight polyols (preferably, dihydric alcohol) as an initiator; and further lactone-based polyester polyols obtained by copolymerizing such a polycaprolactone polyol or polyvalerolactone polyol with the above-described dihydric alcohol.

Examples of polycarbonate polyols include ring-opening polymerization product of ethylene carbonate using the above-described low-molecular-weight polyols (preferably, dihydric alcohol) as an initiator, and noncrystalline polycarbonate polyols obtained by copolymerization of dihydric alcohols such as 1,4-butanediol, 1,5-pentanediol, 3-methyl-L5-pentanediol, and 1,6-hexanediol with ring-opening polymerization product.

Polyurethane polyols can be obtained as polyester polyurethane polyol, polyether polyurethane polyol, polycarbonate polyurethane polyol, or polyester polyether polyurethane polyol, by allowing polyester polyol, polyetherpolyol and/or polycarbonate polyol obtained as described above to react with polyisocyanate at an equivalent ratio (OH/NCO) of hydroxyl group (OH) to isocyanate group (NCO) of more than 1.

Examples of epoxy polyols include epoxy polyols obtained by reaction of the above-described low-molecular-weight polyols with polyfunctional halohydrin such as epichlorohydrin, β-methylepichlorohydrin, etc.

Examples of vegetable oil polyols include hydroxyl group-containing vegetable oil such as castor oil, palm oil, etc. Examples thereof include ester-modified castor oil polyol obtained by reaction of castor oil polyol or castor oil fatty acid with polypropylene polyol.

Examples of polyolefin polyols include polybutadiene polyol, and a partially saponified ethylene-vinyl acetate copolymer.

Examples of acrylic polyol include copolymers obtained by copolymerizing hydroxyl group-containing acrylate with a copolymerizable vinyl monomer that is copolymerizable with hydroxyl group-containing acrylate.

Examples of hydroxyl group-containing acrylates include 2-hydroxyethyl (meth)acrylate, hydroxypropyl (meth)acrylate, hydroxybutyl (meth)acrylate, 2,2-dihydroxymethylbutyl (meth)acrylate, polyhydroxyalkylmaleate, and polyhydroxyalkylfumarate. Preferably, 2-hydroxyethyl (meth) acrylate is used.

Examples of copolymerizable vinyl monomers include alkyl (meth)acrylate (1 to 12 carbon atoms) such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, isopentyl (meth)acrylate, hexyl (meth)acrylate, isononyl (meth)acrylate, 2-ethylhexyl (meth)acrylate, and cyclohexylacrylate; aromatic vinyls such as styrene, vinyltoluene, and α-methylstyrene; vinyl cyanide such as (meth) acrylonitrile; vinyl monomers containing carboxyl groups such as (meth) acrylic acid, fumaric acid, maleic acid, and itaconic acid or their alkyl esters; alkanepolyol poly (meth)acrylate such as ethylene glycol di(meth)acrylate, butyleneglycol di(meth)acrylate, hexanediol di(meth)acrylate, oligoethylene glycol di(meth)acrylate, trimethylolpropane di(meth)acrylate, and trimethylolpropane tri (meth)acrylate; and vinyl monomers containing isocyanate groups such as 3-(2-isocyanato-2-propyl)-α-methylstyrene.

Acrylic polyol can be obtained by copolymerizing these hydroxyl group-containing acrylate, and copolymerizable vinyl monomers in the presence of an appropriate solvent and a polymerization initiator.

Examples of acrylic polyol include silicone polyol and fluorine polyol.

Examples of silicone polyols include acrylic polyol in which as the copolymerizable vinyl monomer, for example, a silicone compound containing a vinyl group such as γ-methacryloxypropyltrimethoxysilane is blended in the above-described copolymerization of acrylic polyol.

Examples of fluorine polyols include acrylic polyol in which as the copolymerizable vinyl monomer, for example, a fluorine compound containing a vinyl group such as tetrafluoroethylene, or chlorotrifluoroethylene is blended in the above-described copolymerization of acrylic polyol.

The vinyl monomer-modified polyol can be obtained by allowing the above-described high-molecular weight polyol to react with a vinyl monomer.

As the high-molecular weight polyol, preferably, a high-molecular weight polyol selected from polyetherpolyol, polyester polyol, and polycarbonate polyol is used.

Examples of vinyl monomers include the above-described alkyl (meth) acrylate, vinyl cyanide, and vinylidene cyanide. These vinyl monomers may be used singly or in combination of two or more. Of these vinyl monomers, preferably, alkyl (meth) acrylate is used.

The vinyl monomer-modified polyol can be obtained by allowing these high-molecular weight polyols to react with vinyl monomers in the presence of, for example, a radical polymerization initiator (e.g., persulfate, organic peroxide, azo compound, etc.).

These high-molecular weight polyols may be used singly or in combination of two or more.

As the high-molecular weight polyol, preferably, polyester polyol, or acrylic polyol is used, more preferably, polyester polyol is used, even more preferably, plant derived polyester polyol is used.

These polyol components may be used singly or in combination of two or more.

Examples of polyamine components include aromatic polyamine, aralkyl polyamine, alicyclic polyamine, aliphatic polyamine, amino alcohol, an alkoxysilyl compound having a primary amino group, or a primary amino group and a secondary amino group, and polyoxyethylene group-containing polyamine.

Examples of aromatic polyamines include 4,4'-diphenylmethanediamine, and tolylenediamine.

Examples of aralkyl polyamine include 1,3- or 1,4-xylylene diamine and mixtures thereof.

Examples of alicyclic polyamines include 3-aminomethyl-3,5,5-trimethylcyclohexylamine (also called: isophoronediamine), 4,4'-dicyclohexylmethanediamine, 2,5 (2,6)-bis(aminomethyl) bicyclo[2.2.1]heptane, 1,4-cyclohexanediamine, 1-amino-3-aminomethyl-3,5,5-trimethylcyclohexane, bis-(4-aminocyclohexyl) methane, diaminocyclohexane, 3,9-bis(3-aminopropyl)-2,4,8,10-tetraoxaspiro [5.5]undecane, 1,3- and 1,4-bis(aminomethyl) cyclohexane and mixtures thereof.

Examples of aliphatic polyamines include ethylene diamine, propylene diamine, 1,3-propane diamine, 1,4-butanediamine, 1,5-pentanediamine, 1,6-hexamethylenediamine, hydrazine (including hydrate), diethylenetriamine, triethylenetetramine, tetraethylenepentamine, 1,2-diaminoethane, 1,2-diaminopropane, and 1,3-diaminopentane.

Examples of aminoalcohol include N-(2-aminoethyl) ethanolamine.

Examples of alkoxysilyl compound having a primary amino group, or a primary amino group and a secondary amino group include alkoxysilyl group-containing monoamine such as γ-aminopropyltriethoxysilane, and N-phenyl-γ-aminopropyltrimethoxysilane; N-β (aminoethyl) γ-aminopropyltrimethoxysilane; and N-β (aminoethyl) γ-aminopropylmethyldimethoxysilane.

Examples of polyoxyethylene group-containing polyamines include polyoxyalkylene ether diamine such as polyoxyethylene ether diamine. To be more specific, examples thereof include PEG#1000 diamine manufactured by NOF Corporation, Jeffamine® ED-2003, EDR-148, and XTJ-512 manufactured by Huntsman Inc.

These polyamine components may be used singly or in combination of two or more.

In the present invention, as necessary, known additives, for example, plasticizers, antiblocking agents, heat-resistant stabilizers, light-resistant stabilizer, antioxidants, release agents, catalysts, as well as pigments, dyes, lubricants, fillers, and hydrolysis inhibitor may be added. These additives may be added at the time of synthesizing components, or may be added at the time of mixing and dissolving components, or may be added after the synthesis.

The polyurethane resin of the present invention can be produced, for example, by polymerization methods such as bulk polymerization and solution polymerization.

In bulk polymerization, for example, under a nitrogen stream, while stirring pentamethylene diisocyanate and/or polyisocyanate composition, an active hydrogen compound is added thereto, and the mixture is allowed to react at a reaction temperature of 50 to 250° C., more preferably at 50 to 200° C., for about 0.5 to 15 hours.

In solution polymerization, pentamethylene diisocyanate and/or polyisocyanate composition, and an active hydrogen compound are added to an organic solvent, and the mixture is allowed to react at a reaction temperature of 50 to 120° C., more preferably at 50 to 100° C., for about 0.5 to 15 hours.

Examples of organic solvents include ketones such as acetone, methyl ethyl ketone, methylisobutylketone, and cyclohexanone; nitriles such as acetonitrile; alkyl esters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol ether esters such as methyl cellosolve acetate, ethyl cellosolve acetate, methyl carbitol acetate, ethyl carbitol acetate, ethylene glycol ethylether acetate, propylene glycol methylether acetate, 3-methyl-3-methoxybutyl acetate, and ethyl-3-ethoxypropionate; ethers such as diethylether, tetrahydrofuran, and dioxane; halogenated aliphatic hydrocarbons such as methyl chloride, methylene chloride, chloroform, carbon tetrachloride, methyl bromide, methylene iodide, and dichloroethane; polar aprotic solvents such as N-methyl pyrrolidone, dimethylformamide, N,N'-dimethylacetamide, dimethyl sulfoxide, and hexamethyl phosphoramide.

Examples of organic solvents also include nonpolar solvents (nonpolar organic solvents), and examples of nonpolar solvents include those nonpolar organic solvents having an aniline point of, for example, 10 to 70° C., preferably 12 to 65° C. and having low toxicity and solvency, such as aliphatic, naphthene hydrocarbon organic solvent; and vegetable oils typically represented by turpentine oil.

The nonpolar organic solvents can be obtained from commercially available products, and examples of those commercially available products include petroleum hydrocarbon organic solvents such as HAWS® (manufactured by Shell Chemicals, aniline point 15° C.), SWASOL® 310 (manufactured by Maruzen Petrochemical, aniline point 16° C.), Esso Naphtha No. 6 (manufactured by Exxon Mobil Chemical, aniline point 43° C.), Laws (manufactured by Shell Chemicals, aniline point 43° C.), ESSO Naphtha No. 5 (manufactured by Exxon Mobil Corporation, aniline point 55° C.), and Pegasol™ 3040 (manufactured by Exxon Mobil Corporation, aniline point 55° C.); and also turpentine oils such as methylcyclohexane (aniline point 40° C.), ethylcyclohexane (aniline point 44° C.), and gum turpentine N (manufactured by YASUHARA CHEMICAL CO., LTD., aniline point 27° C.).

Furthermore, in the above-described polymerization reaction, as necessary, for example, a urethanizing catalyst can be added.

Examples of amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of organic metal compounds include organic tin compounds such as tin acetate, stannous octoate, stannous oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compound such as nickel naphthenate; organic cobalt compounds such as cobalt naphthenate; organic copper compounds such as copper octenate; organic bismuth compounds such as bismuth octylate and bismuth neodecanoate.

Examples of urethanizing catalysts also include potassium salts such as potassium carbonate, potassium acetate, and potassium octoate.

These urethanizing catalysts may be used singly or in combination of two or more.

In the above-described polymerization reaction, an (unreacted) pentamethylene diisocyanate and/or polyisocyanate composition can be removed, for example, by known removing methods such as distillation and extraction.

In bulk polymerization and solution polymerization, for example, pentamethylene diisocyanate and/or a polyisocyanate composition, and an active hydrogen compound are blended so that the equivalent ratio (NCO/active hydrogen group) of the isocyanate group in the pentamethylene diisocyanate and/or polyisocyanate composition relative to the active hydrogen group (hydroxyl group, amino group) in the active hydrogen compound is, for example, 0.75 to 1.3, preferably, 0.9 to 1.1.

When the above-described polymerization reaction is to be conducted more industrially, the polyurethane resin can be obtained by known methods such as, for example, one-shot method and prepolymer method according to its application. Also, the polyurethane resin can also be obtained by other methods, for example, as an aqueous dispersion (PUD).

In one-shot method, for example, pentamethylene diisocyanate and/or a polyisocyanate composition, and an active hydrogen compound are formulated (mixed) so that the equivalent ratio (NCO/active hydrogen group) of the isocyanate group in the pentamethylene diisocyanate and/or polyisocyanate composition relative to the active hydrogen group (hydroxyl group, amino group) in the active hydrogen compound is, for example, 0.75 to 1.3, preferably 0.9 to 1.1, and then thereafter, the mixture is allowed to react (curing reaction), for example, at room temperature to 250° C., preferably at room temperature to 200° C., for, for example, 5 minutes to 72 hours, preferably 4 to 24 hours. The curing temperature may be a constant temperature, or may be increased/decreased stepwise.

In prepolymer method, for example, first, pentamethylene diisocyanate and/or a polyisocyanate composition, and a portion of an active hydrogen compound (preferably, high-molecular weight polyol) are allowed to react, thereby synthesizing an isocyanate group-terminated prepolymer having isocyanate groups at its molecular terminals. Then, the obtained isocyanate group-terminated prepolymer is allowed to react with the remaining portion of the active hydrogen compound (preferably, low-molecular-weight polyol and/or polyamine component), thereby causing curing reaction. In the prepolymer method, the remaining portion of the active hydrogen compound is used as a chain extender.

To synthesize the isocyanate group-terminated prepolymer, pentamethylene diisocyanate and/or polyisocyanate composition, and a portion of the active hydrogen compound are formulated (mixed) so that the equivalent ratio (NCO/active hydrogen group) of the isocyanate group in the pentamethylene diisocyanate and/or polyisocyanate composition relative to the active hydrogen group in the portion of the active hydrogen compound is, for example, 1.1 to 20, preferably 1.3 to 10, more preferably 1.3 to 6, and then the mixture is allowed to react in the reaction vessel, for example, at room temperature to 150° C., preferably at 50 to 120° C., for, for example, 0.5 to 18 hours, preferably 2 to 10 hours. In this reaction, as necessary, the above-described urethanizing catalyst may be added, and after the completion of reaction, as necessary, the unreacted pentamethylene diisocyanate and/or polyisocyanate composition can be removed, for example, by a known removal method such as distillation or extraction.

Then, to cause the reaction between the obtained isocyanate group-terminated prepolymer and the remaining portion of the active hydrogen compound, the isocyanate group-terminated prepolymer and the remaining portion of the active hydrogen compound are formulated (mixed) so that the equivalent ratio (NCO/active hydrogen group) of the isocyanate group in the isocyanate group-terminated prepolymer relative to the active hydrogen group in the remaining portion of the active hydrogen compound is, for example, 0.75 to 1.3, preferably 0.9 to 1.1, and the mixture is allowed to react (curing reaction), for example, at room temperature to 250° C., preferably at room temperature to 200° C., for, for example, 5 minutes to 72 hours, preferably 1 to 24 hours.

To obtain the polyurethane resin as an aqueous dispersion, for example, first, pentamethylene diisocyanate and/or a polyisocyanate composition are/is allowed to react with an active hydrogen compound including an active hydrogen compound (hereinafter abbreviated as a hydrophilic group-containing active hydrogen compound) containing a hydrophilic group to be described later, thereby producing an isocyanate group-terminated prepolymer.

Then, the produced isocyanate group-terminated prepolymer and a chain extender are allowed to react with each other to be dispersed in water. In this manner, an aqueous polyurethane resin in which chains of an isocyanate group-terminated prepolymer are extended by a chain extender can be obtained as an internally emulsified aqueous dispersion.

To cause the isocyanate group-terminated prepolymer to react with the chain extender in water, for example, first, the isocyanate group-terminated prepolymer is added to water, thereby dispersing the isocyanate group-terminated prepolymer. Thereafter, a chain extender is added thereto, thereby causing chains of the isocyanate group-terminated prepolymer to extend.

The hydrophilic group-containing active hydrogen compound is a compound having both of a hydrophilic group and an active hydrogen group, and examples of hydrophilic groups include anionic groups (e.g., carboxyl group, etc.), cationic groups, and nonionic group (e.g., polyoxyethylene group, etc.). Examples of hydrophilic group-containing active hydrogen compounds include, to be more specific, carboxylic acid group-containing active hydrogen compounds, and polyoxyethylene group-containing active hydrogen compounds.

Examples of carboxylic acid group-containing active hydrogen compounds include dihydroxylcarboxylic acids such as 2,2-dimethylolacetic acid, 2,2-dimethylollactic acid, 2,2-dimethylol propionic acid, 2,2-dimethylolbutanoic acid, 2,2-dimethylolbutyric acid, and 2,2-dimethylolvaleric acid; diaminocarboxylic acids such as lysine, and arginine; metal salts thereof; and ammonium salts thereof.

The polyoxyethylene group-containing active hydrogen compound is a compound containing a polyoxyethylene group at its main chain or a side chain and having two or more active hydrogen groups, and examples thereof include polyethylene glycol, and polyoxyethylene side chain-containing polyol (a compound containing a polyoxyethylene group at its side chain, and having two or more active hydrogen groups).

These hydrophilic group-containing active hydrogen compounds may be used singly or in combination of two or more.

As the chain extender, for example, low-molecular-weight polyols such as the above-described dihydric alcohol, and the above-described trihydric alcohol; and diamines such as alicyclic diamines and aliphatic diamines may be used.

These chain extenders may be used singly or in combination of two or more.

When an active hydrogen compound containing a hydrophilic group-containing active hydrogen compound is used as described above, as necessary, the hydrophilic group is neutralized by a known neutralizing agent.

When the hydrophilic group-containing active hydrogen compound is not used as the active hydrogen compound, the polyurethane resin can be obtained as an externally emulsified aqueous dispersion by emulsification, for example, using a known surfactant.

Such 5-pentamethylene diisocyanate, a polyisocyanate composition, and a polyurethane resin are produced by using 1,5-pentamethylenediamine obtained at high production rates and high reaction yield as a material, and therefore can be obtained at high production rates and high reaction yield.

EXAMPLES

In the following, Examples of the present invention will be described, but the present invention is not limited thereto.

Quantities of L-lysine and 1,5-pentamethylenediamine are determined by high-performance liquid chromatography (HPLC). Analysis conditions of these and measurement method of lysine decarboxylase activity are shown below.
<Conditions for Analysis of 1,5-Pentamethylenediamine>
Column; Asahipak ODP-50 4E (manufactured by Showa Denko K.K.)
Column Temperature; 40° C.
Eluent; 0.2M sodium phosphate (pH7.7)+2.3 mM sodium 1-octanesulfonate
Eluent Flow Rate; 0.5 mL/min
For detection, postcolumn derivatization [J. Chromatogr., 83, 353-355 (1973)] using o-phthalaldehyde is used.
<Measurement Method of Lysine Decarboxylase Activity>
To 200 mM of a sodium phosphate buffer solution (pH7.0) containing 200 mM of L-lysine monohydrochloride and 0.15 mM of pyridoxal phosphate (manufactured by Hiroshima Wako Ltd.), a bacterial cell suspension or a treated bacterial cell suspension was added, thereby preparing a total mixture of 0.2 mL, and the mixture was allowed to react at 37° C. for 6 minutes. To the reaction liquid, 1 mL of hydrochloric acid (0.2M) was added, thereby terminating the reaction. The reaction terminated liquid was diluted with water appropriately, and the quantity of the produced 1,5-pentamethylenediamine was determined by HPLC.

The activity unit was set so that 1 unit represents activity of producing 1 μmol of 1,5-pentamethylenediamine in 1 minute.
<Pentamethylene Diisocyanate Concentration (Unit: Mass %)>
Using pentamethylene diisocyanate obtained in Example 12 to be described later, the pentamethylene diisocyanate concentration in the polyisocyanate composition was calculated based on calibration curve made from the area value of chromatogram obtained under the following HPLC analysis conditions.

Apparatus; Prominence® (manufactured by Shimadzu Corporation)
1) Pump LC-20AT
2) Degasser DGU-20A3
3) Autosampler SIL-20A
4) Column constant temperature bath COT-20A
5) Detector SPD-20A
Column; SHISEIDO® SILICA SG-120
Column Temperature; 40° C.
Eluent; n-hexane/methanol/1, 2-dichloroethane=90/5/5 (volume ratio)
Flow Rate; 0.2 mL/min
Detection method; UV 225 nm
<Conversion Rate of Isocyanate Group (Unit: %)>
The conversion rate of isocyanate group is determined as follows: in the chromatogram obtained under the following GPC measurement conditions, the proportion of the peak area on the high-molecular weight-side than the peak of pentamethylene diisocyanate relative to the total peak area was regarded as the conversion rate of the isocyanate group.

Apparatus; HLC®-8020 (manufactured by Tosoh Corporation)
Column; G 1000HXL, G 2000HXL and G 3000HXL (all manufactured by TOSOH CORPORATION, trade names) are connected in series
Column Temperature; 40° C.
Eluent; tetrahydrofuran
Flow Rate; 0.8 mL/min
Detection method; differential refractive index
Standard Substance; polyethylene oxide (manufactured by Tosoh Corporation, trade name: TSK® standard polyethylene oxide)
<Isocyanate Trimer Concentration (Unit: Mass %)>
The measurement described above of (conversion rate of isocyanate group) was conducted, and the peak area proportion corresponding to three times the molecular weight of pentamethylene diisocyanate was regarded as the isocyanate trimer concentration.
<Isocyanate Group Concentration (Unit: Mass %)>
The isocyanate group concentration of the polyisocyanate composition was measured by n-dibutylamine method in conformity with JIS K-1556 using a potential difference titrator.
<Viscosity (Unit: mPa·s)>
Using an E-type viscometer TV-30® manufactured by TOM Sangyo Co., Ltd., the viscosity of the polyisocyanate composition at 25° C. was measured.
<Color (Unit: APHA)>
The color of the polyisocyanate composition was measured by the method in conformity with JIS K-0071.

Reference Example 1

[Cloning of Lysine Decarboxylase Gene (cadA)]
A genomic DNA prepared from *Escherichia coli* W 3110 strain (ATCC 27325) in accordance with a common procedure was used as a template for PCR.

As the primer for PCR, oligonucleotide (synthesized by Invitrogen Corporation by request) having a base sequence shown in SEQ ID NO: 1 and SEQ ID NO: 2 designed based on the base sequence of lysine decarboxylase gene (cadA) (GenBank Accession No. AP 009048) was used. These primers have restriction enzyme recognition sequences of KpnI and XbaI in the proximity of 5'-end.

Using 25 μL of a PCR reaction liquid containing 1 ng/μL of the genomic DNA and 0.5 pmol/μL each of the primers, a PCR was conducted for 30 cycles under the following conditions: a reaction cycle of denaturation: 94° C., 30 seconds, annealing: 55° C., 30 seconds, and extension reaction: 68° C., 2 minutes.

PCR reaction product and plasmid pUC 18 (manufactured by Takara Shuzo Co., Ltd.) were digested with KpnI and XbaI, and ligated using Ligation high (manufactured by TOYOBO CO., LTD.). Thereafter, using the obtained recombinant plasmid, *Escherichia coli* DH 5α (manufactured by TOYOBO CO., LTD.) was transformed. The transformant was cultured in LB agar medium containing ampicillin (Am) 100 μg/mLb and X-Gal (5-bromo-4-chloro-3-indolyl-β-D-galactoside), thereby producing an Am-resistant, white colony transformant. The plasmid was extracted from the thus obtained transformant.

It was confirmed that the base sequence of the DNA fragment inserted into the plasmid was the base sequence shown in SEQ ID NO: 3 according to a common base sequence determination method.

The obtained plasmid having a DNA that codes lysine decarboxylase was named pCADA1.

The sequence translated into an amino acid sequence from the DNA sequence shown in SEQ ID NO: 3 is shown in SEQ ID NO: 4.

[Preparation of Transformant]

*Escherichia coli* W3110 strain was transformed by a usual method using pCADA1, and the obtained transformant was named W/pCADA1.

The transformant was inoculated into 500 ml of LB medium containing 100 μg/mL of Am in a 2 L Erlenmeyer flask having a baffle, and cultured with shaking at 30° C. for 26.5 hours. Thereafter, the culture solution was subjected to centrifugal separation at 8000 rpm for 10 minutes, and bacterial cells were collected (dry bacterial cell-based concentration was 31% (w/w)).

[Preparation of Ultrasonically Disrupted Catalyst Bacterial Cell]

The collected bacterial cell of transformant W/pCADA1 was suspended in a diluent (10 mM of a sodium phosphate buffer solution (pH7.0) containing 0.15 mM of pyridoxal phosphate and 5 g/L bovine albumin (manufactured by SIGMA)), thereby preparing a bacterial cell suspension. Then, the bacterial cell suspension was disrupted for 15 minutes in ice water using BIORUPTOR® (manufactured by Olympus Corporation).

[Preparation of Catalyst Inactivated Bacterial Cell]

The collected bacterial cell of transformant W/pCADA1 was suspended in water, thereby preparing a bacterial cell suspension having a dry bacterial cell-based concentration of 12.5 wt %. The bacterial cell suspension was incubated in a warm water bath of a temperature of 58° C. for 30 minutes, thereby giving a heat treatment; and cryopreserved at −20° C. until use.

[Preparation of Purified Enzyme]

The purified enzyme was produced by culturing a transformant by the above-described method, and purifying the collected bacterial cell by the method of Sabo et al. (Biochemistry 13 (1974) pp. 662-670). The enzyme activity of the purified enzyme was measured, and a purified enzyme of 1000 unit/mg was produced.

In this manner, it was confirmed that the activity per 1 μg of the purified enzyme was 1 unit (U).

The activity of the catalyst inactivated bacterial cell was measured, and was found to be 100 unit/mg-dry bacterial cell (Dry Cell).

Example 2

[Production of Mutant Enzyme]

A PCR was conducted using oligonucleotide (synthesized by Invitrogen Corporation by request) having a base sequence shown in Tables 1 to 6 and pCADA1 as a template.

That is, a PCR was conducted using pCADA1 as the template and SEQ ID NO: 5 and SEQ ID NO: 6 of the sequence listing for 16 cycles of a reaction cycle including the following: denaturation: 96° C., 30 seconds, annealing: 55° C., 30 seconds, and extension reaction: 68° C., 5 minutes and 20 seconds.

The obtained amplified fragment was treated with DpnI, and ligated using Ligation high. Thereafter, using the obtained recombinant plasmid, or by adding the amplified fragment treated with DpnI directly to competent cells DH5α, *Escherichia coli* DH5α strain was transformed. A plasmid was prepared from the produced strain, the base sequence was determined, and it was confirmed that the target base was replaced. The obtained plasmid was named pCAD2.

Plasmids of pCAD3 to pCAD20, and pCAD23 to pCAD119 were established in the same manner. The sequences of the oligonucleotides used are shown in Tables 1 to 6.

Strain of *Escherichia coli* W3110 was transformed by a general method using pCADA2 to pCADA20, and the obtained transformants were named W/pCADA2 to W/pCADA20. Strain of *Escherichia coli* W3110 was transformed by a general method in the same manner using pCAD23 to pCAD119, and the obtained transformants were named W/pCADA23 to W/pCADA119.

The transformant was inoculated into 500 ml of a LB medium containing 100 μg/mL of Am in a 2 L Erlenmeyer flask having a baffle, and cultured with shaking at 30° C. for 26.5 hours. Thereafter, the culture solution was subjected to centrifugal separation at 8000 rpm for 10 minutes, and bacterial cells were collected (dry bacterial cell-based concentration was 31 wt %).

Preparation of ultrasonically disrupted catalyst bacterial cell and preparation of catalyst inactivated bacterial cell were conducted in accordance with the method of Reference Example 1.

Tables 7 to 9 show pre-mutation and post-mutation in correspondence of the mutant enzyme.

TABLE 1

| Mutation Position | Primer Sequence | ID No. in Sequence Listing | Plasmid Name |
|---|---|---|---|
| 137 | GACTAAAGCACTGGTCAAATATGTTCGTG | Sequence ID No. 5 | pCADA2 |
|  | CACGAACATATTTGACCAGTGCTTTAGTC | Sequence ID No. 6 |  |
| 138 | TAAAGCACTGTTTATCTATGTTCGTGAAG | Sequence ID No. 7 | pCADA3 |
|  | CTTCACGAACATAGATAAACAGTGCTTTA | Sequence ID No. 8 |  |

TABLE 1-continued

| Mutation Position | Primer Sequence | ID No. in Sequence Listing | Plasmid Name |
|---|---|---|---|
| 286 | GCACGCTACCATTGACAAGCGCGTGAAAG<br>CTTTCACGCGCTTGTCAATGGTAGCGTGC | Sequence ID No. 9<br>Sequence ID No. 10 | pCADA4 |
| 290 | TGCTAAGCGCGTGCACGAAACACCAAACG<br>CGTTTGGTGTTTCGTGCACGCGCTTAGCA | Sequence ID No. 11<br>Sequence ID No. 12 | pCADA5 |
| 295 | AGAAACACCAAACTCAACCTGGCCGGTAC<br>GTACCGGCCAGGTTGAGTTTGGTGTTTCT | Sequence ID No. 13<br>Sequence ID No. 14 | pCADA6 |
| 303 | GGTACATGCTGTAACAACCAACTCTACCT<br>AGGTAGAGTTGGTTGTTACAGCATGTACC | Sequence ID No. 15<br>Sequence ID No. 16 | pCADA7 |
| 317 | GTACAACACCGACCAGATCAAGAAAACAC<br>GTGTTTTCTTGATCTGGTCGGTGTTGTAC | Sequence ID No. 17<br>Sequence ID No. 18 | pCADA8 |
| 335 | CTCCGCGTGGGTGGCTTACACCAACTTCT<br>AGAAGTTGGTGTAAGCCACCCACGCGGAG | Sequence ID No. 19<br>Sequence ID No. 20 | pCADA9 |
| 352 | CGGTATGAGCGGTGCACGTGTAGAAGGGA<br>TCCCTTCTACACGTGCACCGCTCATACCG | Sequence ID No. 21<br>Sequence ID No. 22 | pCADA10 |
| 353 | TATGAGCGGTGGCCATGTAGAAGGGAAAG<br>CTTTCCCTTCTACATGGCCACCGCTCATA | Sequence ID No. 23<br>Sequence ID No. 24 | pCADA11 |
| 386 | AGGTGACGTAAACTCCGAAACCTTTAACG<br>CGTTAAAGGTTTCGGAGTTTACGTCACCT | Sequence ID No. 25<br>Sequence ID No. 26 | pCADA12 |
| 443 | GATCAAACGTCTGATGACGGAATCTGATG<br>CATCAGATTCCGTCATCAGACGTTTGATC | Sequence ID No. 27<br>Sequence ID No. 28 | pCADA13 |
| 466 | GACTGAATGCTGGAACCTGCGTTCTGACA<br>TGTCAGAACGCAGGTTCCAGCATTCAGTC | Sequence ID No. 29<br>Sequence ID No. 30 | pCADA14 |
| 466 | GACTGAATGCTGGGGCCTGCGTTCTGACA<br>TGTCAGAACGCAGGCCCCAGCATTCAGTC | Sequence ID No. 31<br>Sequence ID No. 32 | pCADA15 |
| 466 | GACTGAATGCTGGTCTCTGCGTTCTGACA<br>TGTCAGAACGCAGAGACCAGCATTCAGTC | Sequence ID No. 33<br>Sequence ID No. 34 | pCADA16 |
| 475 | CAGCACCTGGCACAATTTCAAAAACATCG<br>CGATGTTTTTGAAATTGTGCCAGGTGCTG | Sequence ID No. 35<br>Sequence ID No. 36 | pCADA17 |
| 553 | CCTGCTGCGTGCTgtaACTGACTTTAAAC<br>GTTTAAAGTCAGTtacAGCACGCAGCAGG | Sequence ID No. 37<br>Sequence ID No. 38 | pCADA18 |
| 710 | CGTTAAGGTATTGACGGAAGAAAGCAAAA<br>TTTTGCTTTCTTCCGTCAATACCTTAACG | Sequence ID No. 39<br>Sequence ID No. 40 | pCADA19 |
| 711 | TAAGGTATTGAAAGACGAAAGCAAAAAAT<br>ATTTTTTGCTTTCGTCTTTCAATACCTTA | Sequence ID No. 41<br>Sequence ID No. 42 | pCADA20 |

TABLE 2

| Mutation Position (Amino Acid) | Primer | ID No. in Sequence Listing | Plasmid Name |
|---|---|---|---|
| 14 | CATGGGGGTTTATCAAAAAGAAGAACCCA<br>TGGGTTCTTCTTTTTGATAAACCCCCATG | Sequence ID No. 47<br>Sequence ID No. 48 | pCADA23 |
| 22 | ACCCATCCGTGAATTGCATCGCGCGCTTG<br>CAAGCGCGCGATGCAATTCACGGATGGGT | Sequence ID No. 49<br>Sequence ID No. 50 | pCADA24 |
| 28 | TCGCGCGCTTGAAATTCTGAACTTCCACA<br>TCTGGAAGTTCAGAATTTCAAGCGCGCGA | Sequence ID No. 51<br>Sequence ID No. 52 | pCADA25 |
| 39 | TTACCCGAACGACATAGACGACTTATTAA<br>TTAATAAGTCGTCTATGTCGTTCGGGTAA | Sequence ID No. 53<br>Sequence ID No. 54 | pCADA26 |
| 39 | TTACCCGAACGACATCGACGACTTATTAA<br>TTAATAAGTCGTCGATGTCGTTCGGGTAA | Sequence ID No. 55<br>Sequence ID No. 56 | pCADA27 |

TABLE 2-continued

| Mutation Position (Amino Acid) | Primer | ID No. in Sequence Listing | Plasmid Name |
| --- | --- | --- | --- |
| 39 | TTACCCGAACGACGTGGACGACTTATTAA<br>TTAATAAGTCGTCCACGTCGTTCGGGTAA | Sequence ID No. 57<br>Sequence ID No. 58 | pCADA28 |
| 64 | GGATAAATATAATAAAGAGCTGTGCGAAG<br>CTTCGCACAGCTCTTTATTATATTTATCC | Sequence ID No. 59<br>Sequence ID No. 60 | pCADA29 |
| 67 | TAATCTCGAGCTGACCCAAGAAATTAGCA<br>TGCTAATTTCTTCGGTCAGCTCGAGATTA | Sequence ID No. 61<br>Sequence ID No. 62 | pCADA30 |
| 67 | TAATCTCGAGCTGTTAGAAGAAATTAGCA<br>TGCTAATTTCTTCTAACAGCTCGAGATTA | Sequence ID No. 63<br>Sequence ID No. 64 | pCADA31 |
| 70 | GCTGTGCGAAGAATTGAGCAAAATGAACG<br>CGTTCATTTTGCTCAATTCTTCGCACAGC | Sequence ID No. 65<br>Sequence ID No. 66 | pCADA32 |
| 70 | GCTGTGCGAAGAACTGAGCAAAATGAACG<br>CGTTCATTTTGCTCAGTTCTTCGCACAGC | Sequence ID No. 67<br>Sequence ID No. 68 | pCADA33 |
| 70 | GCTGTGCGAAGAACCGAGCAAAATGAACG<br>CGTTCATTTTGCTCGGTTCTTCGCACAGC | Sequence ID No. 69<br>Sequence ID No. 70 | pCADA34 |
| 75 | TAGCAAAATGAACCCCAACCTGCCGTTGT<br>ACAACGGCAGGTTGGGGTTCATTTTGCTA | Sequence ID No. 71<br>Sequence ID No. 72 | pCADA35 |
| 75 | TAGCAAAATGAACCACAACCTGCCGTTGT<br>ACAACGGCAGGTTGTGGTTCATTTTGCTA | Sequence ID No. 73<br>Sequence ID No. 74 | pCADA36 |
| 79 | CGAGAACCTGCCGATATACGCGTTCGCTA<br>TAGCGAACGCGTATATCGGCAGGTTCTCG | Sequence ID No. 75<br>Sequence ID No. 76 | pCADA37 |
| 83 | GTTGTACGCGTTCCTGAATACGTATTCCA<br>TGCAATACGTATTCAGGAACGCGTACAAC | Sequence ID No. 77<br>Sequence ID No. 78 | pCADA38 |
| 83 | GTTGTACGCGTTCCTAAATACGTATTCCA<br>TGGAATACGTATTTAGGAACGCGTACAAC | Sequence ID No. 79<br>Sequence ID No. 80 | pCADA39 |
| 83 | GTTGTACGCGTTCCTTAATACGTATTCCA<br>TGGAATACGTATTAAGGAACGCGTACAAC | Sequence ID No. 81<br>Sequence ID No. 82 | pCADA40 |
| 83 | GTTGTACGCGTTCATAAATACGTATTCCA<br>TGGAATACGTATTTATGAACGCGTACAAC | Sequence ID No. 83<br>Sequence ID No. 84 | pCADA41 |
| 83 | GTTGTACGCGTTCGCCAATACGTATTCCA<br>TGGAATACGTATTGGCGAACGCGTACAAC | Sequence ID No. 85<br>Sequence ID No. 86 | pCADA42 |

TABLE 3

| Mutation Position (Amino Acid) | Primer | ID No. in Sequence Listing | Plasmid Name |
| --- | --- | --- | --- |
| 84 | GTACGCGTTCGCTGACACGTATTCCACTC<br>GAGTGGAATACGTGTCAGCGAACGCGTAC | Sequence ID No. 87<br>Sequence ID No. 88 | pCADA43 |
| 84 | GTACGCGTTCGCTACAACGTATTCCACTC<br>GAGTGGAATACGTTGTAGCGAACGCGTAC | Sequence ID No. 89<br>Sequence ID No. 90 | pCADA44 |
| 85 | CGCGTTCGCTAATCCATATTCCACTCTCG<br>CGAGAGTGGAATATGGATTAGCGAACGCG | Sequence ID No. 91<br>Sequence ID No. 92 | pCADA45 |
| 88 | TAATACGTATTCCAAACTCGATGTAAGCC<br>GGCTTACATCGAGTTTGGAATACGTATTA | Sequence ID No. 93<br>Sequence ID No. 94 | pCADA46 |
| 88 | TAATACGTATTCCAAGCTCGATGTAAGCC<br>GGCTTACATCGAGCTTGGAATACGTATTA | Sequence ID No. 95<br>Sequence ID No. 96 | pCADA47 |
| 88 | TAATACGTATTCCAGACTCGATGTAAGCC<br>GGCTTACATCGAGTCTGGAATACGTATTA | Sequence ID No. 97<br>Sequence ID No. 98 | pCADA48 |

TABLE 3-continued

| Mutation Position (Amino Acid) | Primer | ID No. in Sequence Listing | Plasmid Name |
|---|---|---|---|
| 88 | TAATACGTATTCCAATCTCGATGTAAGCC<br>GGCTTACATCGAGATTGGAATACGTATTA | Sequence ID No. 99<br>Sequence ID No. 100 | pCADA49 |
| 89 | TACGTATTCCACTTTTGATGTAAGCCTGA<br>TCAGGCTTACATCAAAAGTGGAATACGTA | Sequence ID No. 101<br>Sequence ID No. 102 | pCADA50 |
| 94 | CGATGTAAGCCTGATCGACCTGCGTTTAC<br>GTAAACGCAGGTCGATCAGGCTTACATCG | Sequence ID No. 103<br>Sequence ID No. 104 | pCADA51 |
| 95 | TGTAAGCCTGAATCCGCTGCGTTTACAGA<br>TCTGTAAACGCAGCGGATTCAGGCTTACA | Sequence ID No. 105<br>Sequence ID No. 106 | pCADA52 |
| 98 | GAATGACCTGCGTATACAGATTAGCTTCT<br>AGAAGCTAATCTGTATACGCAGGTCATTC | Sequence ID No. 107<br>Sequence ID No. 108 | pCADA53 |
| 99 | TGACCTGCGTTTAACTATTAGCTTCTTTG<br>CAAAGAAGCTAATAGTTAAACGCAGGTCA | Sequence ID No. 109<br>Sequence ID No. 110 | pCADA54 |
| 104 | GATTAGCTTCTTTAATTATGCGCTGGGTG<br>CACCCAGCGCATAATTAAAGAAGCTAATC | Sequence ID No. 111<br>Sequence ID No. 112 | pCADA55 |
| 104 | GATTAGCTTCTTTAAATATGCGCTGGGTG<br>CACCCAGCGCATATTTAAAGAAGCTAATC | Sequence ID No. 113<br>Sequence ID No. 114 | pCADA56 |
| 112 | GGGTGCTGCTGAAGAGATTGCTAATAACA<br>TGTTATTAGCAATCTCTTCAGCAGCACCC | Sequence ID No. 115<br>Sequence ID No. 116 | pCADA57 |
| 119 | TAATAAGATCAAGAACACCACTGACGAAT<br>ATTCGTCAGTGGTGTTCTTGATCTTATTA | Sequence ID No. 117<br>Sequence ID No. 118 | pCADA58 |
| 119 | TAATAAGATCAAGAATACCACTGACGAAT<br>ATTCGTCAGTGGTATTCTTGATCTTATTA | Sequence ID No. 119<br>Sequence ID No. 120 | pCADA59 |
| 119 | TAATAAGATCAAGATTACCACTGACGAAT<br>ATTCGTCAGTGGTAATCTTGATCTTATTA | Sequence ID No. 121<br>Sequence ID No. 122 | pCADA60 |
| 119 | TAATAAGATCAAGACCACCACTGACGAAT<br>ATTCGTCAGTGGTGGTCTTGATCTTATTA | Sequence ID No. 123<br>Sequence ID No. 124 | pCADA61 |
| 119 | TAATAAGATCAAGAGTACCACTGACGAAT<br>ATTCGTCAGTGGTACTCTTGATCTTATTA | Sequence ID No. 125<br>Sequence ID No. 126 | pCADA62 |

TABLE 4

| Mutation Position (Amino Acid) | Primer | ID No. in Sequence Listing | Plasmid Name |
|---|---|---|---|
| 139 | AGCACTGTTTAAAGTAGTTCGTGAAGGTA<br>TACCTTCACGAACTACTTTAAACAGTGCT | Sequence ID No. 127<br>Sequence ID No. 128 | pCADA63 |
| 139 | AGCACTGTTTAAAGTGGTTCGTGAAGGTA<br>TACCTTCACGAACCACTTTAAACAGTGCT | Sequence ID No. 129<br>Sequence ID No. 130 | pCADA64 |
| 139 | AGCACTGTTTAAATGCGTTCGTGAAGGTA<br>TACCTTCACGAACGCATTTAAACAGTGCT | Sequence ID No. 131<br>Sequence ID No. 132 | pCADA65 |
| 139 | AGCACTGTTTAAAACAGTTCGTGAAGGTA<br>TACCTTCACGAACTGTTTAAACAGTGCT | Sequence ID No. 133<br>Sequence ID No. 134 | pCADA66 |
| 139 | AGCACTGTTTAAATCTGTTCGTGAAGGTA<br>TACCTTCACGAACAGATTTAAACAGTGCT | Sequence ID No. 135<br>Sequence ID No. 136 | pCADA67 |
| 139 | AGCACTGTTTAAAAGTGTTCGTGAAGGTA<br>TACCTTCACGAACACTTTTAAACAGTGCT | Sequence ID No. 137<br>Sequence ID No. 138 | pCADA68 |
| 139 | AGCACTGTTTAAAAACGTTCGTGAAGGTA<br>TACCTTCACGAACGTTTTTAAACAGTGCT | Sequence ID No. 139<br>Sequence ID No. 140 | pCADA69 |
| 143 | ATATGTTCGTGAAGAAAAATATACTTTCT<br>AGAAAGTATATTTTTCTTCACGAACATAT | Sequence ID No. 141<br>Sequence ID No. 142 | pCADA70 |

TABLE 4-continued

| Mutation Position (Amino Acid) | Primer | ID No. in Sequence Listing | Plasmid Name |
|---|---|---|---|
| 145 | TCGTGAAGGTAAACGTACTTTCTGTACTC<br>GAGTACAGAAAGTACGTTTACCTTCACGA | Sequence ID No. 143<br>Sequence ID No. 144 | pCADA71 |
| 145 | TCGTGAAGGTAAAAGAACTTTCTGTACTC<br>GAGTACAGAAAGTTCTTTTACCTTCACGA | Sequence ID No. 145<br>Sequence ID No. 146 | pCADA72 |
| 148 | TAAATATACTTTCAGTACTCCTGGTCACA<br>TGTGACCAGGAGTACTGAAAGTATATTTA | Sequence ID No. 147<br>Sequence ID No. 148 | pCADA73 |
| 148 | TAAATATACTTTCTCTACTCCTGGTCACA<br>TGTGACCAGGAGTAGAGAAAGTATATTTA | Sequence ID No. 149<br>Sequence ID No. 150 | pCADA74 |
| 148 | TAAATATACTTTCTCCACTCCTGGTCACA<br>TGTGACCAGGAGTGGAGAAAGTATATTTA | Sequence ID No. 151<br>Sequence ID No. 152 | pCADA75 |
| 148 | TAAATATACTTTCTCAACTCCTGGTCACA<br>TGTGACCAGGAGTTGAGAAAGTATATTTA | Sequence ID No. 153<br>Sequence ID No. 154 | pCADA76 |
| 148 | TAAATATACTTTCGCGACTCCTGGTCACA<br>TGTGACCAGGAGTCGCGAAAGTATATTTA | Sequence ID No. 155<br>Sequence ID No. 156 | pCADA77 |
| 148 | TAAATATACTTTCGCAACTCCTGGTCACA<br>TGTGACCAGGAGTTGCGAAAGTATATTTA | Sequence ID No. 157<br>Sequence ID No. 158 | pCADA78 |
| 182 | ATCTGATATTTCCATGTCAGTATCTGAAC<br>GTTCAGATACTGACATGGAAATATCAGAT | Sequence ID No. 159<br>Sequence ID No. 160 | pCADA79 |
| 184 | TATTTCCATTTCAGCCTCTGAACTGGGTT<br>AACCCAGTTCAGAGGCTGAAATGGAAATA | Sequence ID No. 161<br>Sequence ID No. 162 | pCADA80 |
| 184 | TATTTCCATTTCAGCATCTGAACTGGGTT<br>AACCCAGTTCAGATGCTGAAATGGAAATA | Sequence ID No. 163<br>Sequence ID No. 164 | pCADA81 |

TABLE 5

| Mutation Position (Amino Acid) | Primer | ID No. in Sequence Listing | Plasmid Name |
|---|---|---|---|
| 253 | GACCCACCTGATGCTAATGACCGATGTTA<br>TAACATCGCTCATTAGCATCAGGTGGGTC | Sequence ID No. 165<br>Sequence ID No. 166 | pCADA82 |
| 262 | TACGCCAATCTATTATCGCCCGACCCGTA<br>TACGGGTCGGGCGATAATAGATTGGCGTA | Sequence ID No. 167<br>Sequence ID No. 168 | pCADA83 |
| 430 | CAACGGTTCTATTTTCCGTGCGATCAAAT<br>ATTTGATCGCACGGAAAATAGAACCGTTG | Sequence ID No. 169<br>Sequence ID No. 170 | pCADA84 |
| 446 | TCTGAGAACGGAATACGATGGCTGGTTCT<br>AGAACCAGCCATCGTATTCCGTTCTCAGA | Sequence ID No. 171<br>Sequence ID No. 172 | pCADA85 |
| 446 | TCTGAGAACGGAACAAGATGGCTGGTTCT<br>AGAACCAGCCATCTTGTTCCGTTCTCAGA | Sequence ID No. 173<br>Sequence ID No. 174 | pCADA86 |
| 460 | GCCGGATCATATCATTACGACTGAATGCT<br>AGCATTCAGTCGTAATGATATGATCCGGC | Sequence ID No. 175<br>Sequence ID No. 176 | pCADA87 |
| 460 | GCCGGATCATATCAATACGACTGAATGCT<br>AGCATTCAGTCGTATTGATATGATCCGGC | Sequence ID No. 177<br>Sequence ID No. 178 | pCADA88 |
| 460 | GCCGGATCATATCTGTACGACTGAATGCT<br>AGCATTCAGTCGTACAGATATGATCCGGC | Sequence ID No. 179<br>Sequence ID No. 180 | pCADA89 |
| 460 | GCCGGATCATATCCAGACGACTGAATGCT<br>AGCATTCAGTCGTCTGGATATGATCCGGC | Sequence ID No. 181<br>Sequence ID No. 182 | pCADA90 |
| 460 | GCCGGATCATATCCCCACGACTGAATGCT<br>AGCATTCAGTCGTGGGGATATGATCCGGC | Sequence ID No. 183<br>Sequence ID No. 184 | pCADA91 |

TABLE 5-continued

| Mutation Position (Amino Acid) | Primer | ID No. in Sequence Listing | Plasmid Name |
| --- | --- | --- | --- |
| 460 | GCCGGATCATATCCCTACGACTGAATGCT<br>AGCATTCAGTCGTAGGGATATGATCCGGC | Sequence ID No. 185<br>Sequence ID No. 186 | pCADA92 |
| 460 | GCCGGATCATATCCCGACGACTGAATGCT<br>AGCATTCAGTCGTCGGGATATGATCCGGC | Sequence ID No. 187<br>Sequence ID No. 188 | pCADA93 |
| 460 | GCCGGATCATATCTCAACGACTGAATGCT<br>AGCATTCAGTCGTTGAGATATGATCCGGC | Sequence ID No. 189<br>Sequence ID No. 190 | pCADA94 |
| 471 | GCTGCGTTCTGACTATACCTGGCACGGCT<br>AGCCGTGCCAGGTATAGTCAGAACGCAGC | Sequence ID No. 191<br>Sequence ID No. 192 | pCADA95 |
| 506 | CGGCACCATGAGCCCATTTGGTATTCCGG<br>CCGGAATACCAAATGGGCTCATGGTGCCG | Sequence ID No. 193<br>Sequence ID No. 194 | pCADA96 |
| 524 | CGAACATGGCATCTTAGTTGAGAAAACCG<br>CGGTTTTCTCAACTAAGATGCCATGTTCG | Sequence ID No. 195<br>Sequence ID No. 196 | pCADA97 |
| 524 | CGAACATGGCATCCTGGTTGAGAAAACCG<br>CGGTTTTCTCAACCAGGATGCCATGTTCG | Sequence ID No. 197<br>Sequence ID No. 198 | pCADA98 |
| 539 | GTTCCTGTTCAGCTGCGGTATCGATAAGA<br>TCTTATCGATACCGCAGCTGAACAGGAAC | Sequence ID No. 199<br>Sequence ID No. 200 | pCADA99 |
| 539 | GTTCCTGTTCAGCCTTGGTATCGATAAGA<br>TCTTATCGATACCAAGGCTGAACAGGAAC | Sequence ID No. 201<br>Sequence ID No. 202 | pCADA100 |

TABLE 6

| Mutation Position (Amino Acid) | Primer | ID No. in Sequence Listing | Plasmid Name |
| --- | --- | --- | --- |
| 539 | GTTCCTGTTCAGCCTAGGTATCGATAAGA<br>TCTTATCGATACCTAGGCTGAACAGGAAC | Sequence ID No. 203<br>Sequence ID No. 204 | pCADA101 |
| 544 | CGGTATCGATAAGGCGAAAGCACTGAGCC<br>GGCTCAGTGCTTTCGCCTTATCGATACCG | Sequence ID No. 205<br>Sequence ID No. 206 | pCADA102 |
| 544 | CGGTATCGATAAGGCTAAAGCACTGAGCC<br>GGCTCAGTGCTTTAGCCTTATCGATACCG | Sequence ID No. 207<br>Sequence ID No. 208 | pCADA103 |
| 544 | CGGTATCGATAAGTCTAAAGCACTGAGCC<br>GGCTCAGTGCTTTAGACTTATCGATACCG | Sequence ID No. 209<br>Sequence ID No. 210 | pCADA104 |
| 544 | CGGTATCGATAAGTCCAAAGCACTGAGCC<br>GGCTCAGTGCTTTGGACTTATCGATACCG | Sequence ID No. 211<br>Sequence ID No. 212 | pCADA105 |
| 544 | CGGTATCGATAAGCCTAAAGCACTGAGCC<br>GGCTCAGTGCTTTAGGCTTATCGATACCG | Sequence ID No. 213<br>Sequence ID No. 214 | pCADA106 |
| 544 | CGGTATCGATAAGCCGAAAGCACTGAGCC<br>GGCTCAGTGCTTTCGGCTTATCGATACCG | Sequence ID No. 215<br>Sequence ID No. 216 | pCADA107 |
| 546 | CGATAAGACCAAAAGCCTGAGCCTGCTGC<br>GCAGCAGGCTCAGGCTTTTGGTCTTATCG | Sequence ID No. 217<br>Sequence ID No. 218 | pCADA108 |
| 623 | GACTCCGTATGCTTGTTTCCAGAAAGAGC<br>GCTCTTTCTGGAAACAAGCATACGGAGTC | Sequence ID No. 219<br>Sequence ID No. 220 | pCADA109 |
| 623 | GACTCCGTATGCTTTTTTCCAGAAAGAGC<br>GCTCTTTCTGGAAAAAAGCATACGGAGTC | Sequence ID No. 221<br>Sequence ID No. 222 | pCADA110 |
| 623 | GACTCCGTATGCTTTCTTCCAGAAAGAGC<br>GCTCTTTCTGGAAGAAAGCATACGGAGTC | Sequence ID No. 223<br>Sequence ID No. 224 | pCADA111 |
| 623 | GACTCCGTATGCTCAGTTCCAGAAAGAGC<br>GCTCTTTCTGGAACTGAGCATACGGAGTC | Sequence ID No. 225<br>Sequence ID No. 226 | pCADA112 |
| 626 | TGCTGCATTCCAGGTGGAGCTGCACGGTA<br>TACCGTGCAGCTCCACCTGGAATGCAGCA | Sequence ID No. 227<br>Sequence ID No. 228 | pCADA113 |

TABLE 6-continued

| Mutation Position (Amino Acid) | Primer | ID No. in Sequence Listing | Plasmid Name |
|---|---|---|---|
| 636 | GACCGAAGAAGTTTGTCTCGACGAAATGG<br>CCATTTCGTCGAGACAAACTTCTTCGGTC | Sequence ID No. 229<br>Sequence ID No. 230 | pCADA114 |
| 636 | GACCGAAGAAGTTCCCCTCGACGAAATGG<br>CCATTTCGTCGAGGGGAACTTCTTCGGTC | Sequence ID No. 231<br>Sequence ID No. 232 | pCADA115 |
| 646 | AGGTCGTATTAACTTGAATATGATCCTTC<br>GAAGGATCATATTCAAGTTAATACGACCT | Sequence ID No. 233<br>Sequence ID No. 234 | pCADA116 |
| 646 | AGGTCGTATTAACATCAATATGATCCTTC<br>GAAGGATCATATTGATGTTAATACGACCT | Sequence ID No. 235<br>Sequence ID No. 236 | pCADA117 |
| 648 | TATTAACGCCAATTCTATCCTTCCGTACC<br>GGTACGGAAGGATAGAATTGGCGTTAATA | Sequence ID No. 237<br>Sequence ID No. 238 | pCADA118 |
| 648 | TATTAACGCCAATTCCATCCTTCCGTACC<br>GGTACGGAAGGATGGAATTGGCGTTAATA | Sequence ID No. 239<br>Sequence ID No. 240 | pCADA119 |

TABLE 7

| Mutation Position (Amino Acid) | Original Amino Acid Sequence | Original Base Sequence | Mutate Amino Acid Sequence | Mutate Base Sequence | Plasmid Name |
|---|---|---|---|---|---|
| 137 | Phe | TTT | Val | GTC | pCADA2 |
| 138 | Lys | AAA | Ile | ATC | pCADA3 |
| 286 | Ala | GCT | Asp | GAC | pCADA4 |
| 290 | Lys | AAA | His | CAC | pCADA5 |
| 295 | Ala | GCA | Ser | TCA | pCADA6 |
| 303 | Ile | ATT | Thr | ACA | pCADA7 |
| 317 | Phe | TTC | Gln | CAG | pCADA8 |
| 335 | Pro | CCT | Ala | GCT | pCADA9 |
| 352 | Gly | GGC | Ala | GCA | pCADA10 |
| 353 | Arg | CGT | His | CAT | pCADA11 |
| 386 | Glu | GAA | Ser | TCC | pCADA12 |
| 443 | Arg | AGA | Met | ATG | pCADA13 |
| 466 | Pro | CCG | Asn | AAC | pCADA14 |
| 466 | Pro | CCG | Gly | GGC | pCADA15 |
| 466 | Pro | CCG | Ser | TCT | pCADA16 |
| 475 | Gly | GGC | Asn | AAT | pCADA17 |
| 553 | Leu | CTG | Val | GTA | pCADA18 |
| 710 | Lys | AAA | Thr | ACG | pCADA19 |
| 711 | Glu | GAA | Asp | GAC | pCADA20 |
| 14 | Phe | TTT | Gln | CAA | pCADA23 |
| 22 | Leu | CTT | Leu | TTG | pCADA24 |
| 28 | Arg | CGT | Ile | ATT | pCADA25 |
| 39 | Arg | CGT | Ile | ATA | pCADA26 |
| 39 | Arg | CGT | Ile | ATC | pCADA27 |
| 39 | Arg | CGT | Val | GTG | pCADA28 |
| 64 | Leu | CTC | Lys | AAA | pCADA29 |
| 67 | Cys | TGC | Thr | ACC | pCADA30 |
| 67 | Cys | TGC | Leu | TTA | pCADA31 |
| 70 | Ile | ATT | Leu | TTG | pCADA32 |
| 70 | Ile | ATT | Leu | CTG | pCADA33 |
| 70 | Ile | ATT | Pro | CCG | pCADA34 |
| 75 | Glu | GAG | Pro | CCC | pCADA35 |
| 75 | Glu | GAG | His | CAC | pCADA36 |
| 79 | Leu | TTG | Ile | ATA | pCADA37 |
| 83 | Ala | GCT | Leu | CTG | pCADA38 |
| 83 | Ala | GCT | Leu | CTA | pCADA39 |
| 83 | Ala | GCT | Leu | CTT | pCADA40 |
| 83 | Ala | GCT | Ile | ATA | pCADA41 |
| 83 | Ala | GCT | Ala | GCC | pCADA42 |

TABLE 8

| Mutation Position (Amino Acid) | Original Amino Acid Sequence | Original Base Sequence | Mutate Amino Acid Sequence | Mutate Base Sequence | Plasmid Name |
|---|---|---|---|---|---|
| 84 | Asn | AAT | Asp | GAG | pCADA43 |
| 84 | Asn | AAT | Thr | ACA | pCADA44 |

TABLE 8-continued

| Mutation Position (Amino Acid) | Original Amino Acid Sequence | Original Base Sequence | Mutate Amino Acid Sequence | Mutate Base Sequence | Plasmid Name |
|---|---|---|---|---|---|
| 85 | Thr | ACG | Pro | CCA | pCADA45 |
| 88 | Thr | ACT | Lys | AAA | pCADA46 |
| 88 | Thr | ACT | Lys | AAG | pCADA47 |
| 88 | Thr | ACT | Arg | AGA | pCADA48 |
| 88 | Thr | ACT | Asn | AAT | pCADA49 |
| 89 | Leu | CTC | Phe | TTT | pCADA50 |
| 94 | Asn | AAT | Ile | ATC | pCADA51 |
| 95 | Asp | GAC | Pro | CCG | pCADA52 |
| 98 | Leu | TTA | Ile | ATA | pCADA53 |
| 99 | Gln | CAG | Thr | ACT | pCADA54 |
| 104 | Glu | GAA | Asn | AAT | pCADA55 |
| 104 | Glu | GAA | Lys | AAA | pCADA56 |
| 112 | Asp | GAT | Glu | GAG | pCADA57 |
| 119 | Gln | CAG | Asn | AAC | pCADA58 |
| 119 | Gln | CAG | Asn | AAT | pCADA59 |
| 119 | Gln | CAG | Ile | ATT | pCADA60 |
| 119 | Gln | CAG | Thr | ACC | pCADA61 |
| 119 | Gln | CAG | Ser | AGT | pCADA62 |
| 139 | Tyr | TAT | Val | GTA | pCADA63 |
| 139 | Tyr | TAT | Val | GTG | pCADA64 |
| 139 | Tyr | TAT | Cys | TGC | pCADA65 |
| 139 | Tyr | TAT | Thr | ACA | pCADA66 |
| 139 | Tyr | TAT | Ser | TCT | pCADA67 |
| 139 | Tyr | TAT | Ser | AGT | pCADA68 |
| 139 | Tyr | TAT | Asn | AAC | pCADA69 |
| 143 | Gly | GGT | Glu | GAA | pCADA70 |
| 145 | Tyr | TAT | Arg | CGT | pCADA71 |
| 145 | Tyr | TAT | Arg | AGA | pCADA72 |
| 148 | Cys | TGT | Ser | AGT | pCADA73 |
| 148 | Cys | TGT | Ser | TCT | pCADA74 |
| 148 | Cys | TGT | Ser | TCC | pCADA75 |
| 148 | Cys | TGT | Ser | TCA | pCADA76 |
| 148 | Cys | TGT | Ala | GCG | pCADA77 |
| 148 | Cys | TGT | Ala | GCA | pCADA78 |
| 182 | Ile | ATT | Met | ATG | pCADA79 |
| 184 | Val | GTA | Ala | GCC | pCADA80 |
| 184 | Val | GTA | Ala | GCA | pCADA81 |

TABLE 9

| Mutation Position (Amino Acid) | Original Amino Acid Sequence | Original Base Sequence | Mutate Amino Acid Sequence | Mutate Base Sequence | Plasmid Name |
|---|---|---|---|---|---|
| 253 | Met | ATG | Leu | CTA | pCADA82 |
| 262 | Phe | TTC | Tyr | TAT | pCADA83 |
| 430 | Glu | GAA | Phe | TTC | pCADA84 |
| 446 | Ser | TCT | Tyr | TAC | pCADA85 |
| 446 | Ser | TCT | Gln | CAA | pCADA86 |
| 460 | Asp | GAT | Ile | ATT | pCADA87 |
| 460 | Asp | GAT | Asn | AAT | pCADA88 |
| 460 | Asp | GAT | Cys | TGT | pCADA89 |
| 460 | Asp | CAT | Gln | CAG | pCADA90 |
| 460 | Asp | GAT | Pro | CCC | pCADA91 |
| 460 | Asp | GAT | Pro | CCT | pCADA92 |
| 460 | ASP | GAT | Pro | CCG | pCADA93 |
| 460 | Asp | GAT | Ser | TCA | pCADA94 |
| 471 | Ser | AGC | Tyr | TAT | pCADA95 |
| 506 | Asp | GAC | Pro | CCA | pCADA96 |
| 524 | Val | GTT | Leu | TTA | pCADA97 |
| 524 | Val | GTT | Leu | CTG | pCADA98 |
| 539 | Ile | ATC | Cys | TGC | pCADA99 |
| 539 | Ile | ATC | Leu | CTT | pCADA100 |
| 539 | Ile | ATC | Leu | CTA | pCADA101 |
| 544 | Thr | ACC | Ala | GCG | pCADA102 |
| 544 | Thr | ACC | Ala | GCT | pCADA103 |
| 544 | Thr | ACC | Ser | TCT | pCADA104 |
| 544 | Thr | ACC | Ser | TCC | pCADA105 |
| 544 | Thr | ACC | Pro | CCG | pCADA106 |
| 544 | Thr | ACC | Pro | CCG | pCADA107 |
| 546 | Ala | GCA | Ser | AGC | pCADA108 |
| 623 | Ala | GCA | Cys | TGT | pCADA109 |
| 623 | Ala | GCA | Phe | TTT | pCADA110 |
| 623 | Ala | GCA | Phe | TTC | pCADA111 |
| 623 | Ala | GCA | Gln | CAG | pCADA112 |
| 626 | Lys | AAA | Val | GTG | pCADA113 |
| 636 | Tyr | TAC | Cys | TGT | pCADA114 |
| 636 | Tyr | TAC | Pro | CCC | pCADA115 |
| 646 | Ala | GCC | Leu | TTG | pCADA116 |

TABLE 9-continued

| Mutation Position (Amino Acid) | Original Amino Acid Sequence | Base Sequence | Mutate Amino Acid Sequence | Base Sequence | Plasmid Name |
|---|---|---|---|---|---|
| 646 | Ala | GCC | Ile | ATC | pCADA117 |
| 648 | Met | ATG | Ser | TCT | pCADA118 |
| 648 | Met | ATG | Ser | TCC | pCADA119 |

Example 3

[Production of Multiple Mutation Strain]

A PCR was conducted using oligonucleotide (synthesized by Invitrogen Corporation by request) having a base sequence shown in SEQ ID NO: 19 and SEQ ID NO: 20, and pCADA5 as a template.

Then, a PCR was conducted for 16 cycles under the following conditions: a reaction cycle of denaturation: 96° C., 30 seconds, annealing: 55° C., 30 seconds, and extension reaction: 68° C., 5 minutes and 20 seconds.

The obtained amplified fragment was treated with DpnI, and ligated using Ligation high. Thereafter, using the obtained recombinant plasmid, or by adding the amplified fragment treated with DpnI directly to competent cells DH5α, Escherichia coli DH5α strain was transformed. A plasmid was prepared from the produced strain, the base sequence was determined, and it was confirmed that the target base was replaced. A plasmid was produced in the same manner using the plasmid as a template and the base sequence shown in SEQ ID NO: 35 and SEQ ID NO: 36, and a plasmid was produced in the same manner as described above using the plasmid and the base sequences shown in SEQ ID NO: 41 and SEQ ID NO: 42, thereby producing a plasmid having a quadruple mutant, pCADA21. The DNA sequence of the produced quadruple mutant is shown in SEQ ID NO: 43 of the sequence listing. The amino acid sequence is shown in SEQ ID NO: 44 of the sequence listing.

Furthermore, a plasmid pCADA22 having a sequence of penta mutant was produced using the base sequence shown in SEQ ID NO: 9 and SEQ ID NO: 10 and the plasmid in the same manner as described above. Strain of Escherichia coli W3110 was transformed by a general method with the plasmid, and the obtained transformants were named W/pCADA21 and W/pCADA22. The DNA sequence of the produced penta mutant is shown in SEQ ID NO: 45 of the sequence listing. The amino acid sequence is shown in SEQ ID NO: 46 of the sequence listing.

Then, a PCR was conducted using oligonucleotide having a base sequence shown in SEQ ID NO: 235 and SEQ ID NO: 236, and pCADA73 as a template. Then, a PCR was conducted for 16 cycles under the following conditions: a reaction cycle of denaturation: 96° C., 30 seconds, annealing: 55° C., 30 seconds, and extension reaction: 68° C., 5 minutes and 20 seconds. The obtained amplified fragment was treated with DpnI, and using the fragment, Escherichia coli DH5α strain was transformed. A plasmid was prepared from the produced strain, the base sequence was determined, and it was confirmed that the target base was replaced. The obtained plasmid was named pCADA120.

Then, a PCR was conducted using oligonucleotide having a base sequence shown in SEQ ID NO: 227 and SEQ ID NO: 228, and pCADA95 as a template. Then, a PCR was conducted for 16 cycles under the following conditions: a reaction cycle of denaturation: 96° C., 30 seconds, annealing: 55° C., 30 seconds, and extension reaction: 68° C., 5 minutes and 20 seconds. The obtained amplified fragment was treated with DpnI, and using the fragment, Escherichia coli DH5α strain was transformed. A plasmid was prepared from the produced strain, the base sequence was determined, and it was confirmed that the target base was replaced. The obtained plasmid was named pCADA121.

Then, a PCR was conducted using oligonucleotide having a base sequence shown in SEQ ID NO: 235 and SEQ ID NO: 236, and pCADA113 as a template. Then, a PCR was conducted for 16 cycles under the following conditions: a reaction cycle of denaturation: 96° C., 30 seconds, annealing: 55° C., 30 seconds, and extension reaction: 68° C., 5 minutes and 20 seconds. The obtained amplified fragment was treated with DpnI, and using the fragment, Escherichia coli DH5α strain was transformed. A plasmid was prepared from the produced strain, the base sequence was determined, and it was confirmed that the target base was replaced. The obtained plasmid was named pCADA122.

With these plasmids of pCADA120, pCADA121, and pCADA122, Escherichia coli W3110 strain was transformed by a usual method, and the obtained transformants were named W/pCADA120, W/pCADA121, and W/pCADA122.

The transformant was inoculated into 500 ml of a LB medium containing 100 μg/mL of ampicillin in a 2 L Erlenmeyer flask having a baffle, and cultured with shaking at 30° C. for 26.5 hours. Thereafter, the culture solution was subjected to centrifugal separation at 8000 rpm for 10 minutes, and bacterial cells were collected (dry bacterial cell-based concentration was 31 wt %).

Preparation of ultrasonically disrupted catalyst bacterial cell and preparation of catalyst inactivated bacterial cell were conducted in accordance with the method of Reference Example 1.

Reference Example 4

[Production of Lysine-Producing Bacteria and Lysine Fermentation]

APG-4 strain (hom, lysC, pyc, gnd mutation strain) was made by the method described by M. Ikeda et al. (J Ind Microbiol Biotechnol (2006) 33: 610-615) for Corynebacterium glutamicum (ATCC13032).

Two sterilized 500 ml flasks with baffles were prepared: to the flasks, 30 g of calcium carbonate was introduced in advance for lysine fermentation, and 75 ml of sterilized mediums for preculture shown in Table 10 were added aseptically. The APG-4 strain produced as described above was planted (one colony) therein, and thereafter, agitated culture was conducted at 30° C. and 120 rpm for 18 hours, thereby preparing a preculture solution.

The entire amount of the produced preculture solution was introduced into a 3 L aerated culture vessel, in which 840 ml of medium for main culture shown in Table 11 was added, and culture was conducted with an air flow rate of 1 L/min with stirring at a number of revolution of 800 rpm at 30° C. for 50 hours. The pH during culture was adjusted to 7.0 with ammonia, and a mixture solution of 40% glucose, and 4.5% ammonium chloride was added from 20 th hour from the start of culture to the completion of culture at a flow velocity of 26.7 g per 1 hour. OD660 at the time of completion of culture was 370. In the fermentation liquid after the completion of culture, 27 g/L of lysine was accumulated. The produced fermentation liquid was named fermentation liquid A.

TABLE 10

| | |
|---|---|
| Sucrose | 50 g |
| CSL | 40 g |
| Ammonium Sulfate | 8.3 g |
| Urea | 1 g |
| Potassium dihydrogenphosphate | 2 g |
| MgSO$_4$•7H$_2$O | 0.83 g |
| FeSO$_4$•7H$_2$O | 10 mg |
| CuSO$_4$•5H$_2$O | 1 mg |
| ZnSO$_4$•7H$_2$O | 10 mg |
| L-Alanine | 10 mg |
| Nicotinic Acid | 5 mg |
| Thiamine hydrochloride | 1.5 mg |
| Biotin | 0.5 mg | pH 7.0
NH$_3$aq /1 L

TABLE 11

| | |
|---|---|
| Glucose | 60 g |
| CSL | 20 g |
| Ammonium Chloride | 25 g |
| Potassium dihydrogenphosphate | 2.5 g |
| MgSO$_4$•7H$_2$O | 0.75 g |
| CaCl$_2$•2H$_2$O | 50 mg |
| FeSO$_4$•7H$_2$O | 50 mg |
| MnSO$_4$•5H$_2$O | 13 mg |
| CuSO$_4$•5H2O | 6.3 mg |
| ZnSO$_4$•7H$_2$O | 1.3 mg |
| NiCl$_2$•6H2O | 5 mg |
| CoCl$_2$•6H$_2$O | 1.3 mg |
| (NH$_4$)$_6$Mo$_7$O$_{24}$•4H$_2$O | 1.3 mg |
| L-Alanine | 23 mg |
| Nicotinic Acid | 14 mg |
| Thiamine hydrochloride | 7 mg |
| Biotin | 0.42 mg |

/1 L

To produce other fermentation liquids, 15 ml of a LB medium (Difco Cat. 244620) containing 5% glucose and 2% ammonium sulfate was introduced into a 100 ml flask with baffle, and APG-4 strain produced as described above was planted (one colony), and thereafter, culture was conducted at 30° C. and 120 rpm for 24 hours, thereby preparing a preculture solution.

The entire amount of the produced preculture solution was introduced into a 1 L aerated culture vessel, in which 350 ml of medium for main culture shown in Table 12 was added, and culture was conducted with an air flow rate of 180 ml/min with stirring at a number of revolution of 700 rpm at 31.5° C. for 50 hours. The pH during culture was adjusted to 7.0 with ammonia, and molasses were added in an amount of 50 g at 25 th hour and 30 g at 42 nd hour from the start of the main culture.

In the fermentation liquid after the completion of culture, 16 g/L of lysine was accumulated. The produced fermentation liquid was named fermentation liquid B.

The Corynebacterium glutamicum (ATCC13032) was obtained from American Type Culture Collection.

TABLE 12

| | |
|---|---|
| Molasses (Dai-Nippon Meiji Sugar CO., Ltd. (Inedible) | 160 g |
| Ammonium Sulfate | 50 g |
| KH$_2$PO$_4$ | 1 g |
| MgSO$_4$•7H$_2$O | 1 g |

TABLE 12-continued

| | |
|---|---|
| Polypepton (Nihon Pharmaceutical CO., Ltd.) | 0.8 g |
| Thiamine | 0.1 mg |
| Biotin | 0.3 mg |

/1 L

Reference Example 5

[Effects of Addition of Escherichia coli, Corynebacterium, and Yeast in Wild Type Enzyme]

A 500 ml flask having a baffle was added with 100 ml of a LB medium (Difco Cat. 244620) and sterilized. Two such flasks were prepared, and Escherichia coli (ATCC27325) and Corynebacterium glutamicum (ATCC13032) were planted, respectively, and shaking culture was performed at 30° C. for 20 hours and at 120 rpm.

A 500 ml flask having a baffle was charged with 100 ml of YPD medium (Difco Cat. 242820), and Saccharomyces cerevisiae (ATCC201388) was planted. Shaking culture was performed at 30° C. for 20 hours, and at 120 rpm.

The obtained culture solution was subjected to centrifugal separation to separate bacterial cells and supernatant was removed. A deionization ion-exchange water in an amount equal with the supernatant was added to suspend the bacterial cells, and centrifugal separation was performed again. Such operation is repeated 10 times to wash the bacterial cells, and thereafter the bacterial cells were used in the experimentation below.

The obtained bacterial cells were added with 10 ml of an aqueous solution of 12.5% lysine hydrochloride to well suspend the bacterial cells. The suspension in an amount of 1 ml was mixed with 9 ml of the aqueous solution of 12.5% lysine hydrochloride, thereby producing a solution having a bacterial cell concentration of 1/10.

Such operation is repeated 10 times, thereby producing a dilution series (by 1/10 bacterial cell concentration). To determine the bacterial cell concentration, 100 μl of each of the solutions with such concentrations was placed on a LB plate, culture was performed for 24 hours at 30° C., and the number of colonies emerged was determined. Furthermore, 5 ml of the solution with such concentrations was put into a 15 ml PP container with screw cap, and 50 μl of aqueous solution of 0.4% PLP, and 50 μl of catalyst inactivated bacterial cell prepared in Reference Example 1 diluted to 0.153% (dry bacterial cell-based) were added thereto. For the control, an aqueous solution of 12.5% lysine hydrochloride without adding bacterial cells was used, and the same operation as described above was performed.

The containers were placed side by side in the shaking direction and horizontally, and reaction was conducted at 200 rpm and 42° C. for 20 hours. To 50 μl of the reaction solution, 950 μl of 0.2M hydrochloric acid was added to terminate the reaction. The reaction terminated liquid was diluted with water appropriately, and the quantity of the produced 1,5-pentamethylenediamine was determined by HPLC.

The results are shown in Table 13.

TABLE 13

| | | | | | | | |
|---|---|---|---|---|---|---|---|
| Coryne | Bacterial Number (/ml) | $2.5 \times 10^7$ | $2.5 \times 10^6$ | $2.5 \times 10^5$ | $2.5 \times 10^4$ | $2.5 \times 10^3$ | $2.5 \times 10^2$ |
| | Accumulative Concentration | 1.563 | 1.286 | 1.057 | 1.011 | 0.995 | 0.999 |
| Escherichia Coli | Bacterial Number (/ml) | $1.0 \times 10^9$ | $1.0 \times 10^8$ | $1.0 \times 10^7$ | $1.0 \times 10^6$ | $1.0 \times 10^5$ | $1.0 \times 10^4$ |
| | Accumulative Concentration | 1.559 | 1.202 | 1.016 | 1.024 | 0.999 | 1.023 |
| Yeast | Bacterial Number (/ml) | $1.5 \times 10^9$ | $1.5 \times 10^8$ | $1.5 \times 10^7$ | $1.5 \times 10^6$ | $1.5 \times 10^5$ | $1.5 \times 10^4$ |
| | Accumulative Concentration | 1.717 | 1.839 | 1.423 | 1.007 | 0.98 | 0.981 |

In Table 13, the cumulative concentrations are shown in relative values setting the cumulative concentration of the control to 1.

Reference Example 6

[Effects of Addition of Corn Steep Liquor, Yeast Extracts, Molasses, and Peptone in Wild Type Enzyme]

To an aqueous solution of 12.5% lysine hydrochloride, 20 g/L of corn steep liquor (NIHON SHOKUHIN KAKO CO., LTD.)(neutralized with 6N NaOH)(hereinafter may be referred to as CSL), yeast extracts (Difco), molasses (Dai-Nippon Meiji Sugar Co., Ltd.), or peptone (Difco) was mixed, thereby preparing a solution. The solutions were diluted with an aqueous solution of 12.5% lysine hydrochloride by 1/2, thereby producing a dilution series ranging from 20 g/L to 0.156 g/L.

5 ml of each of the solution with such concentration was put into a 15 ml PP container with screw cap, and 50 µl of aqueous solution of 0.4% PLP, and 50 µl of catalyst inactivated bacterial cell prepared in Reference Example 1 diluted to 0.153% (dry bacterial cell-based-based) were added thereto. For the control, an aqueous solution of 12.5% lysine hydrochloride with no additive was used and the same operation as described above was performed.

The containers were placed side by side in the shaking direction and horizontally, and reaction was conducted at 200 rpm and 42° C. for 20 hours. The results are shown in Table 14.

TABLE 14

| | Concentration (g/L) | | | | | | | |
|---|---|---|---|---|---|---|---|---|
| | 20.00 | 10.00 | 5.00 | 2.50 | 1.25 | 0.63 | 0.31 | 0.16 |
| CSL | 1.44 | 1.48 | 1.41 | 1.38 | 1.20 | 1.16 | 1.16 | 1.05 |
| Yeast Extract | 1.58 | 1.57 | 1.51 | 1.30 | 1.18 | 1.12 | 1.10 | 1.04 |
| Polypepton | 1.40 | 1.30 | 1.27 | 1.10 | 1.07 | 1.08 | 1.02 | 1.02 |
| Molasses | 1.29 | 1.08 | 1.04 | 1.09 | 1.06 | 1.03 | 1.02 | 1.05 |

In Table 14, the cumulative concentrations are shown in relative values setting the cumulative concentration of the control to 1.

Reference Example 7

[Effects of Addition of Corynebacterium+corn steep liquor, Corynebacterium+yeast extracts, Corynebacterium+molasses in wild type enzyme]

A 500 ml flask having a baffle was added with 100 ml of a LB medium (Difco Cat. 244620) and sterilized. Corynebacterium glutamicum (ATCC13032) was planted, and shaking culture was performed at 30° C. for 20 hours and at 120 rpm. The obtained culture solution was subjected to centrifugal separation to separate bacterial cells and supernatant was removed. A deionization ion-exchange water in an amount equal with the supernatant was added to suspend the bacterial cells, and centrifugal separation was performed again. Such operation is repeated 10 times to wash bacterial cells, then the bacterial cells were suspended in an aqueous solution of 12.5% lysine hydrochloride, and the bacterial cells were used in the experimentation below.

To an aqueous solution of 12.5% lysine hydrochloride, 0.5 g/L of corn steep liquor (NIHON SHOKUHIN KAKO CO., LTD.)(neutralized with 6N NaOH), yeast extracts (Difco), molasses (Dai-Nippon Meiji Sugar Co., Ltd.), or peptone (Difco) was mixed, thereby preparing a solution. To 9 ml of the solution, 1 ml of the above-described bacterial cell solution was mixed in the same manner as in Reference Example 5, thereby producing a dilution series (by 1/10 bacterial cell concentration). 5 ml of the solution with such concentrations was put into a 15 ml PP container with screw cap, and 50 µl of aqueous solution of 0.4% PLP, and 50 µl of catalyst inactivated bacterial cell prepared in Reference Example 1 diluted to 0.153% (dry bacterial cell-based) were added thereto. For the control, solutions without adding bacterial cells were prepared.

The containers were placed side by side in the shaking direction and horizontally, and reaction was conducted at 200 rpm and 42° C. for 20 hours. The reaction was terminated by adding 950 µl of 0.2M hydrochloric acid to 50 µl of the reaction solution. The reaction terminated liquid was diluted with water appropriately, and the quantity of the produced 1,5-pentamethylenediamine was determined by HPLC. The results are shown in Table 15.

TABLE 15

| | | | | | | |
|---|---|---|---|---|---|---|
| Yeast Extract | 1.769 | 1.610 | 1.205 | 1.078 | 1.046 | 1.042 |
| CSL | 1.542 | 1.416 | 1.309 | 1.217 | 1.158 | 1.060 |
| Molasses | 1.489 | 1.394 | 1.295 | 1.200 | 1.123 | 1.058 |
| Bacterial Number (/ml) | $1.9 \times 10^7$ | $1.9 \times 10^6$ | $1.9 \times 10^5$ | $1.9 \times 10^4$ | $1.9 \times 10^3$ | $1.9 \times 10^2$ |

In Table 15, the cumulative concentrations are shown in relative values setting the cumulative concentration of the control to 1.

Reference Example 8

[Effects of Reaction of Fermentation Liquid in Wild Type Enzyme]

5 ml of fermentation liquid A prepared in Reference Example 4 was put into a 15 ml PP container with screw cap, and 50 μl of aqueous solution of 0.4% PLP, and 10 μl of catalyst inactivated bacterial cell prepared in Reference Example 1 diluted to 0.153% (dry bacterial cell-based) were added thereto. Then, fermentation liquid A was subjected to centrifugal separation, and the supernatant was filtered with a 0.22 μm filter to separate therefrom. 5 ml of the supernatant was put into a 15 ml PP container with screw cap, and 50 μl of aqueous solution of 0.4% PLP and 10 μl of catalyst inactivated bacterial cell prepared in Reference Example 1 diluted to 0.153% (dry bacterial cell-based) were added thereto. Furthermore, 1 ml of the supernatant was mixed with 9 ml of a mixture in which lysine hydrochloride (Wako) was dissolved in an ion-exchange water so that the lysine concentration was 27 g/L, and the mixture was named a diluted mixture liquid of fermentation liquid. 5 ml of the diluted mixture liquid of fermentation liquid was put into a 15 ml PP container with screw cap, and 50 μl of aqueous solution of 0.4% PLP and 10 μl of catalyst inactivated bacterial cell prepared in Reference Example 1 diluted to 0.153% (dry bacterial cell-based) were added thereto. For the control, lysine hydrochloride (Wako) was dissolved in ion-exchange water so that the lysine concentration was 27 g/L and used.

The containers were placed side by side in the shaking direction and horizontally, and reaction was conducted at 200 rpm and 42° C. for 24 hours. The reaction was terminated by adding 950 μl of 0.2M hydrochloric acid to 50 μl of the reaction solution. The reaction terminated liquid was diluted with water appropriately, and the quantity of the produced 1,5-pentamethylenediamine was determined by HPLC. The results are shown in Table 16.

TABLE 16

| Sample | Control | Fermentation Liquid A | Supernatant | Diluted Mixture Liquid |
|---|---|---|---|---|
| Conversion | 36.17% | 71.82% | 72.58% | 72.35% |

Conversion rate was calculated as follows:

Conversion rate (%) = produced 1,5-pentamethylenediamine (mol)/substrate lysine (mol).

Next, 5 ml of a solution, in which lysine hydrochloride (Wako) was dissolved in fermentation liquid A/fermentation liquid B prepared in Reference Example 4 so that the lysine concentration thereof was 100 g/L, was put into a 15 ml PP container with screw cap. To the solution, 50 μl of aqueous solution of 0.4% PLP, and 100, 50, 25, or 12.5 μl of a solution, in which catalyst inactivated bacterial cell prepared in Reference Example 1 was diluted to 0.83% (dry bacterial cell-based), were added. The activities calculated based on purified enzyme were 16.1 mg/L, 8 mg/L, 4 mg/L, and 2 mg/L, respectively. The activities calculated based on 1 g of lysine were 161 U, 80 U, 40 U, and 20 U, respectively. For the control, lysine hydrochloride (Wako) was dissolved in ion-exchange water so that the lysine concentration was 100 g/L and used.

Figure 2:
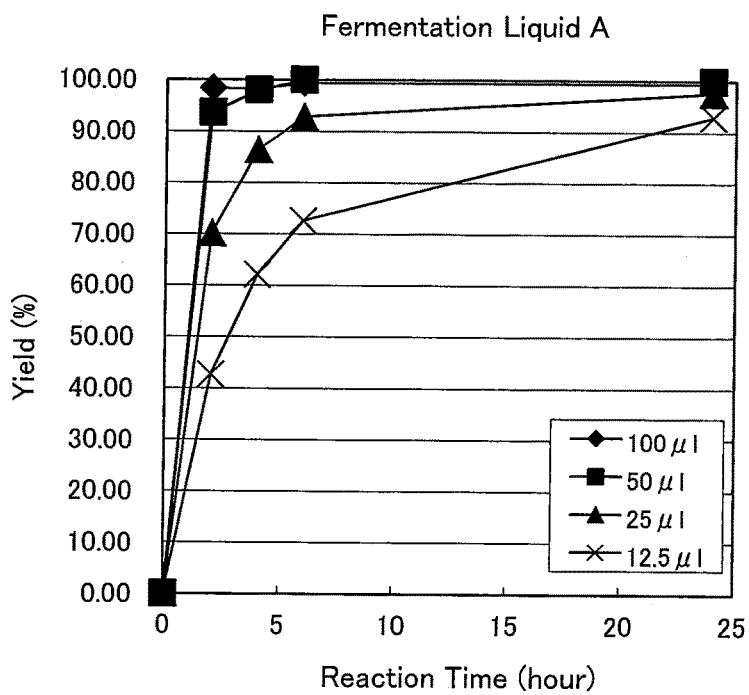
FIG. 2 is a graph illustrating reaction efficiency of lysine decarboxylation in fermentation liquid A.
Figure 3:
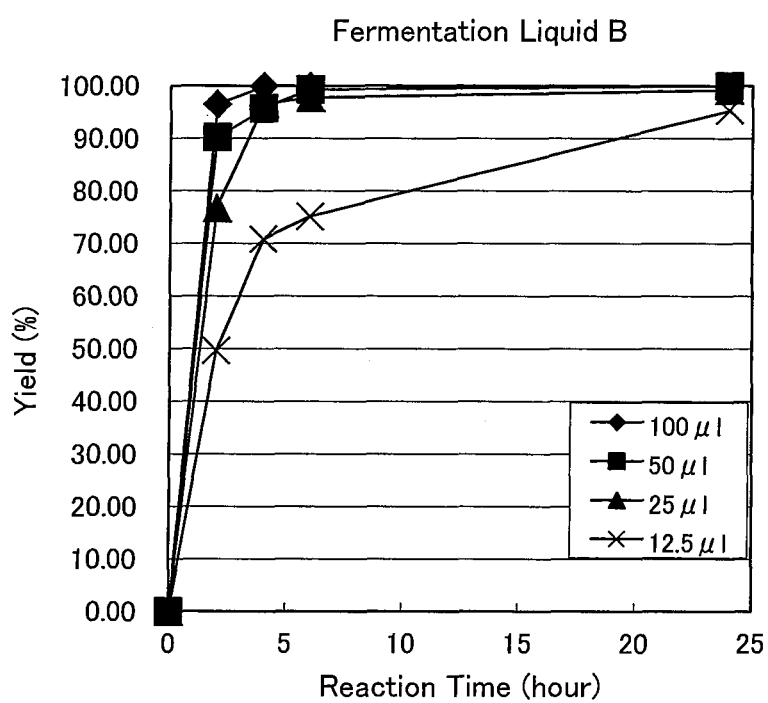
FIG. 3 is a graph illustrating reaction efficiency of lysine decarboxylation in fermentation liquid B.

The containers were placed side by side in the shaking direction and horizontally, and reaction was conducted at 200 rpm and 42° C. for 24 hours. The reaction was terminated by adding 950 μl of 0.2M hydrochloric acid to 50 μl of the reaction solution. The reaction terminated liquid was diluted with water appropriately, and the quantity of the produced 1,5-pentamethylenediamine was determined by HPLC. The results are shown in Tables 17 to 20 and FIGS. 1 to 3.

TABLE 17

| Catalyst Inactivated Bacterial Cell | 12.5 μl | 25 μl | 50 μl | 100 μl |
|---|---|---|---|---|
| Control | 44.01% | 60.58% | 83.14% | 98.25% |
| Fermentation Liquid A | 92.95% | 97.61% | 100% | 99.43% |
| Fermentation Liquid B | 95.38% | 99.23% | 100% | 100% |

TABLE 18

| Catalyst Inactivated Bacterial Cell | | 12.5 μl | 25 μl | 50 μl | 100 μl |
|---|---|---|---|---|---|
| Time | 0 | 0.00 | 0.00 | 0.00 | 0.00 |
| | 2.0 | 30.87 | 50.81 | 79.03 | 98.02 |
| | 4.0 | 39.57 | 58.05 | 83.75 | 98.12 |
| | 6.0 | 40.39 | 59.27 | 83.83 | 98.25 |
| | 24.0 | 44.01 | 60.58 | 83.14 | 98.25 |

Unit (%)

TABLE 19

| Catalyst Inactivated Bacterial Cell | | 12.5 μl | 25 μl | 50 μl | 100 μl |
|---|---|---|---|---|---|
| Time | 0 | 0.00 | 0.00 | 0.00 | 0.00 |
| | 2.0 | 42.70 | 70.13 | 93.62 | 98.40 |
| | 4.0 | 62.07 | 86.39 | 98.03 | 98.18 |
| | 6.0 | 72.58 | 92.81 | 100.00 | 99.43 |
| | 24.0 | 92.95 | 97.61 | 100.00 | 99.43 |

Unit (%)

TABLE 20

| Catalyst Inactivated Bacterial Cell | | 12.5 μl | 25 μl | 50 μl | 100 μl |
|---|---|---|---|---|---|
| Time | 0 | 0.00 | 0.00 | 0.00 | 0.00 |
| | 2.0 | 49.65 | 76.75 | 90.25 | 96.59 |
| | 4.0 | 70.85 | 96.52 | 95.73 | 99.88 |
| | 8.0 | 75.17 | 97.79 | 99.32 | 100.00 |
| | 24.0 | 95.38 | 99.23 | 100.00 | 100.00 |

Unit (%)

Conversion rate was calculated as follows:

Conversion rate (%) = produced 1,5-pentamethylenediamine (mol)/substrate lysine (mol).

Example 9

[Reaction of Mutant Enzyme]

W/pCADA1 to W/pCADA22 obtained in Reference Example 1, Example 2, and Example 3 were inoculated into 500 mL of a LB medium containing 100 μg/mL of ampicillin in a 2 L Erlenmeyer flask having a baffle, and culture was conducted with shaking at 30° C. until the optical density (OD)(660 nm) reached 0.5. Thereafter, IPTG (isopropyl-β-thiogalactopyranoside) was added to be an amount of 0.1 mM, and culture was conducted with shaking was further conducted for 14 hours. The culture solution was subjected to centrifugal separation at 8000 rpm for 20 minutes, and bacterial cells were collected (dry bacterial cell-based concentration was about 30 wt %).

[Preparation of Bacterial Cell-Disrupted Solution]

The collected bacterial cells from the obtained transformant W/pCADA1 to W/pCADA22 were suspended in a diluent (10 mM sodium phosphate buffer solution (pH7.0) containing 0.15 mM pyridoxal phosphate and 5 g/L bovine albumin (manufactured by SIGMA)), thereby preparing a bacterial cell suspension. The bacterial cell suspension was disrupted for 5 minutes in ice water using BIORUPTOR® (manufactured by Olympus Corporation) in the same manner as in Reference Example 1, thereby preparing a bacterial cell-disrupted solution.

[Measurement Method of Lysine Decarboxylase Activity]

The bacterial cell-disrupted solution in an amount of 20 µl was added to a 200 mM of sodium phosphate buffer solution (pH7.0, pH8.0) containing 200 mM L-lysine hydrochloride and 0.15 mM pyridoxal phosphate (manufactured by Hiroshima Wako Ltd.) so that the total was 0.2 mL, and the mixture was subjected to reaction at 37° C. for 4 minutes. The reaction was terminated by adding 1 mL of 0.2 M hydrochloric acid to the reaction solution. The reaction terminated liquid was diluted with water appropriately, and the quantity of the produced 1,5-pentamethylenediamine was determined by HPLC. The results are shown in Table 21 (pH7.0) and Table 22 (pH8.0).

TABLE 21

| W/pCADA1 | 1.00 |
|---|---|
| W/pCADA2 | 1.13 |
| W/pCADA3 | 1.06 |
| W/pCADA4 | 1.07 |
| W/pCADA5 | 1.06 |
| W/pCADA6 | 1.04 |
| W/pCADA7 | 1.08 |
| W/pCADA8 | 1.07 |
| W/pCADA9 | 1.11 |
| W/pCADA10 | 1.10 |
| W/pCADA11 | 1.14 |
| W/pCADA12 | 1.08 |
| W/pCADA13 | 1.06 |
| W/pCADA14 | 1.17 |
| W/pCADA15 | 1.07 |
| W/pCADA16 | 1.07 |
| W/pCADA17 | 1.13 |
| W/pCAOA18 | 1.06 |
| W/pCADA19 | 1.06 |
| W/pCADA20 | 1.09 |
| W/pCADA21 | 1.64 |
| W/pCADA22 | 1.46 |

The values in Table 21 show concentration, and are relative values setting the concentration of W/pCADA1 to 1.

TABLE 22

| W/pCADA1 | 1.00 |
|---|---|
| W/pCADA2 | 1.33 |
| W/pCADA3 | 1.14 |
| W/pCADA4 | 1.11 |
| W/pCADA5 | 1.32 |
| W/PCADA6 | 1.24 |
| W/pCADA7 | 1.31 |
| W/pCADA8 | 1.35 |
| w/pCADA9 | 1.39 |
| W/pCADA10 | 1.22 |
| W/pCADA11 | 1.25 |
| W/pCADA12 | 1.29 |
| W/pCADA13 | 1.23 |
| W/pCADA14 | 1.10 |
| W/pCADA15 | 1.26 |
| W/pCADA16 | 1.26 |
| W/pCADA17 | 1.20 |
| W/pCADA18 | 1.14 |
| W/pCADA19 | 1.39 |
| W/pCADA20 | 1.24 |
| W/PCADA21 | 1.10 |
| W/pCADA22 | 1.42 |

The values in Table 22 show concentration, and are relative values setting the concentration of W/pCADA1 to 1.

The bacterial cell-disrupted solution in an amount of 20 µl was added to a 200 mM sodium phosphate buffer solution (pH7.5) containing 0.5M 1,5-pentamethylenediamine, 200 mM L-lysine hydrochloride, and 0.15 mM pyridoxal phosphate (manufactured by Hiroshima Wako Ltd.) so that the total was 0.2 mL, and reaction was conducted at 37° C. for 6 minutes. As a comparison, the bacterial cell-disrupted solution in an amount of 20 µl was added to a 200 mM sodium phosphate buffer solution (pH7.5) containing 200 mM L-lysine hydrochloride and 0.15 mM pyridoxal phosphate (manufactured by Hiroshima Wako Ltd.) so that the total was 0.2 mL, and reaction was conducted at 37° C. for 6 minutes. To the reaction solution, 1 mL of 0.2M hydrochloric acid was added to terminate the reaction. The reaction terminated liquid was diluted with water appropriately, and the amount of reduced lysine was determined by HPLC. The results are shown in Table 23.

TABLE 23

| W/pCAD1 | 1 |
|---|---|
| W/pCAD2 | 3.05 |
| W/pCAD4 | 2.31 |
| W/pCAD5 | 4.48 |
| W/pCAD6 | 3.78 |
| W/pCAD7 | 4.15 |
| W/pCAD9 | 4.97 |
| W/pCAD10 | 1.83 |
| W/pCAD11 | 4.65 |
| W/pCAD13 | 2.14 |
| W/pCAD14 | 1.63 |
| W/pCAD17 | 1.52 |
| W/pCAD20 | 4.94 |
| W/pCAD21 | 2.77 |
| W/pCAD22 | 3.27 |

The values in Table 23 show concentration, and are relative values setting the concentration of W/pCADA1 to 1.

Example 10

[Mutant Enzyme: Effects of Reaction with Fermentation Liquid]

W/pCADA1 to W/pCADA22 produced in Reference Example 1, Example 2, and Example 3 were planted in a test tube containing 3 ml of a LB medium (Difco Cat. 244620), and culture was conducted at 26° C. and 200 rpm for 24 hours. The produced 1 ml of culture solution was put into a 1.5 ml tube, and was subjected to centrifugal separation, thereby collecting bacterial cells. The supernatant was removed and the produced bacterial cells were added with 1 ml of bacterial cell-disrupted solution (0.1% TRITON X-100®, 0.004% PLP, 100 mM sodium phosphate buffer solution (pH7.0)). Thereafter, the bacterial cells were suspended, and heated at 58° C. for 30 minutes.

Next, lysine hydrochloride (Wako) was dissolved in fermentation liquid A prepared in Reference Example 4 so that the lysine concentration was 100 g/L, and 5 ml of such solution was put into a 15 ml PP container with screw cap. To the solution, 50 µl of aqueous solution of 0.4% PLP and 50 µl of the bacterial cell-disrupted solution prepared as described above were added. The activity corresponded to a concentration of 0.54 mg/L based on purified enzyme. The activity corresponded to 5.4 U relative to 1 g of lysine. For the control, lysine hydrochloride (Wako) was dissolved in ion-exchange water so that the lysine concentration was 100 g/L and used.

The containers were placed side by side in the shaking direction and horizontally, and reaction was conducted at 200 rpm and 42° C. for 20 hours. The reaction was terminated by adding 1 mL of 0.2M hydrochloric acid to the reaction solution. The reaction terminated liquid was diluted with water appropriately, and the quantity of the produced 1,5-pentamethylenediamine was determined by HPLC. The results are shown in Table 24.

TABLE 24

|  | Control | Fermentation Liquid A |
|---|---|---|
| W/pCADA1 | 1 | 2.84 |
| W/PCADA2 | 1.37 | 3.73 |
| W/PCADA3 | 2.01 | 3.92 |
| W/PCADA4 | 1.78 | 3.86 |
| W/pCADA5 | 1.56 | 3.59 |
| W/pCADA6 | 1.25 | 3 |
| W/pCADA7 | 1.35 | 3.18 |
| W/pCADA8 | 1.13 | 3.48 |
| W/pCADA9 | 1.3 | 2.46 |
| W/pCADA10 | 1.23 | 2.91 |
| W/pCADA11 | 1.11 | 2.52 |
| W/pCADA12 | 1.38 | 3.76 |
| W/pCADA13 | 1.11 | 3.03 |
| W/pCADA14 | 1.14 | 2.67 |
| W/pCADA15 | 1.38 | 3.2 |
| W/pCADA16 | 1.23 | 3.98 |
| W/pCADA17 | 1.17 | 2.87 |
| W/pCADA18 | 1.21 | 2.78 |
| W/pCADA19 | 1.05 | 3.52 |
| W/pCADA20 | 1.17 | 2.94 |
| W/pCADA21 | 1.22 | 3.29 |
| W/pCADA22 | 1.92 | 3.81 |

The values in Table 24 show concentration, and are relative values setting the concentration of W/pCADA1 of control test region as 1.

W/pCADA1, and W/pCADA23 to W/pCADA119 obtained in Reference Example 1, Example 2, and Example 3 were planted in a test tube containing 3 ml of a LB medium (Difco Cat. 244620), and IPTG (isopropyl-β-thiogalactopyranoside) was added to be an amount of 0.1 mM, and culture was conducted at 33° C. and 200 rpm for 24 hours. The produced culture solution in an amount of 1 ml was put into a 1.5 ml tube, and preserved at −20° C. until use.

Next, 5 ml of a solution, in which lysine hydrochloride (Wako) was dissolved in fermentation liquid A prepared in Reference Example 4 so that the lysine concentration was 10 mass %, was put into a 15 ml PP container with screw cap, and 50 µl of aqueous solution of 0.4% PLP and 200 µl of a solution in which the frozen culture solution as described above was melted and well-stirred were added thereto. For the control, lysine hydrochloride (Wako) was dissolved in ion-exchange water so that the lysine concentration was 10 mass % and used. The containers were placed side by side in the shaking direction and horizontally, and reaction was conducted at 200 rpm and 45° C. for 2 hours. The reaction was terminated by adding 1 mL of 2M hydrochloric acid to the reaction solution. The reaction terminated liquid was diluted with water appropriately, and the quantity of the produced 1,5-pentamethylenediamine was determined by HPLC.

The results are shown in Tables 25 to 29.

TABLE 25

|  | Control | Fermentation Liquid A |
|---|---|---|
| W/pCADA1 | 1.00 | 1.30 |
| W/pCADA23 | 1.08 | 1.42 |
| W/pCADA24 | 1.10 | 1.46 |
| W/pCADA25 | 1.02 | 1.37 |
| W/pCADA26 | 1.05 | 1.42 |
| W/pCADA27 | 1.03 | 1.41 |
| W/pCADA28 | 1.04 | 1.39 |
| W/pCADA29 | 1.04 | 1.40 |
| W/pCADA30 | 1.12 | 1.44 |
| W/pCADA31 | 1.13 | 1.45 |
| W/pCADA32 | 1.15 | 1.42 |
| W/pCADA33 | 1.14 | 1.42 |
| W/pCADA34 | 1.12 | 1.42 |
| W/pCADA35 | 1.12 | 1.38 |
| W/pCADA36 | 1.13 | 1.41 |
| W/pCADA37 | 1.09 | 1.39 |
| W/pCADA38 | 1.16 | 1.47 |
| W/pCADA39 | 1.16 | 1.44 |
| W/pCADA40 | 1.15 | 1.40 |
| W/pCADA41 | 1.16 | 1.48 |
| W/pCADA42 | 1.16 | 1.40 |

TABLE 26

|  | Control | Fermentation Liquid A |
|---|---|---|
| W/pCADA43 | 1.04 | 1.40 |
| W/pCADA44 | 1.07 | 1.42 |
| W/pCADA45 | 1.16 | 1.49 |
| W/pCADA46 | 1.07 | 1.45 |
| W/pCADA47 | 1.04 | 1.44 |
| W/pCADA48 | 1.07 | 1.40 |
| W/pCADA49 | 1.06 | 1.42 |
| W/pCADA50 | 1.06 | 1.41 |
| W/pCADA51 | 1.04 | 1.39 |
| W/pCADA52 | 1.14 | 1.47 |
| W/pCADA53 | 1.01 | 1.40 |
| W/pCADA54 | 1.05 | 1.37 |
| W/pCADA55 | 1.05 | 1.42 |
| W/pCADA56 | 1.10 | 1.45 |
| W/pCADA57 | 1.07 | 1.38 |
| W/pCADA58 | 1.17 | 1.40 |
| W/pCADA59 | 1.18 | 1.43 |
| W/pCADA60 | 1.14 | 1.41 |
| W/pCADA61 | 1.16 | 1.44 |
| W/pCADA62 | 1.15 | 1.41 |

TABLE 27

|  | Control | Fermentation Liquid A |
|---|---|---|
| W/pCADA63 | 1.19 | 1.57 |
| W/pCADA64 | 1.21 | 1.54 |
| W/pCADA65 | 1.17 | 1.46 |
| W/pCADA66 | 1.15 | 1.52 |
| W/pCADA67 | 1.11 | 1.48 |
| W/pCADA68 | 1.13 | 1.51 |
| W/pCADA69 | 1.13 | 1.48 |
| W/pCADA70 | 1.07 | 1.54 |
| W/pCADA71 | 1.07 | 1.40 |
| W/pCADA72 | 1.05 | 1.39 |
| W/pCADA73 | 1.09 | 1.47 |
| W/pCADA74 | 1.09 | 1.47 |

TABLE 27-continued

|  | Control | Fermentation Liquid A |
|---|---|---|
| W/pGADA75 | 1.09 | 1.48 |
| W/pCADA76 | 1.10 | 1.48 |
| W/pCADA77 | 1.05 | 1.47 |
| W/pCADA78 | 1.04 | 1.49 |
| W/pCADA79 | 1.06 | 1.42 |
| W/pGADA80 | 1.05 | 1.44 |
| W/pCADA81 | 1.06 | 1.47 |

TABLE 28

|  | Control | Fermentation Liquid A |
|---|---|---|
| W/pCADA82 | 1.03 | 1.41 |
| W/pCADA83 | 1.01 | 1.35 |
| W/pCADA84 | 1.00 | 1.39 |
| W/pCADA85 | 1.02 | 1.41 |
| W/pCADA86 | 1.01 | 1.41 |
| W/pCADA87 | 1.02 | 1.36 |
| W/pCADA88 | 1.06 | 1.40 |
| W/pCADA89 | 1.11 | 1.42 |
| W/pCADA90 | 1.14 | 1.41 |
| W/pCADA91 | 1.02 | 1.45 |
| W/pCADA92 | 1.02 | 1.40 |
| W/pCADA93 | 1.02 | 1.37 |
| W/pCADA94 | 1.04 | 1.37 |
| W/pCADA95 | 1.03 | 1.49 |
| W/pCADA96 | 1.02 | 1.40 |
| W/pCADA97 | 1.16 | 1.58 |
| W/pCADA98 | 1.17 | 1.54 |
| W/pCADA99 | 1.13 | 1.42 |
| W/pCADA100 | 1.14 | 1.38 |

TABLE 29

|  | Control | Fermentation Liquid A |
|---|---|---|
| W/pCADA101 | 1.14 | 1.40 |
| W/pCADA102 | 1.19 | 1.52 |
| W/pCADA103 | 1.15 | 1.54 |
| W/pCADA104 | 1.17 | 1.51 |
| W/pCADA105 | 1.17 | 1.48 |
| W/pCADA106 | 1.15 | 1.50 |
| W/pCADA107 | 1.17 | 1.51 |
| W/pCADA108 | 1.03 | 1.36 |
| W/pCADA109 | 1.07 | 1.48 |
| W/pCADA110 | 1.07 | 1.45 |
| W/pCADA111 | 1.08 | 1.44 |
| W/pCADA112 | 1.05 | 1.43 |
| W/pGADA113 | 1.05 | 1.40 |
| W/pCADA114 | 1.05 | 1.42 |
| W/pCADA115 | 1.06 | 1.42 |
| W/pCADA116 | 1.03 | 1.40 |
| W/pCADA117 | 1.05 | 1.47 |
| W/pCADA118 | 1.11 | 1.41 |
| W/pCADA119 | 1.10 | 1.37 |

The values in Tables 25 to 29 show concentration, and are relative values setting the concentration of W/pCADA1 of control test region as 1.

W/pCADA1, and W/pCADA23 to W/pCADA119 produced in Reference Example 1, Example 2, and Example 3 were planted in a test tube containing 3 ml of a LB medium (Difco Cat. 244620), IPTG (isopropyl-β-thiogalactopyranoside) was added to be an amount of 0.1 mM, and culture was conducted at 33° C. and 200 rpm for 24 hours. The produced culture solution in an amount of 1 ml was put into a 1.5 ml tube, and preserved at −20° C. until use.

Next, lysine hydrochloride (Wako) was dissolved in fermentation liquid A prepared in Reference Example 4 to be 45 mass %, and 5 ml of such solution was put into a 15 ml PP container with screw cap. To the solution, 50 μl of aqueous solution of 0.4% PLP and 200 μl of the culture solution frozen as described above melted and well stirred were added. For the control, lysine hydrochloride (Wako) was dissolved in ion-exchange water so that lysine concentration was 45 mass % and used. The containers were placed side by side in the shaking direction and horizontally, and reaction was conducted at 200 rpm and 45° C. for 18 hours. The reaction was terminated by adding 100 μl of the reaction solution to 900 μl of 2M hydrochloric acid. The reaction terminated liquid was diluted with water appropriately, and the quantity of the produced 1,5-pentamethylenediamine was determined by HPLC. The results are shown in Tables 30 to 34.

TABLE 30

|  | Control | Fermentation Liquid A |
|---|---|---|
| W/pCADA1 | 1.00 | 2.70 |
| W/pCADA23 | 1.42 | 2.84 |
| W/pCADA24 | 1.49 | 2.92 |
| W/pCADA25 | 1.11 | 2.74 |
| W/pCADA26 | 1.25 | 2.84 |
| W/pCADA27 | 1.17 | 2.81 |
| W/pCADA28 | 1.22 | 2.78 |
| W/pCADA29 | 1.18 | 2.79 |
| W/pCADA30 | 1.60 | 2.88 |
| W/pCADA31 | 1.65 | 2.89 |
| W/pCADA32 | 1.75 | 2.83 |
| W/pCADA33 | 1.68 | 2.85 |
| W/pCADA34 | 1.59 | 2.85 |
| W/pCADA35 | 1.60 | 2.76 |
| W/pCADA36 | 1.66 | 2.81 |
| W/pCADA37 | 1.45 | 2.77 |
| W/pCADA38 | 1.79 | 2.94 |
| W/pCADA39 | 1.82 | 2.88 |
| W/pCADA40 | 1.77 | 2.79 |
| W/pCADA41 | 1.81 | 2.97 |
| W/pCADA42 | 1.79 | 2.81 |

TABLE 31

|  | Control | Fermentation Liquid A |
|---|---|---|
| W/pCADA43 | 1.22 | 2.79 |
| W/pCADA44 | 1.37 | 2.84 |
| W/pCADA45 | 1.81 | 2.98 |
| W/pCADA46 | 1.36 | 2.90 |
| W/pCADA47 | 1.19 | 2.87 |
| W/pCADA48 | 1.33 | 2.79 |
| W/pCADA49 | 1.28 | 2.84 |
| W/pCADA50 | 1.31 | 2.83 |
| W/pCADA51 | 1.22 | 2.78 |
| W/pCADA52 | 1.71 | 2.94 |
| W/pCADA53 | 1.06 | 2.80 |
| W/pCADA54 | 1.24 | 2.74 |
| W/pCADA55 | 1.25 | 2.85 |
| W/pCADA56 | 1.49 | 2.89 |
| W/pCADA57 | 1.36 | 2.77 |
| W/pCADA58 | 1.86 | 2.80 |
| W/pCADA59 | 1.88 | 2.86 |
| W/pCADA60 | 1.68 | 2.83 |
| W/pCADA61 | 1.80 | 2.87 |
| W/pCADA62 | 1.74 | 2.81 |

TABLE 32

| | Control | Fermentation Liquid A |
|---|---|---|
| W/pCADA63 | 1.95 | 3.13 |
| W/pCADA64 | 2.07 | 3.08 |
| W/pCADA65 | 1.85 | 2.92 |
| W/pCADA66 | 1.75 | 3.05 |
| W/pCADA67 | 1.54 | 2.96 |
| W/pCADA68 | 1.67 | 3.02 |
| W/pCADA69 | 1.66 | 2.96 |
| W/pCADA70 | 1.36 | 3.08 |
| W/pCADA71 | 1.36 | 2.80 |
| W/pCADA72 | 1.25 | 2.78 |
| W/pCADA73 | 1.47 | 2.93 |
| W/pCADA74 | 1.45 | 2.94 |
| W/pCADA75 | 1.46 | 2.97 |
| W/pCADA76 | 1.49 | 2.95 |
| W/pGADA77 | 1.24 | 2.93 |
| W/pGADA78 | 1.20 | 2.97 |
| W/pCADA79 | 1.29 | 2.84 |
| W/pCADA80 | 1.23 | 2.87 |
| W/pCADA81 | 1.32 | 2.94 |

TABLE 33

| | Control | Fermentation Liquid A |
|---|---|---|
| W/pCADA82 | 1.16 | 2.82 |
| W/pCADA83 | 1.03 | 2.70 |
| W/pCADA84 | 1.00 | 2.77 |
| W/pCADA85 | 1.12 | 2.83 |
| W/pCADA86 | 1.05 | 2.81 |
| W/pCADA87 | 1.12 | 2.72 |
| W/pCADA88 | 1.28 | 2.81 |
| W/pCADA89 | 1.55 | 2.83 |
| W/pCADA90 | 1.70 | 2.82 |
| W/pCADA91 | 1.11 | 2.90 |
| W/pCADA92 | 1.12 | 2.80 |
| W/pCADA93 | 1.11 | 2.73 |
| W/pCADA94 | 1.22 | 2.74 |
| W/pGADA95 | 1.13 | 2.99 |
| W/pCADA96 | 1.10 | 2.80 |
| W/pCADA97 | 1.79 | 3.16 |
| W/pCADA98 | 1.84 | 3.07 |
| W/pCADA99 | 1.67 | 2.83 |
| W/pCADA100 | 1.70 | 2.76 |

TABLE 34

| | Control | Fermentation Liquid A |
|---|---|---|
| W/pCADA101 | 1.69 | 2.80 |
| W/pCADA102 | 1.94 | 3.05 |
| W/pCADA103 | 1.75 | 3.08 |
| W/pCADA104 | 1.83 | 3.02 |
| W/pCADA105 | 1.83 | 2.96 |
| W/pCADA106 | 1.76 | 2.99 |
| W/pCADA107 | 1.87 | 3.02 |
| W/pCADA108 | 1.14 | 2.72 |
| W/pCADA109 | 1.35 | 2.95 |
| W/pCADA110 | 1.34 | 2.91 |
| W/pCADA111 | 1.38 | 2.89 |
| W/pCADA112 | 1.24 | 2.85 |
| W/pCADA113 | 1.25 | 2.79 |
| W/pCADA114 | 1.23 | 2.83 |
| W/pCADA115 | 1.31 | 2.84 |
| W/pCADA116 | 1.13 | 2.80 |
| W/pCADA117 | 1.24 | 2.94 |
| W/pCADA118 | 1.53 | 2.82 |
| W/pCADA119 | 1.48 | 2.75 |

The values in Tables 30 to 34 show concentration, and are relative values setting the concentration of W/pCADA1 of the control test region as 1.

W/pCADA1, W/pCADA75, W/pCADA95, W/pCADA113, and W/pCADA117 obtained in Reference Example 1 and Example 2 were inoculated into 500 ml of a LB medium containing 100 μg/mL of Am in a 2 L Erlenmeyer flask having a baffle, and culture was conducted with shaking at 30° C. for 26.5 hours. Thereafter, the culture solution was subjected to centrifugal separation at 8000 rpm for 10 minutes. The bacterial cells were collected, and the collected bacterial cells were suspended in water, thereby preparing a bacterial cell suspension having a dry bacterial cell-based concentration of 12.5 wt %. The bacterial cell suspension was incubated in a warm water bath of a temperature of 58° C. for 30 minutes, thereby giving a heat treatment; and cryopreserved at −20° C. until use. Then, to 540 g of a liquid in which lysine hydrochloride (Wako) was dissolved in fermentation liquid A prepared by the method described in Reference Example 4 to be 45 mass %, 4.5 g of 0.4% PLP aqueous solution was added, and further 0.1 g of ADEKA NOL LG129 was added, and the mixture was stirred at 200 rpm. Five such reaction solutions were prepared, and the catalyst inactivated bacterial cells of the above-described W/pCADA1, W/pCADA75, W/pCADA95, W/pCADA113, and W/pCADA117 were added, respectively, in an amount of 0.139 g based on dry bacterial cell. Reaction was conducted for 24 hours at 35° C. for W/pCADA75, and at 45° C. for W/pCADA1, W/pCADA95, W/pCADA113, and W/pCADA117. The results are shown in Table 35.

TABLE 35

| Time | W/pCADA1 | W/pCADA75 | W/pCADA95 | W/pCADA113 | W/pCADA117 |
|---|---|---|---|---|---|
| 17.0 | 87.045% | 96.799% | 93.311% | 92.134% | 97.409% |
| 19.0 | 89.043% | 97.357% | 94.192% | 93.570% | 97.747% |
| 21.0 | 90.246% | 97.896% | 95.329% | 94.325% | 98.345% |
| 24.0 | 91.811% | 98.322% | 96.203% | 95.915% | 98.904% |

W/pCADA1, W/pCADA120, W/pCADA121, and W/pCADA122 obtained in Reference Example 1 and Example 3 were inoculated into 500 ml of a LB medium containing 100 μg/mL of Am in a 2 L Erlenmeyer flask having a baffle, and culture was conducted with shaking at 30° C. for 26.5 hours. Thereafter, the culture solution was subjected to centrifugal separation at 8000 rpm for 10 minutes. The bacterial cells were collected, and the collected bacterial cells were suspended in water, thereby preparing a bacterial cell suspension having a dry bacterial cell-based concentration of 12.5 wt %. The bacterial cell suspension was incubated in a warm water bath of a temperature of 58° C. for 30 minutes, thereby giving a heat treatment; and cryopreserved at −20° C. until use. Then, to 540 g of a liquid in which lysine hydrochloride (Wako) was dissolved in fermentation liquid A prepared by the method described in Reference Example 4 to be 45 mass %, 4.5 g of 0.4% PLP aqueous solution was added, and further 0.1 g of ADEKA NOL LG129 was added, and the mixture was stirred at 200 rpm. Three such reaction solutions were prepared, and the catalyst inactivated bacterial cells of the above-described W/pCADA1, W/pCADA120, W/pCADA121, and W/pCADA122 were added, respectively, in an amount of 0.139 g based on dry bacterial cell. Reaction was conducted for 24 hours at 35° C. for W/pCADA120, and at 45° C. for W/pCADA1, W/pCADA121, and W/pCADA122. The results are shown in Table 36.

TABLE 36

|  | W/pCADA1 | W/pCADA120 | W/pCADA121 | W/pCADA122 |
|---|---|---|---|---|
| 17.0 | 87.045% | 98.662% | 98.104% | 98.810% |
| 19.0 | 89.043% | 98.827% | 98.440% | 99.120% |
| 21.0 | 90.246% | 98.959% | 98.858% | 99.321% |
| 24.0 | 91.811% | 99.158% | 98.951% | 99.310% |

Example 11

[High Concentration Accumulation Reaction]

To a 300 mL flask, 120 g of a substrate solution was added: the substrate solution was prepared so that the final L-lysine hydrochloride concentration was 45 mass % and the final pyridoxal phosphate concentration was 0.15 mM. Next, the *Corynebacterium* described in Reference Example 5 was added to be $2.5 \times 10^7$ cell/mL, the catalyst inactivated bacterial cell of W/pCAD21 prepared in Example 3 (0.0648 g based on dry bacterial cell weight, bacterial cell activity 164 unit/mg dry bacterial cell) was added, and reaction was performed at 42° C. and 200 rpm for 24 hours. The reaction yield was 99%.

Example 12

[Production of 1,5-Pentamethylene Diisocyanate]

(Purification of PDA Produced from Lysine Fermentation Liquid)

To the reaction solution, 25 µL of catalyst inactivated bacterial cell of Reference Example 8 shown in Table 17 was added; the pH of the reaction solution was adjusted with sulfuric acid to 6.0; and the reaction solution was subjected to centrifugal separation at 8000 rpm for 20 minutes, thereby removing precipitate such as bacterial cells. The solution was passed through a column charged with cation exchange resin (Dowex 50WX8 (H+ type)), and 1,5-pentamethylenediamine was adsorbed onto the cation exchange resin. Thereafter, a 0.7M solution of sodium chloride was passed through the column to sufficiently wash resin and to remove impurities, and the adsorbed 1,5-pentamethylenediamine was eluted with 6N hydrochloric acid. The pH was adjusted to 12 by adding a 30% sodium hydroxide solution to the eluate.

(Condensation of Purified PDA)

A separatory funnel was charged with 100 parts by mass of an aqueous solution of 1,5-pentamethylenediamine and 100 parts by mass of n-butanol (extractant), and the mixture was mixed for 10 minutes. Thereafter, the mixture was allowed to stand for 30 minutes. Then, the organic phase (n-butanol containing 1,5-pentamethylenediamine) was discharged.

Then, a four-neck flask equipped with a thermometer, a distillation column, a condenser tube, and a nitrogen inlet tube was charged with 100 parts by mass of the extract of the organic phase (n-butanol containing 1,5-pentamethylenediamine), and with an oil bath temperature of 120° C. and under a reduced pressure of 100 kPa, n-butanol was distilled off, thereby producing 1,5-pentamethylenediamine having a purity of 99.9 mass %.

Similarly, 1,5-pentamethylenediamine was produced from 24 th hour W/pCADA75 of Table 35, and 24 th hour W/pCADA122 of Table 36 of Example 10 as starting materials.

(Synthesis of PDI)

A pressurized reactor with jacket equipped with an electromagnetic induction stirrer, an automatic pressure regulating valve, a thermometer, a nitrogen inlet line, a phosgene inlet line, a condenser, and a material feed pump was charged with 2000 parts by mass of o-dichlorobenzene. Then, 2300 parts by mass of phosgene was added from the phosgene inlet line, and stirring was started. Cold water was allowed to go through the reactor jacket so that the internal temperature was kept to about 10° C. Then, a solution of 400 parts by mass of pentamethylenediamine dissolved in 2600 parts by mass of o-dichlorobenzene was fed through the feed pump taking 60 minutes, and cold phosgenation was started at 30° C. or less and under normal pressure. After the completion of the feed, a light-brown white slurry was formed in the pressurized reactor.

Then, while the temperature of the internal liquid of the reactor was gradually increased to 160° C., the pressure was increased to 0.25 MPa, and further hot phosgenation was performed under a pressure of 0.25 MPa, and at a reaction temperature of 160° C. for 90 minutes. During the hot phosgenation, 1100 parts by mass of phosgene was further added. In the process of the hot phosgenation, the internal liquid of the pressurized reactor became light-brown clear solution. After completion of hot phosgenation, at 100 to 140° C., nitrogen gas was allowed to pass through at 100 L/hour, and degassing was performed.

Thereafter, o-dichlorobenzene was distilled off under reduced pressure, and then pentamethylene diisocyanate was distilled off also under reduced pressure.

Then, a four-neck flask equipped with a mixer, a thermometer, a reflux pipe, and a nitrogen inlet tube was charged with the distilled pentamethylene diisocyanate, and while introducing nitrogen, heat treatment was performed under normal pressure, at 190° C. for 3 hours.

Then, pentamethylene diisocyanate after heat treatment was introduced to a glass-made flask, and using a distillation apparatus equipped with a distillation pipe charged with packing materials, a distillation column having a reflux ratio adjusting timer, and a condenser, the pentamethylene diisocyanate was rectified while further being refluxed under the conditions of 127 to 132° C. and 2.7 KPa, thereby producing 450 parts by mass of pentamethylene diisocyanate having a purity of 99.8 mass %.

Pentamethylene diisocyanate was produced in the same manner also using 24 th hour W/pCADA75 of Table 35 and 24 th hour W/pCADA122 of Table 36 of Example 10 as starting materials.

Example 13

[Production of Polyisocyanate Composition]

A four-neck flask equipped with a mixer, a thermometer, a reflux pipe, and a nitrogen inlet tube was charged with 500 parts by mass of pentamethylene diisocyanate obtained as described above, 3.9 parts by mass of 1,3-butanediol (hereinafter may be referred to as 1,3-BG), 0.25 parts by mass of 2,6-di(tert-butyl)-4-methylphenol, and 0.25 parts by mass of tris (tridecyl) phosphite, and reaction was performed at 80° C. for 3 hours. After decreasing the temperature of the solution to 60° C., 0.1 parts by mass of N-(2-hydroxypropyl)-N,N,N-trimethylammonium-2-ethylhexanoate was added as a trimerization catalyst. After conducting reaction for 1 hour, 0.12 parts by mass of o-toluenesulfonamide was added (conversion rate of isocyanate group: 10 mass %). The obtained reaction solution was allowed to pass through a thin film distillation apparatus (degree of vacuum 0.093

KPa, temperature 150° C.) to remove unreacted pentamethylene diisocyanate, and 0.02 parts by mass of o-toluenesulfonamide relative to 100 parts by mass of the obtained composition was further added, thereby producing a polyisocyanate composition.

The polyisocyanate composition had a pentamethylene diisocyanate concentration of 0.4 mass %, an isocyanate trimer concentration of 46 mass %, an isocyanate group concentration of 24.0 mass %, a viscosity at 25° C. of 1930 mPa·s, and a color of APHA 20.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY 1,5-pentamethylenediamine produced by using the method for producing 1,5-pentamethylenediamine and mutant lysine decarboxylase of the present invention can be suitably used in various industrial fields such as, for example, biomass-derived polymer materials and intermediates for agricultural chemicals and pharmaceutical products.

The invention claimed is:

1. A mutant lysine decarboxylase, wherein one amino acid residue to five amino acid residues are replaced in the amino acid sequence of SEQ ID NO: 4, wherein the amino acid to be replaced with another amino acid is present in a decamer forming domain and an activation region domain, in the amino acid sequence of SEQ ID NO:4, and wherein of the amino acids present in the decamer forming domain, amino acid at position 14 is changed from Phe to Gln, amino acid at position 39 is changed from Arg to Ile, amino acid at position 39 is changed from Arg to Val, amino acid at position 88 is changed from Thr to Lys, amino acid at position 88 is changed from Thr to Arg, amino acid at position 88 is changed from Thr to Asn, amino acid at position 139 is changed from Tyr to Val, amino acid at position 139 is changed from Tyr to Cys, amino acid at position 139 is changed from Tyr to Thr, amino acid at position 139 is changed from Tyr to Ser, and amino acid at position 139 is changed from Tyr to Asn and of the amino acids present in the activation region domain, amino acid at position 184 is changed from Val to Ala, amino acid at position 253 is changed from Met to Leu, amino acid at position 262 is changed from Phe to Tyr, amino acid at position 286 is changed from Ala to Asp, amino acid at position 295 is changed from Ala to Ser, amino acid at position 303 is changed from Ile to Thr, amino acid at position 317 is changed from Phe to Gln, amino acid at position 335 is changed from Pro to Ala, amino acid at position 353 is changed from Arg to His, amino acid at position 386 is changed from Glu to Ser, amino acid at position 430 is changed from Glu to Phe, amino acid at position 443 is changed from Arg to Met, amino acid at position 446 is changed from Ser to Tyr, amino acid at position 446 is changed from Ser to Gln, amino acid at position 460 is changed from Asp to Ile, amino acid at position 460 is changed from Asp to Asn, amino acid at position 460 is changed from Asp to Cys, amino acid at position 460 is changed from Asp to Gln, amino acid at position 460 is changed from Asp to Pro, amino acid at position 460 is changed from Asp to Ser, amino acid at position 466 is changed from Pro to Asn, amino acid at position 466 is changed from Pro to Gly, amino acid at position 466 is changed from Pro to Ser, amino acid at position 471 is changed from Ser to Tyr, amino acid at position 475 is changed from Gly to Asn, amino acid at position 506 is changed from Asp to Pro, amino acid at position 524 is changed from Val to Leu, amino acid at position 539 is changed from Ile to Cys, amino acid at position 539 is changed from Ile to Leu, amino acid at position 544 is changed from Thr to Ala, amino acid at position 544 is changed from Thr to Ser, amino acid at position 544 is changed from Thr to Pro, amino acid at position 546 is changed from Ala to Ser, amino acid at position 553 is changed from Leu to Val, amino acid at position 623 is changed from Ala to Cys, amino acid at position 623 is changed from Ala to Phe, amino acid at position 623 is changed from Ala to Gln, amino acid at position 626 is changed from Lys to Val, amino acid at position 636 is changed from Tyr to Cys, amino acid at position 636 is changed from Tyr to Pro, amino acid at position 646 is changed from Ala to Leu, amino acid at position 646 is changed from Ala to Ile, amino acid at position 648 is changed from Met to Ser, amino acid at position 710 is changed from Lys to Thr, and amino acid at position 711 is changed from Glu to Asp.

2. The mutant lysine decarboxylase of claim 1, wherein the decamer forming domain is a wing domain and/or a linker domain, and the activation region domain is a pyridoxal phosphate enzyme co-domain and/or a substrate entrance/exit,
wherein one amino acid residue to five amino acid residues in the amino acid sequence of SEQ ID NO:4 are replaced,
wherein of the amino acids present in the wing domain, amino acid at position 64 is changed from Leu to Lys, amino acid at position 67 is changed from Cys to Thr, amino acid at position 67 is changed from Cys to Leu, amino acid at position 70 is changed from Ile to Leu, amino acid at position 70 is changed from Ile to Pro, amino acid at position 75 is changed from Glu to Pro, amino acid at position 75 is changed from Glu to His, amino acid at position 79 is changed from Leu to Ile, amino acid at position 83 is changed from Ala to Leu, amino acid at position 83 is changed from Ala to Ile, amino acid at position 84 is changed from Asn to Asp, amino acid at position 84 is changed from Asn to Thr, amino acid at position 89 is changed from Leu to Phe, amino acid at position 94 is changed from Asn to Ile, amino acid at position 95 is changed from Asp to Pro, amino acid at position 98 is changed from Leu to Ile, amino acid at position 99 is changed from Gln to Thr, amino acid at position 104 is changed from Glu to Asn, amino acid at position 104 is changed from Glu to Lys, amino acid at position 112 is changed from Asp to Glu, amino acid at position 119 is changed from Gln to Asn, amino acid at position 119 is changed from Gln to Ile, amino acid at position 119 is changed from Gln to Thr, and amino acid at position 119 is changed from Gln to Ser,
wherein of the amino acids present in the linker domain, amino acid at position 137 is changed from Phe to Val, amino acid at position 138 is changed from Lys to Ile, amino acid at amino acid at position 143 is changed from Gly to Glu, amino acid at position 145 is changed from Tyr to Arg, amino acid at position 148 is changed from Cys to Ser, amino acid at position 148 is changed from Cys to Ala, and amino acid at position 182 is changed from Ile to Met,
wherein of the amino acids present in the pyridoxal phosphate enzyme co-domain, amino acid at position 184 is changed from Val to Ala, amino acid at position 253 is changed from Met to Leu, amino acid at position 262 is changed from Phe to Tyr, amino acid at position 286 is changed from Ala to Asp, amino acid at position 295 is changed from Ala to Ser, amino acid at position 303 is changed from Ile to Thr, amino acid at position 317 is changed from Phe to Gln, amino acid at position 335 is changed from Pro to Ala, amino acid at position 353 is changed from Arg to His, and amino acid at position 386 is changed from Glu to Ser, and
wherein of the amino acids present in the substrate entrance/exit, amino acid at position 430 is changed from Glu to Phe, amino acid at position 443 is changed from Arg to Met, amino acid at position 446 is changed from Ser to Tyr, amino acid at position 446 is changed from Ser to Gln, amino acid at position 460 is changed from Asp to Ile, amino acid at position 460 is changed from Asp to Asn, amino acid at position 460 is changed from Asp to Cys, amino acid at position 460 is changed from Asp to Gln, amino acid at position 460 is changed from Asp to Pro, amino acid at position 460 is changed from Asp to Ser, amino acid at position 466 is changed from Pro to Asn, amino acid at position 466 is changed from Pro to Gly, amino acid at position 466 is changed from Pro to Ser, amino acid at position 471 is changed from Ser to Tyr, amino acid at position 475 is changed from Gly to Asn, amino acid at position 506 is changed from Asp to Pro, amino acid at position 524 is changed from Val to Leu, amino acid at position 539 is changed from Ile to Cys, amino acid at position 539 is changed from Ile to Leu, amino acid at position 544 is changed from Thr to Ala, amino acid at position 544 is changed from Thr to Ser, amino acid at position 544 is changed from Thr to Pro, amino acid at position 546 is changed from Ala to Ser, amino acid at position 553 is changed from Leu to Val, amino acid at position 623 is changed from Ala to Cys, amino acid at position 623 is changed from Ala to Phe, amino acid at position 623 is changed from Ala to Gln, amino acid at position 626 is changed from Lys to Val, amino acid at position 636 is changed from Tyr to Cys, amino acid at position 636 is changed from Tyr to Pro, amino acid at position 646 is changed from Ala to Leu, amino acid at position 646 is changed from Ala to Ile, amino acid at position 648 is changed from Met to Ser, amino acid at position 710 is changed from Lys to Thr, and amino acid at position 711 is changed from Glu to Asp.

3. The mutant lysine decarboxylase according to of claim 1 wherein in the amino acid sequence of SEQ ID NO:4, the amino acids at positions 148 and 646 are replaced with other amino acids.

4. The mutant lysine decarboxylase of claim 1, wherein in the amino acid sequence of SEQ ID NO:4, the amino acids at positions 471 and 626 are replaced with other amino acids.

5. The mutant lysine decarboxylase of claim 1 wherein in the amino acid sequence of SEQ ID NO:4, the amino acids at positions 626 and 646 are replaced with other amino acids.

* * * * *

SEQUENCE LISTING

```
<160> NUMBER OF SEQ ID NOS: 240

<210> SEQ ID NO 1
<211> LENGTH: 47
<212> TYPE: DNA
<213> ORGANISM: Artificial
<220> FEATURE:
<223> OTHER INFORMATION: primer

<400> SEQUENCE: 1
aaggtaccac aaaaaggata aaacaatgaa cgttattgca atattga            47

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
agtctagatt atttttgct ttcttctttc                                30

<210> SEQ ID NO 3
<211> LENGTH: 2148
<212> TYPE: DNA
<213> ORGANISM: Escherichia coli
<220> FEATURE:
<221> NAME/KEY: CDS
<222> LOCATION: (1)..(2148)
<223> OTHER INFORMATION: (none)

<400> SEQUENCE: 3 atg aac gtt att gca ata ttg aat cac atg ggg gtt tat ttt aaa gaa    48
Met Asn Val Ile Ala Ile Leu Asn His Met Gly Val Tyr Phe Lys Glu
1               5                   10                  15 gaa ccc atc cgt gaa ctt cat cgc gcg ctt gaa cgt ctg aac ttc cag    96
Glu Pro Ile Arg Glu Leu His Arg Ala Leu Glu Arg Leu Asn Phe Gln
                20                  25                  30 att gtt tac ccg aac gac cgt gac gac tta tta aaa ctg atc gaa aac   144
Ile Val Tyr Pro Asn Asp Arg Asp Asp Leu Leu Lys Leu Ile Glu Asn
            35                  40                  45 aat gcg cgt ctg tgc ggc gtt att ttt gac tgg gat aaa tat aat ctc   192
Asn Ala Arg Leu Cys Gly Val Ile Phe Asp Trp Asp Lys Tyr Asn Leu
        50                  55                  60 gag ctg tgc gaa gaa att agc aaa atg aac gag aac ctg ccg ttg tac   240
Glu Leu Cys Glu Glu Ile Ser Lys Met Asn Glu Asn Leu Pro Leu Tyr
65                  70                  75                  80 gcg ttc gct aat acg tat tcc act ctc gat gta agc ctg aat gac ctg   288
Ala Phe Ala Asn Thr Tyr Ser Thr Leu Asp Val Ser Leu Asn Asp Leu
                85                  90                  95
```

```
cgt tta cag att agc ttc ttt gaa tat gcg ctg ggt gct gct gaa gat    336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att    384
Ile Ala Asn Lys Ile Lys Gln Thr Thr Asp Glu Tyr Ile Asn Thr Ile
            115                 120                 125 ctg cct ccg ctg act aaa gca ctg ttt aaa tat gtt cgt gaa ggt aaa    432
Leu Pro Pro Leu Thr Lys Ala Leu Phe Lys Tyr Val Arg Glu Gly Lys
            130                 135                 140 tat act ttc tgt act cct ggt cac atg ggc ggt act gca ttc cag aaa    480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg    528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat    576
Lys Ser Asp Ile Ser Ile Ser Val Ser Glu Leu Gly Ser Leu Leu Asp
                180                 185                 190 cac agt ggt cca cac aaa gaa gca gaa cag tat atc gct cgc gtc ttt    624
His Ser Gly Pro His Lys Glu Ala Glu Gln Tyr Ile Ala Arg Val Phe
                195                 200                 205 aac gca gac cgc agc tac atg gtg acc aac ggt act tcc act gcg aac    672
Asn Ala Asp Arg Ser Tyr Met Val Thr Asn Gly Thr Ser Thr Ala Asn
210                 215                 220 aaa att gtt ggt atg tac tct gct cca gca ggc agc acc att ctg att    720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg atg agc gat    768
Asp Arg Asn Cys His Lys Ser Leu Thr His Leu Met Met Met Ser Asp
                245                 250                 255 gtt acg cca atc tat ttc cgc ccg acc cgt aac gct tac ggt att ctt    816
Val Thr Pro Ile Tyr Phe Arg Pro Thr Arg Asn Ala Tyr Gly Ile Leu
                260                 265                 270 ggt ggt atc cca cag agt gaa ttc cag cac gct acc att gct aag cgc    864
Gly Gly Ile Pro Gln Ser Glu Phe Gln His Ala Thr Ile Ala Lys Arg
                275                 280                 285 gtg aaa gaa aca cca aac gca acc tgg ccg gta cat gct gta att acc    912
Val Lys Glu Thr Pro Asn Ala Thr Trp Pro Val His Ala Val Ile Thr
290                 295                 300 aac tct acc tat gat ggt ctg ctg tac aac acc gac ttc atc aag aaa    960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac   1008
Thr Leu Asp Val Lys Ser Ile His Phe Asp Ser Ala Trp Val Pro Tyr
                325                 330                 335 acc aac ttc tca ccg att tac gaa ggt aaa tgc ggt atg agc ggt ggc   1056
Thr Asn Phe Ser Pro Ile Tyr Glu Gly Lys Cys Gly Met Ser Gly Gly
                340                 345                 350 cgt gta gaa ggg aaa gtg att tac gaa acc cag tcc act cac aaa ctg   1104
Arg Val Glu Gly Lys Val Ile Tyr Glu Thr Gln Ser Thr His Lys Leu
                355                 360                 365 ctg gcg gcg ttc tct cag gct tcc atg atc cac gtt aaa ggt gac gta   1152
Leu Ala Ala Phe Ser Gln Ala Ser Met Ile His Val Lys Gly Asp Val
370                 375                 380 aac gaa gaa acc ttt aac gaa gcc tac atg atg cac acc acc act tct   1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg   1248
Pro His Tyr Gly Ile Val Ala Ser Thr Glu Thr Ala Ala Ala Met Met
                405                 410                 415
```

```
aaa ggc aat gca ggt aag cgt ctg atc aac ggt tct att gaa cgt gcg     1296
Lys Gly Asn Ala Gly Lys Arg Leu Ile Asn Gly Ser Ile Glu Arg Ala
            420                 425                 430 atc aaa ttc cgt aaa gag atc aaa cgt ctg aga acg gaa tct gat ggc     1344
Ile Lys Phe Arg Lys Glu Ile Lys Arg Leu Arg Thr Glu Ser Asp Gly
        435                 440                 445 tgg ttc ttt gat gta tgg cag ccg gat cat atc gat acg act gaa tgc    1392
Trp Phe Phe Asp Val Trp Gln Pro Asp His Ile Asp Thr Thr Glu Cys
450                 455                 460 tgg ccg ctg cgt tct gac agc acc tgg cac ggc ttc aaa aac atc gat    1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg    1488
Asn Glu His Met Tyr Leu Asp Pro Ile Lys Val Thr Leu Leu Thr Pro
            485                 490                 495 ggg atg gaa aaa gac ggc acc atg agc gac ttt ggt att ccg gcc agc    1536
Gly Met Glu Lys Asp Gly Thr Met Ser Asp Phe Gly Ile Pro Ala Ser
        500                 505                 510 atc gtg gcg aaa tac ctc gac gaa cat ggc atc gtt gtt gag aaa acc    1584
Ile Val Ala Lys Tyr Leu Asp Glu His Gly Ile Val Val Glu Lys Thr
    515                 520                 525 ggt ccg tat aac ctg ctg ttc ctg ttc agc atc ggt atc gat aag acc    1632
Gly Pro Tyr Asn Leu Leu Phe Leu Phe Ser Ile Gly Ile Asp Lys Thr
530                 535                 540 aaa gca ctg agc ctg ctg cgt gct ctg act gac ttt aaa cgt gcg ttc    1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa    1728
Asp Leu Asn Leu Arg Val Lys Asn Met Leu Pro Ser Leu Tyr Arg Glu
            565                 570                 575 gat cct gaa ttc tat gaa aac atg cgt att cag gaa ctg gct cag aat    1776
Asp Pro Glu Phe Tyr Glu Asn Met Arg Ile Gln Glu Leu Ala Gln Asn
        580                 585                 590 atc cac aaa ctg att gtt cac cac aat ctg ccg gat ctg atg tat cgc    1824
Ile His Lys Leu Ile Val His His Asn Leu Pro Asp Leu Met Tyr Arg
    595                 600                 605 gca ttt gaa gtg ctg ccg acg atg gta atg act ccg tat gct gca ttc    1872
Ala Phe Glu Val Leu Pro Thr Met Val Met Thr Pro Tyr Ala Ala Phe
610                 615                 620 cag aaa gag ctg cac ggt atg acc gaa gaa gtt tac ctc gac gaa atg    1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt    1968
Val Gly Arg Ile Asn Ala Asn Met Ile Leu Pro Tyr Pro Pro Gly Val
            645                 650                 655 cct ctg gta atg ccg ggt gaa atg atc acc gaa gaa agc cgt ccg gtt    2016
Pro Leu Val Met Pro Gly Glu Met Ile Thr Glu Glu Ser Arg Pro Val
        660                 665                 670 ctg gag ttc ctg cag atg ctg tgt gaa atc ggc gct cac tat ccg ggc    2064
Leu Glu Phe Leu Gln Met Leu Cys Glu Ile Gly Ala His Tyr Pro Gly
    675                 680                 685 ttt gaa acc gat att cac ggt gca tac cgt cag gct gat ggc cgc tat    2112
Phe Glu Thr Asp Ile His Gly Ala Tyr Arg Gln Ala Asp Gly Arg Tyr
690                 695                 700 acc gtt aag gta ttg aaa gaa gaa agc aaa aaa taa                    2148
Thr Val Lys Val Leu Lys Glu Glu Ser Lys Lys
705                 710                 715
```

<210> SEQ ID NO 4

-continued

```
<211> LENGTH: 715
<212> TYPE: PRT
<213> ORGANISM: Escherichia coli

<400> SEQUENCE: 4

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
```

-continued

```
                385                 390                 395                 400
        Pro His Tyr Gly Ile Val Ala Ser Thr Glu Thr Ala Ala Ala Met Met
                            405                 410                 415

Lys Gly Asn Ala Gly Lys Arg Leu Ile Asn Gly Ser Ile Glu Arg Ala
                        420                 425                 430

Ile Lys Phe Arg Lys Glu Ile Lys Arg Leu Arg Thr Glu Ser Asp Gly
                    435                 440                 445

Trp Phe Phe Asp Val Trp Gln Pro Asp His Ile Asp Thr Thr Glu Cys
                450                 455                 460

Trp Pro Leu Arg Ser Asp Ser Thr Trp His Gly Phe Lys Asn Ile Asp
        465                 470                 475                 480

Asn Glu His Met Tyr Leu Asp Pro Ile Lys Val Thr Leu Leu Thr Pro
                            485                 490                 495

Gly Met Glu Lys Asp Gly Thr Met Ser Asp Phe Gly Ile Pro Ala Ser
                        500                 505                 510

Ile Val Ala Lys Tyr Leu Asp Glu His Gly Ile Val Val Glu Lys Thr
                    515                 520                 525

Gly Pro Tyr Asn Leu Leu Phe Leu Phe Ser Ile Gly Ile Asp Lys Thr
                530                 535                 540

Lys Ala Leu Ser Leu Leu Arg Ala Leu Thr Asp Phe Lys Arg Ala Phe
        545                 550                 555                 560

Asp Leu Asn Leu Arg Val Lys Asn Met Leu Pro Ser Leu Tyr Arg Glu
                            565                 570                 575

Asp Pro Glu Phe Tyr Glu Asn Met Arg Ile Gln Glu Leu Ala Gln Asn
                        580                 585                 590

Ile His Lys Leu Ile Val His His Asn Leu Pro Asp Leu Met Tyr Arg
                    595                 600                 605

Ala Phe Glu Val Leu Pro Thr Met Val Met Thr Pro Tyr Ala Ala Phe
                610                 615                 620

Gln Lys Glu Leu His Gly Met Thr Glu Val Tyr Leu Asp Glu Met
        625                 630                 635                 640

Val Gly Arg Ile Asn Ala Asn Met Ile Leu Pro Tyr Pro Pro Gly Val
                            645                 650                 655

Pro Leu Val Met Pro Gly Glu Met Ile Thr Glu Glu Ser Arg Pro Val
                        660                 665                 670

Leu Glu Phe Leu Gln Met Leu Cys Glu Ile Gly Ala His Tyr Pro Gly
                    675                 680                 685

Phe Glu Thr Asp Ile His Gly Ala Tyr Arg Gln Ala Asp Gly Arg Tyr
                690                 695                 700

Thr Val Lys Val Leu Lys Glu Glu Ser Lys Lys
        705                 710                 715

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
gactaaagca ctggtcaaat atgttcgtg                                         29

<210> SEQ ID NO 6
<211> LENGTH: 29
<212> TYPE: DNA
<213> ORGANISM: Artificial
```

```
<220> FEATURE:
<223> OTHER INFORMATION: primer

<400> SEQUENCE: 6
cacgaacata tttgaccagt gctttagtc                                29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
taaagcactg tttatctatg ttcgtgaag                                29

<210> SEQ ID NO 8
<211> LENGTH: 29
<212> TYPE: DNA
<213> ORGANISM: Artificial
<220> FEATURE:
<223> OTHER INFORMATION: primer

<400> SEQUENCE: 8
cttcacgaac atagataaac agtgcttta                                29

<210> SEQ ID NO 9
<211> LENGTH: 29
<212> TYPE: DNA
<213> ORGANISM: Artificial
<220> FEATURE:
<223> OTHER INFORMATION: primer

<400> SEQUENCE: 9
gcacgctacc attgacaagc gcgtgaaag                                29

<210> SEQ ID NO 10
<211> LENGTH: 29
<212> TYPE: DNA
<213> ORGANISM: Artificial
<220> FEATURE:
<223> OTHER INFORMATION: primer

<400> SEQUENCE: 10
ctttcacgcg cttgtcaatg gtagcgtgc                                29

<210> SEQ ID NO 11
<211> LENGTH: 29
<212> TYPE: DNA
<213> ORGANISM: Artificial
<220> FEATURE:
<223> OTHER INFORMATION: primer

<400> SEQUENCE: 11
tgctaagcgc gtgcacgaaa caccaaacg                                29

<210> SEQ ID NO 12
<211> LENGTH: 29
<212> TYPE: DNA
<213> ORGANISM: Artificial
<220> FEATURE:
<223> OTHER INFORMATION: primer

<400> SEQUENCE: 12
cgtttggtgt ttcgtgcacg cgcttagca                                29
```

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13
agaaacacca aactcaacct ggccggtac                                29

<210> SEQ ID NO 14
<211> LENGTH: 29
<212> TYPE: DNA
<213> ORGANISM: Artificial
<220> FEATURE:
<223> OTHER INFORMATION: primer

<400> SEQUENCE: 14
gtaccggcca ggttgagttt ggtgtttct                                29

<210> SEQ ID NO 15
<211> LENGTH: 29
<212> TYPE: DNA
<213> ORGANISM: Artificial
<220> FEATURE:
<223> OTHER INFORMATION: primer

<400> SEQUENCE: 15
ggtacatgct gtaacaacca actctacct                                29

<210> SEQ ID NO 16
<211> LENGTH: 29
<212> TYPE: DNA
<213> ORGANISM: Artificial
<220> FEATURE:
<223> OTHER INFORMATION: primer

<400> SEQUENCE: 16
aggtagagtt ggttgttaca gcatgtacc                                29

<210> SEQ ID NO 17
<211> LENGTH: 29
<212> TYPE: DNA
<213> ORGANISM: Artificial
<220> FEATURE:
<223> OTHER INFORMATION: primer

<400> SEQUENCE: 17
gtacaacacc gaccagatca agaaaacac                                29

<210> SEQ ID NO 18
<211> LENGTH: 29
<212> TYPE: DNA
<213> ORGANISM: Artificial
<220> FEATURE:
<223> OTHER INFORMATION: primer

<400> SEQUENCE: 18
gtgttttctt gatctggtcg gtgttgtac                                29

<210> SEQ ID NO 19
<211> LENGTH: 29
<212> TYPE: DNA
<213> ORGANISM: Artificial
<220> FEATURE:
<223> OTHER INFORMATION: primer

<400> SEQUENCE: 19
ctccgcgtgg gtggcttaca ccaacttct                               29

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
agaagttggt gtaagccacc cacgcggag                               29

<210> SEQ ID NO 21
<211> LENGTH: 29
<212> TYPE: DNA
<213> ORGANISM: Artificial
<220> FEATURE:
<223> OTHER INFORMATION: primer

<400> SEQUENCE: 21
cggtatgagc ggtgcacgtg tagaaggga                               29

<210> SEQ ID NO 22
<211> LENGTH: 29
<212> TYPE: DNA
<213> ORGANISM: Artificial
<220> FEATURE:
<223> OTHER INFORMATION: primer

<400> SEQUENCE: 22
tcccttctac acgtgcaccg ctcataccg                               29

<210> SEQ ID NO 23
<211> LENGTH: 29
<212> TYPE: DNA
<213> ORGANISM: Artificial
<220> FEATURE:
<223> OTHER INFORMATION: primer

<400> SEQUENCE: 23
tatgagcggt ggccatgtag aagggaaag                               29

<210> SEQ ID NO 24
<211> LENGTH: 29
<212> TYPE: DNA
<213> ORGANISM: Artificial
<220> FEATURE:
<223> OTHER INFORMATION: primer

<400> SEQUENCE: 24
ctttcccttc tacatggcca ccgctcata                               29

<210> SEQ ID NO 25
<211> LENGTH: 29
<212> TYPE: DNA
<213> ORGANISM: Artificial
<220> FEATURE:
<223> OTHER INFORMATION: primer

<400> SEQUENCE: 25
aggtgacgta aactccgaaa cctttaacg                               29

<210> SEQ ID NO 26

-continued

<211> LENGTH: 29
<212> TYPE: DNA
<213> ORGANISM: Artificial
<220> FEATURE:
<223> OTHER INFORMATION: primer

<400> SEQUENCE: 26
cgttaaaggt tcggagttt acgtcacct                                29

<210> SEQ ID NO 27
<211> LENGTH: 29
<212> TYPE: DNA
<213> ORGANISM: Artificial
<220> FEATURE:
<223> OTHER INFORMATION: primer

<400> SEQUENCE: 27
gatcaaacgt ctgatgacgg aatctgatg                                29

<210> SEQ ID NO 28
<211> LENGTH: 29
<212> TYPE: DNA
<213> ORGANISM: Artificial
<220> FEATURE:
<223> OTHER INFORMATION: primer

<400> SEQUENCE: 28
catcagattc cgtcatcaga cgtttgatc                                29

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
gactgaatgc tggaacctgc gttctgaca                                29

<210> SEQ ID NO 30
<211> LENGTH: 29
<212> TYPE: DNA
<213> ORGANISM: Artificial
<220> FEATURE:
<223> OTHER INFORMATION: primer

<400> SEQUENCE: 30
tgtcagaacg caggttccag cattcagtc                                29

<210> SEQ ID NO 31
<211> LENGTH: 29
<212> TYPE: DNA
<213> ORGANISM: Artificial
<220> FEATURE:
<223> OTHER INFORMATION: primer

<400> SEQUENCE: 31
gactgaatgc tggggcctgc gttctgaca                                29

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
tgtcagaacg caggccccag cattcagtc                                29

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33
gactgaatgc tggtctctgc gttctgaca                                29

<210> SEQ ID NO 34
<211> LENGTH: 29
<212> TYPE: DNA
<213> ORGANISM: Artificial
<220> FEATURE:
<223> OTHER INFORMATION: primer

<400> SEQUENCE: 34
tgtcagaacg cagagaccag cattcagtc                                29

<210> SEQ ID NO 35
<211> LENGTH: 29
<212> TYPE: DNA
<213> ORGANISM: Artificial
<220> FEATURE:
<223> OTHER INFORMATION: primer

<400> SEQUENCE: 35
cagcacctgg cacaatttca aaaacatcg                                29

<210> SEQ ID NO 36
<211> LENGTH: 29
<212> TYPE: DNA
<213> ORGANISM: Artificial
<220> FEATURE:
<223> OTHER INFORMATION: primer

<400> SEQUENCE: 36
cgatgttttt gaaattgtgc caggtgctg                                29

<210> SEQ ID NO 37
<211> LENGTH: 29
<212> TYPE: DNA
<213> ORGANISM: Artificial
<220> FEATURE:
<223> OTHER INFORMATION: primer

<400> SEQUENCE: 37
cctgctgcgt gctgtaactg actttaaac                                29

<210> SEQ ID NO 38
<211> LENGTH: 29
<212> TYPE: DNA
<213> ORGANISM: Artificial
<220> FEATURE:
<223> OTHER INFORMATION: primer

<400> SEQUENCE: 38
gtttaaagtc agttacagca cgcagcagg                                29

<210> SEQ ID NO 39
<211> LENGTH: 29
<212> TYPE: DNA

```
<213> ORGANISM: Artificial
<220> FEATURE:
<223> OTHER INFORMATION: primer

<400> SEQUENCE: 39
cgttaaggta ttgacggaag aaagcaaaa                                    29

<210> SEQ ID NO 40
<211> LENGTH: 29
<212> TYPE: DNA
<213> ORGANISM: Artificial
<220> FEATURE:
<223> OTHER INFORMATION: primer

<400> SEQUENCE: 40
ttttgctttc ttccgtcaat accttaacg                                    29

<210> SEQ ID NO 41
<211> LENGTH: 29
<212> TYPE: DNA
<213> ORGANISM: Artificial
<220> FEATURE:
<223> OTHER INFORMATION: primer

<400> SEQUENCE: 41
taaggtattg aaagacgaaa gcaaaaaat                                    29

<210> SEQ ID NO 42
<211> LENGTH: 29
<212> TYPE: DNA
<213> ORGANISM: Artificial
<220> FEATURE:
<223> OTHER INFORMATION: primer

<400> SEQUENCE: 42 atttttgct ttcgtctttc aatacctta                                     29

<210> SEQ ID NO 43
<211> LENGTH: 2148
<212> TYPE: DNA
<213> ORGANISM: Artificial
<220> FEATURE:
<221> NAME/KEY: CDS
<222> LOCATION: (1)..(2148)
<220> FEATURE:
<223> OTHER INFORMATION: Derived from E. Coli cadA

<400> SEQUENCE: 43 atg aac gtt att gca ata ttg aat cac atg ggg gtt tat ttt aaa gaa       48
Met Asn Val Ile Ala Ile Leu Asn His Met Gly Val Tyr Phe Lys Glu
1               5                  10                  15 gaa ccc atc cgt gaa ctt cat cgc gcg ctt gaa cgt ctg aac ttc cag       96
Glu Pro Ile Arg Glu Leu His Arg Ala Leu Glu Arg Leu Asn Phe Gln
            20                  25                  30 att gtt tac ccg aac gac cgt gac gac tta tta aaa ctg atc gaa aac      144
Ile Val Tyr Pro Asn Asp Arg Asp Asp Leu Leu Lys Leu Ile Glu Asn
        35                  40                  45 aat gcg cgt ctg tgc ggc gtt att ttt gac tgg gat aaa tat aat ctc      192
Asn Ala Arg Leu Cys Gly Val Ile Phe Asp Trp Asp Lys Tyr Asn Leu
    50                  55                  60 gag ctg tgc gaa gaa att agc aaa atg aac gag aac ctg ccg ttg tac      240
Glu Leu Cys Glu Glu Ile Ser Lys Met Asn Glu Asn Leu Pro Leu Tyr
65                  70                  75                  80 gcg ttc gct aat acg tat tcc act ctc gat gta agc ctg aat gac ctg      288
Ala Phe Ala Asn Thr Tyr Ser Thr Leu Asp Val Ser Leu Asn Asp Leu
```

-continued

|  |  |  |  |  |  |  |  |  |  |  |  |  |  |  |  |  |
|---|---|---|---|---|---|---|---|---|---|---|---|---|---|---|---|---|
|  |  | 85 |  |  |  | 90 |  |  |  |  | 95 |  |  |  |  |  |
| cgt | tta | cag | att | agc | ttc | ttt | gaa | tat | gcg | ctg | ggt | gct | gct | gaa | gat | 336 |
| Arg | Leu | Gln | Ile | Ser | Phe | Phe | Glu | Tyr | Ala | Leu | Gly | Ala | Ala | Glu | Asp |  |
|  |  | 100 |  |  |  | 105 |  |  |  |  | 110 |  |  |  |  |  |
| att | gct | aat | aag | atc | aag | cag | acc | act | gac | gaa | tat | atc | aac | act | att | 384 |
| Ile | Ala | Asn | Lys | Ile | Lys | Gln | Thr | Thr | Asp | Glu | Tyr | Ile | Asn | Thr | Ile |  |
|  | 115 |  |  |  |  | 120 |  |  |  |  | 125 |  |  |  |  |  |
| ctg | cct | ccg | ctg | act | aaa | gca | ctg | ttt | aaa | tat | gtt | cgt | gaa | ggt | aaa | 432 |
| Leu | Pro | Pro | Leu | Thr | Lys | Ala | Leu | Phe | Lys | Tyr | Val | Arg | Glu | Gly | Lys |  |
| 130 |  |  |  |  | 135 |  |  |  |  | 140 |  |  |  |  |  |  |
| tat | act | ttc | tgt | act | cct | ggt | cac | atg | ggc | ggt | act | gca | ttc | cag | aaa | 480 |
| Tyr | Thr | Phe | Cys | Thr | Pro | Gly | His | Met | Gly | Gly | Thr | Ala | Phe | Gln | Lys |  |
| 145 |  |  |  |  | 150 |  |  |  |  | 155 |  |  |  |  | 160 |  |
| agc | ccg | gta | ggt | agc | ctg | ttc | tat | gat | ttc | ttt | ggt | ccg | aat | acc | atg | 528 |
| Ser | Pro | Val | Gly | Ser | Leu | Phe | Tyr | Asp | Phe | Phe | Gly | Pro | Asn | Thr | Met |  |
|  |  |  |  | 165 |  |  |  |  | 170 |  |  |  |  | 175 |  |  |
| aaa | tct | gat | att | tcc | att | tca | gta | tct | gaa | ctg | ggt | tct | ctg | ctg | gat | 576 |
| Lys | Ser | Asp | Ile | Ser | Ile | Ser | Val | Ser | Glu | Leu | Gly | Ser | Leu | Leu | Asp |  |
|  |  |  | 180 |  |  |  |  | 185 |  |  |  |  | 190 |  |  |  |
| cac | agt | ggt | cca | cac | aaa | gaa | gca | gaa | cag | tat | atc | gct | cgc | gtc | ttt | 624 |
| His | Ser | Gly | Pro | His | Lys | Glu | Ala | Glu | Gln | Tyr | Ile | Ala | Arg | Val | Phe |  |
|  |  | 195 |  |  |  |  | 200 |  |  |  |  | 205 |  |  |  |  |
| aac | gca | gac | cgc | agc | tac | atg | gtg | acc | aac | ggt | act | tcc | act | gcg | aac | 672 |
| Asn | Ala | Asp | Arg | Ser | Tyr | Met | Val | Thr | Asn | Gly | Thr | Ser | Thr | Ala | Asn |  |
| 210 |  |  |  |  | 215 |  |  |  |  | 220 |  |  |  |  |  |  |
| aaa | att | gtt | ggt | atg | tac | tct | gct | cca | gca | ggc | agc | acc | att | ctg | att | 720 |
| Lys | Ile | Val | Gly | Met | Tyr | Ser | Ala | Pro | Ala | Gly | Ser | Thr | Ile | Leu | Ile |  |
| 225 |  |  |  |  | 230 |  |  |  |  | 235 |  |  |  |  | 240 |  |
| gac | cgt | aac | tgc | cac | aaa | tcg | ctg | acc | cac | ctg | atg | atg | atg | agc | gat | 768 |
| Asp | Arg | Asn | Cys | His | Lys | Ser | Leu | Thr | His | Leu | Met | Met | Met | Ser | Asp |  |
|  |  |  |  | 245 |  |  |  |  | 250 |  |  |  |  | 255 |  |  |
| gtt | acg | cca | atc | tat | ttc | cgc | ccg | acc | cgt | aac | gct | tac | ggt | att | ctt | 816 |
| Val | Thr | Pro | Ile | Tyr | Phe | Arg | Pro | Thr | Arg | Asn | Ala | Tyr | Gly | Ile | Leu |  |
|  |  |  | 260 |  |  |  |  | 265 |  |  |  |  | 270 |  |  |  |
| ggt | ggt | atc | cca | cag | agt | gaa | ttc | cag | cac | gct | acc | att | gct | aag | cgc | 864 |
| Gly | Gly | Ile | Pro | Gln | Ser | Glu | Phe | Gln | His | Ala | Thr | Ile | Ala | Lys | Arg |  |
|  |  | 275 |  |  |  |  | 280 |  |  |  |  | 285 |  |  |  |  |
| gtg | cac | gaa | aca | cca | aac | gca | acc | tgg | ccg | gta | cat | gct | gta | att | acc | 912 |
| Val | His | Glu | Thr | Pro | Asn | Ala | Thr | Trp | Pro | Val | His | Ala | Val | Ile | Thr |  |
| 290 |  |  |  |  | 295 |  |  |  |  | 300 |  |  |  |  |  |  |
| aac | tct | acc | tat | gat | ggt | ctg | ctg | tac | aac | acc | gac | ttc | atc | aag | aaa | 960 |
| Asn | Ser | Thr | Tyr | Asp | Gly | Leu | Leu | Tyr | Asn | Thr | Asp | Phe | Ile | Lys | Lys |  |
| 305 |  |  |  | 310 |  |  |  |  | 315 |  |  |  |  | 320 |  |  |
| aca | ctg | gat | gtg | aaa | tcc | atc | cac | ttt | gac | tcc | gcg | tgg | gtg | gct | tac | 1008 |
| Thr | Leu | Asp | Val | Lys | Ser | Ile | His | Phe | Asp | Ser | Ala | Trp | Val | Ala | Tyr |  |
|  |  |  |  | 325 |  |  |  |  | 330 |  |  |  |  | 335 |  |  |
| acc | aac | ttc | tca | ccg | att | tac | gaa | ggt | aaa | tgc | ggt | atg | agc | ggt | ggc | 1056 |
| Thr | Asn | Phe | Ser | Pro | Ile | Tyr | Glu | Gly | Lys | Cys | Gly | Met | Ser | Gly | Gly |  |
|  |  |  | 340 |  |  |  |  | 345 |  |  |  |  | 350 |  |  |  |
| cgt | gta | gaa | ggg | aaa | gtg | att | tac | gaa | acc | cag | tcc | act | cac | aaa | ctg | 1104 |
| Arg | Val | Glu | Gly | Lys | Val | Ile | Tyr | Glu | Thr | Gln | Ser | Thr | His | Lys | Leu |  |
|  |  | 355 |  |  |  |  | 360 |  |  |  |  | 365 |  |  |  |  |
| ctg | gcg | gcg | ttc | tct | cag | gct | tcc | atg | atc | cac | gtt | aaa | ggt | gac | gta | 1152 |
| Leu | Ala | Ala | Phe | Ser | Gln | Ala | Ser | Met | Ile | His | Val | Lys | Gly | Asp | Val |  |
| 370 |  |  |  |  | 375 |  |  |  |  | 380 |  |  |  |  |  |  |
| aac | gaa | gaa | acc | ttt | aac | gaa | gcc | tac | atg | atg | cac | acc | acc | act | tct | 1200 |
| Asn | Glu | Glu | Thr | Phe | Asn | Glu | Ala | Tyr | Met | Met | His | Thr | Thr | Thr | Ser |  |
| 385 |  |  |  |  | 390 |  |  |  |  | 395 |  |  |  |  | 400 |  |
| ccg | cac | tac | ggt | atc | gtg | gcg | tcc | act | gaa | acc | gct | gcg | gcg | atg | atg | 1248 |

```
                        Pro His Tyr Gly Ile Val Ala Ser Thr Glu Thr Ala Ala Met Met
                                        405                 410                 415 aaa ggc aat gca ggt aag cgt ctg atc aac ggt tct att gaa cgt gcg         1296
Lys Gly Asn Ala Gly Lys Arg Leu Ile Asn Gly Ser Ile Glu Arg Ala
            420                 425                 430 atc aaa ttc cgt aaa gag atc aaa cgt ctg aga acg gaa tct gat ggc         1344
Ile Lys Phe Arg Lys Glu Ile Lys Arg Leu Arg Thr Glu Ser Asp Gly
            435                 440                 445 tgg ttc ttt gat gta tgg cag ccg gat cat atc gat acg act gaa tgc         1392
Trp Phe Phe Asp Val Trp Gln Pro Asp His Ile Asp Thr Thr Glu Cys
            450                 455                 460 tgg ccg ctg cgt tct gac agc acc tgg cac aat ttc aaa aac atc gat         1440
Trp Pro Leu Arg Ser Asp Ser Thr Trp His Asn Phe Lys Asn Ile Asp
465                 470                 475                 480 aac gag cac atg tat ctt gac ccg atc aaa gtc acc ctg ctg act ccg         1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc         1536
Gly Met Glu Lys Asp Gly Thr Met Ser Asp Phe Gly Ile Pro Ala Ser
            500                 505                 510 atc gtg gcg aaa tac ctc gac gaa cat ggc atc gtt gtt gag aaa acc         1584
Ile Val Ala Lys Tyr Leu Asp Glu His Gly Ile Val Val Glu Lys Thr
            515                 520                 525 ggt ccg tat aac ctg ctg ttc ctg ttc agc atc ggt atc gat aag acc         1632
Gly Pro Tyr Asn Leu Leu Phe Leu Phe Ser Ile Gly Ile Asp Lys Thr
530                 535                 540 aaa gca ctg agc ctg ctg cgt gct ctg act gac ttt aaa cgt gcg ttc         1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa         1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat         1776
Asp Pro Glu Phe Tyr Glu Asn Met Arg Ile Gln Glu Leu Ala Gln Asn
            580                 585                 590 atc cac aaa ctg att gtt cac cac aat ctg ccg gat ctg atg tat cgc         1824
Ile His Lys Leu Ile Val His His Asn Leu Pro Asp Leu Met Tyr Arg
            595                 600                 605 gca ttt gaa gtg ctg ccg acg atg gta atg act ccg tat gct gca ttc         1872
Ala Phe Glu Val Leu Pro Thr Met Val Met Thr Pro Tyr Ala Ala Phe
610                 615                 620 cag aaa gag ctg cac ggt atg acc gaa gaa gtt tac ctc gac gaa atg         1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt         1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt         2016
Pro Leu Val Met Pro Gly Glu Met Ile Thr Glu Glu Ser Arg Pro Val
            660                 665                 670 ctg gag ttc ctg cag atg ctg tgt gaa atc ggc gct cac tat ccg ggc         2064
Leu Glu Phe Leu Gln Met Leu Cys Glu Ile Gly Ala His Tyr Pro Gly
            675                 680                 685 ttt gaa acc gat att cac ggt gca tac cgt cag gct gat ggc cgc tat         2112
Phe Glu Thr Asp Ile His Gly Ala Tyr Arg Gln Ala Asp Gly Arg Tyr
            690                 695                 700 acc gtt aag gta ttg aaa gac gaa agc aaa aaa taa                         2148
Thr Val Lys Val Leu Lys Asp Glu Ser Lys Lys
705                 710                 715
```

<210> SEQ ID NO 44
<211> LENGTH: 715
<212> TYPE: PRT
<213> ORGANISM: Artificial
<220> FEATURE:
<223> OTHER INFORMATION: Derived from E. Coli cadA

<400> SEQUENCE: 44

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val His Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Ala Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Asn Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
            595                 600                 605

Ala Phe Glu Val Leu Pro Thr Met Val Met Thr Pro Tyr Ala Ala Phe
610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
690                 695                 700

Thr Val Lys Val Leu Lys Asp Glu Ser Lys Lys
705                 710                 715

<210> SEQ ID NO 45
<211> LENGTH: 2148
<212> TYPE: DNA
<213> ORGANISM: Artificial
<220> FEATURE:
<221> NAME/KEY: CDS
<222> LOCATION: (1)..(2148)
<220> FEATURE:
<223> OTHER INFORMATION: Derived from E. Coli cadA

<400> SEQUENCE: 45

-continued

| | | |
|---|---|---|
| atg aac gtt att gca ata ttg aat cac atg ggg gtt tat ttt aaa gaa<br>Met Asn Val Ile Ala Ile Leu Asn His Met Gly Val Tyr Phe Lys Glu<br>1               5                  10                 15 | 48 | |
| gaa ccc atc cgt gaa ctt cat cgc gcg ctt gaa cgt ctg aac ttc cag<br>Glu Pro Ile Arg Glu Leu His Arg Ala Leu Glu Arg Leu Asn Phe Gln<br>        20                 25                 30 | 96 | |
| att gtt tac ccg aac gac cgt gac gac tta tta aaa ctg atc gaa aac<br>Ile Val Tyr Pro Asn Asp Arg Asp Asp Leu Leu Lys Leu Ile Glu Asn<br>    35                 40                 45 | 144 | |
| aat gcg cgt ctg tgc ggc gtt att ttt gac tgg gat aaa tat aat ctc<br>Asn Ala Arg Leu Cys Gly Val Ile Phe Asp Trp Asp Lys Tyr Asn Leu<br>50                 55                 60 | 192 | |
| gag ctg tgc gaa gaa att agc aaa atg aac gag aac ctg ccg ttg tac<br>Glu Leu Cys Glu Glu Ile Ser Lys Met Asn Glu Asn Leu Pro Leu Tyr<br>65                 70                 75                 80 | 240 | |
| gcg ttc gct aat acg tat tcc act ctc gat gta agc ctg aat gac ctg<br>Ala Phe Ala Asn Thr Tyr Ser Thr Leu Asp Val Ser Leu Asn Asp Leu<br>        85                 90                 95 | 288 | |
| cgt tta cag att agc ttc ttt gaa tat gcg ctg ggt gct gct gaa gat<br>Arg Leu Gln Ile Ser Phe Phe Glu Tyr Ala Leu Gly Ala Ala Glu Asp<br>    100                105                110 | 336 | |
| att gct aat aag atc aag cag acc act gac gaa tat atc aac act att<br>Ile Ala Asn Lys Ile Lys Gln Thr Thr Asp Glu Tyr Ile Asn Thr Ile<br>115                120                125 | 384 | |
| ctg cct ccg ctg act aaa gca ctg ttt aaa tat gtt cgt gaa ggt aaa<br>Leu Pro Pro Leu Thr Lys Ala Leu Phe Lys Tyr Val Arg Glu Gly Lys<br>130                135                140 | 432 | |
| tat act ttc tgt act cct ggt cac atg ggc ggt act gca ttc cag aaa<br>Tyr Thr Phe Cys Thr Pro Gly His Met Gly Gly Thr Ala Phe Gln Lys<br>145                150                155                160 | 480 | |
| agc ccg gta ggt agc ctg ttc tat gat ttc ttt ggt ccg aat acc atg<br>Ser Pro Val Gly Ser Leu Phe Tyr Asp Phe Phe Gly Pro Asn Thr Met<br>        165                170                175 | 528 | |
| aaa tct gat att tcc att tca gta tct gaa ctg ggt tct ctg ctg gat<br>Lys Ser Asp Ile Ser Ile Ser Val Ser Glu Leu Gly Ser Leu Leu Asp<br>    180                185                190 | 576 | |
| cac agt ggt cca cac aaa gaa gca gaa cag tat atc gct cgc gtc ttt<br>His Ser Gly Pro His Lys Glu Ala Glu Gln Tyr Ile Ala Arg Val Phe<br>195                200                205 | 624 | |
| aac gca gac cgc agc tac atg gtg acc aac ggt act tcc act gcg aac<br>Asn Ala Asp Arg Ser Tyr Met Val Thr Asn Gly Thr Ser Thr Ala Asn<br>210                215                220 | 672 | |
| aaa att gtt ggt atg tac tct gct cca gca ggc agc acc att ctg att<br>Lys Ile Val Gly Met Tyr Ser Ala Pro Ala Gly Ser Thr Ile Leu Ile<br>225                230                235                240 | 720 | |
| gac cgt aac tgc cac aaa tcg ctg acc cac ctg atg atg atg agc gat<br>Asp Arg Asn Cys His Lys Ser Leu Thr His Leu Met Met Met Ser Asp<br>        245                250                255 | 768 | |
| gtt acg cca atc tat ttc cgc ccg acc cgt aac gct tac ggt att ctt<br>Val Thr Pro Ile Tyr Phe Arg Pro Thr Arg Asn Ala Tyr Gly Ile Leu<br>    260                265                270 | 816 | |
| ggt ggt atc cca cag agt gaa ttc cag cac gct acc att gac aag cgc<br>Gly Gly Ile Pro Gln Ser Glu Phe Gln His Ala Thr Ile Asp Lys Arg<br>275                280                285 | 864 | |
| gtg cac gaa aca cca aac gca acc tgg ccg gta cat gct gta att acc<br>Val His Glu Thr Pro Asn Ala Thr Trp Pro Val His Ala Val Ile Thr<br>290                295                300 | 912 | |
| aac tct acc tat gat ggt ctg ctg tac aac acc gac ttc atc aag aaa<br>Asn Ser Thr Tyr Asp Gly Leu Leu Tyr Asn Thr Asp Phe Ile Lys Lys<br>305                310                315                320 | 960 | |

```
aca ctg gat gtg aaa tcc atc cac ttt gac tcc gcg tgg gtg gct tac    1008
Thr Leu Asp Val Lys Ser Ile His Phe Asp Ser Ala Trp Val Ala Tyr
            325                 330                 335 acc aac ttc tca ccg att tac gaa ggt aaa tgc ggt atg agc ggt ggc    1056
Thr Asn Phe Ser Pro Ile Tyr Glu Gly Lys Cys Gly Met Ser Gly Gly
            340                 345                 350 cgt gta gaa ggg aaa gtg att tac gaa acc cag tcc act cac aaa ctg    1104
Arg Val Glu Gly Lys Val Ile Tyr Glu Thr Gln Ser Thr His Lys Leu
            355                 360                 365 ctg gcg gcg ttc tct cag gct tcc atg atc cac gtt aaa ggt gac gta    1152
Leu Ala Ala Phe Ser Gln Ala Ser Met Ile His Val Lys Gly Asp Val
            370                 375                 380 aac gaa gaa acc ttt aac gaa gcc tac atg atg cac acc acc act tct    1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg    1248
Pro His Tyr Gly Ile Val Ala Ser Thr Glu Thr Ala Ala Ala Met Met
                405                 410                 415 aaa ggc aat gca ggt aag cgt ctg atc aac ggt tct att gaa cgt gcg    1296
Lys Gly Asn Ala Gly Lys Arg Leu Ile Asn Gly Ser Ile Glu Arg Ala
                420                 425                 430 atc aaa ttc cgt aaa gag atc aaa cgt ctg aga acg gaa tct gat ggc    1344
Ile Lys Phe Arg Lys Glu Ile Lys Arg Leu Arg Thr Glu Ser Asp Gly
            435                 440                 445 tgg ttc ttt gat gta tgg cag ccg gat cat atc gat acg act gaa tgc    1392
Trp Phe Phe Asp Val Trp Gln Pro Asp His Ile Asp Thr Thr Glu Cys
            450                 455                 460 tgg ccg ctg cgt tct gac agc acc tgg cac aat ttc aaa aac atc gat    1440
Trp Pro Leu Arg Ser Asp Ser Thr Trp His Asn Phe Lys Asn Ile Asp
465                 470                 475                 480 aac gag cac atg tat ctt gac ccg atc aaa gtc acc ctg ctg act ccg    1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc    1536
Gly Met Glu Lys Asp Gly Thr Met Ser Asp Phe Gly Ile Pro Ala Ser
                500                 505                 510 atc gtg gcg aaa tac ctc gac gaa cat ggc atc gtt gtt gag aaa acc    1584
Ile Val Ala Lys Tyr Leu Asp Glu His Gly Ile Val Val Glu Lys Thr
            515                 520                 525 ggt ccg tat aac ctg ctg ttc ctg ttc agc atc ggt atc gat aag acc    1632
Gly Pro Tyr Asn Leu Leu Phe Leu Phe Ser Ile Gly Ile Asp Lys Thr
            530                 535                 540 aaa gca ctg agc ctg ctg cgt gct ctg act gac ttt aaa cgt gcg ttc    1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa    1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat    1776
Asp Pro Glu Phe Tyr Glu Asn Met Arg Ile Gln Glu Leu Ala Gln Asn
                580                 585                 590 atc cac aaa ctg att gtt cac cac aat ctg ccg gat ctg atg tat cgc    1824
Ile His Lys Leu Ile Val His His Asn Leu Pro Asp Leu Met Tyr Arg
            595                 600                 605 gca ttt gaa gtg ctg ccg acg atg gta atg act ccg tat gct gca ttc    1872
Ala Phe Glu Val Leu Pro Thr Met Val Met Thr Pro Tyr Ala Ala Phe
            610                 615                 620 cag aaa gag ctg cac ggt atg acc gaa gaa gtt tac ctc gac gaa atg    1920
Gln Lys Glu Leu His Gly Met Thr Glu Glu Val Tyr Leu Asp Glu Met
```

```
                         625                 630                 635                 640
gta ggt cgt att aac gcc aat atg atc ctt ccg tac ccg ccg gga gtt        1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt        2016
Pro Leu Val Met Pro Gly Glu Met Ile Thr Glu Glu Ser Arg Pro Val
                660                 665                 670 ctg gag ttc ctg cag atg ctg tgt gaa atc ggc gct cac tat ccg ggc        2064
Leu Glu Phe Leu Gln Met Leu Cys Glu Ile Gly Ala His Tyr Pro Gly
                675                 680                 685 ttt gaa acc gat att cac ggt gca tac cgt cag gct gat ggc cgc tat        2112
Phe Glu Thr Asp Ile His Gly Ala Tyr Arg Gln Ala Asp Gly Arg Tyr
                690                 695                 700 acc gtt aag gta ttg aaa gac gaa agc aaa aaa taa                        2148
Thr Val Lys Val Leu Lys Asp Glu Ser Lys Lys
705                 710                 715

<210> SEQ ID NO 46
<211> LENGTH: 715
<212> TYPE: PRT
<213> ORGANISM: Artificial
<220> FEATURE:
<223> OTHER INFORMATION: Derived from E. Coli cadA

<400> SEQUENCE: 46

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
                20                  25                  30

Ile Val Tyr Pro Asn Asp Arg Asp Leu Leu Lys Leu Ile Glu Asn
            35                  40                  45

Asn Ala Arg Leu Cys Gly Val Ile Phe Asp Trp Asp Lys Tyr Asn Leu
        50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255
```

```
Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Asp Lys Arg
            275                 280                 285

Val His Glu Thr Pro Asn Ala Thr Trp Pro Val His Ala Val Ile Thr
            290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Ala Tyr
            325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
            405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
            450                 455                 460

Trp Pro Leu Arg Ser Asp Ser Thr Trp His Asn Phe Lys Asn Ile Asp
465                 470                 475                 480

Asn Glu His Met Tyr Leu Asp Pro Ile Lys Val Thr Leu Leu Thr Pro
            485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
            565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
            595                 600                 605

Ala Phe Glu Val Leu Pro Thr Met Val Met Thr Pro Tyr Ala Ala Phe
            610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
            645                 650                 655

Pro Leu Val Met Pro Gly Glu Met Ile Thr Glu Glu Ser Arg Pro Val
            660                 665                 670
```

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
        690                 695                 700

Thr Val Lys Val Leu Lys Asp Glu Ser Lys Lys
705                 710                 715

<210> SEQ ID NO 47
<211> LENGTH: 29
<212> TYPE: DNA
<213> ORGANISM: Artificial
<220> FEATURE:
<223> OTHER INFORMATION: primer

<400> SEQUENCE: 47
catgggggtt tatcaaaaag aagaaccca                                     29

<210> SEQ ID NO 48
<211> LENGTH: 29
<212> TYPE: DNA
<213> ORGANISM: Artificial
<220> FEATURE:
<223> OTHER INFORMATION: primer

<400> SEQUENCE: 48
tgggttcttc tttttgataa accccatg                                      29

<210> SEQ ID NO 49
<211> LENGTH: 29
<212> TYPE: DNA
<213> ORGANISM: Artificial
<220> FEATURE:
<223> OTHER INFORMATION: primer

<400> SEQUENCE: 49
acccatccgt gaattgcatc gcgcgcttg                                     29

<210> SEQ ID NO 50
<211> LENGTH: 29
<212> TYPE: DNA
<213> ORGANISM: Artificial
<220> FEATURE:
<223> OTHER INFORMATION: primer

<400> SEQUENCE: 50
caagcgcgcg atgcaattca cggatgggt                                     29

<210> SEQ ID NO 51
<211> LENGTH: 29
<212> TYPE: DNA
<213> ORGANISM: Artificial
<220> FEATURE:
<223> OTHER INFORMATION: primer

<400> SEQUENCE: 51
tcgcgcgctt gaaattctga acttccaga                                     29

<210> SEQ ID NO 52
<211> LENGTH: 29
<212> TYPE: DNA
<213> ORGANISM: Artificial
<220> FEATURE:
<223> OTHER INFORMATION: primer

<400> SEQUENCE: 52

```
tctggaagtt cagaatttca agcgcgcga                                      29
```

<210> SEQ ID NO 53
<211> LENGTH: 29
<212> TYPE: DNA
<213> ORGANISM: Artificial
<220> FEATURE:
<223> OTHER INFORMATION: primer

<400> SEQUENCE: 53

```
ttacccgaac gacatagacg acttattaa                                      29
```

<210> SEQ ID NO 54
<211> LENGTH: 29
<212> TYPE: DNA
<213> ORGANISM: Artificial
<220> FEATURE:
<223> OTHER INFORMATION: primer

<400> SEQUENCE: 54

```
ttaataagtc gtctatgtcg ttcgggtaa                                      29
```

<210> SEQ ID NO 55
<211> LENGTH: 29
<212> TYPE: DNA
<213> ORGANISM: Artificial
<220> FEATURE:
<223> OTHER INFORMATION: primer

<400> SEQUENCE: 55

```
ttacccgaac gacatcgacg acttattaa                                      29
```

<210> SEQ ID NO 56
<211> LENGTH: 29
<212> TYPE: DNA
<213> ORGANISM: Artificial
<220> FEATURE:
<223> OTHER INFORMATION: primer

<400> SEQUENCE: 56

```
ttaataagtc gtcgatgtcg ttcgggtaa                                      29
```

<210> SEQ ID NO 57
<211> LENGTH: 29
<212> TYPE: DNA
<213> ORGANISM: Artificial
<220> FEATURE:
<223> OTHER INFORMATION: primer

<400> SEQUENCE: 57

```
ttacccgaac gacgtggacg acttattaa                                      29
```

<210> SEQ ID NO 58
<211> LENGTH: 29
<212> TYPE: DNA
<213> ORGANISM: Artificial
<220> FEATURE:
<223> OTHER INFORMATION: primer

<400> SEQUENCE: 58

```
ttaataagtc gtccacgtcg ttcgggtaa                                      29
```

<210> SEQ ID NO 59
<211> LENGTH: 29
<212> TYPE: DNA
<213> ORGANISM: Artificial

<220> FEATURE:
<223> OTHER INFORMATION: primer

<400> SEQUENCE: 59
ggataaatat aataaagagc tgtgcgaag                                29

<210> SEQ ID NO 60
<211> LENGTH: 29
<212> TYPE: DNA
<213> ORGANISM: Artificial
<220> FEATURE:
<223> OTHER INFORMATION: primer

<400> SEQUENCE: 60
cttcgcacag ctctttatta tatttatcc                                29

<210> SEQ ID NO 61
<211> LENGTH: 29
<212> TYPE: DNA
<213> ORGANISM: Artificial
<220> FEATURE:
<223> OTHER INFORMATION: primer

<400> SEQUENCE: 61
taatctcgag ctgaccgaag aaattagca                                29

<210> SEQ ID NO 62
<211> LENGTH: 29
<212> TYPE: DNA
<213> ORGANISM: Artificial
<220> FEATURE:
<223> OTHER INFORMATION: primer

<400> SEQUENCE: 62
tgctaatttc ttcggtcagc tcgagatta                                29

<210> SEQ ID NO 63
<211> LENGTH: 29
<212> TYPE: DNA
<213> ORGANISM: Artificial
<220> FEATURE:
<223> OTHER INFORMATION: primer

<400> SEQUENCE: 63
taatctcgag ctgttagaag aaattagca                                29

<210> SEQ ID NO 64
<211> LENGTH: 29
<212> TYPE: DNA
<213> ORGANISM: Artificial
<220> FEATURE:
<223> OTHER INFORMATION: primer

<400> SEQUENCE: 64
tgctaatttc ttctaacagc tcgagatta                                29

<210> SEQ ID NO 65
<211> LENGTH: 29
<212> TYPE: DNA
<213> ORGANISM: Artificial
<220> FEATURE:
<223> OTHER INFORMATION: primer

<400> SEQUENCE: 65
gctgtgcgaa gaattgagca aaatgaacg                                29

```
<210> SEQ ID NO 66
<211> LENGTH: 29
<212> TYPE: DNA
<213> ORGANISM: Artificial
<220> FEATURE:
<223> OTHER INFORMATION: primer

<400> SEQUENCE: 66
cgttcatttt gctcaattct tcgcacagc                                29

<210> SEQ ID NO 67
<211> LENGTH: 29
<212> TYPE: DNA
<213> ORGANISM: Artificial
<220> FEATURE:
<223> OTHER INFORMATION: primer

<400> SEQUENCE: 67
gctgtgcgaa gaactgagca aaatgaacg                                29

<210> SEQ ID NO 68
<211> LENGTH: 29
<212> TYPE: DNA
<213> ORGANISM: Artificial
<220> FEATURE:
<223> OTHER INFORMATION: primer

<400> SEQUENCE: 68
cgttcatttt gctcagttct tcgcacagc                                29

<210> SEQ ID NO 69
<211> LENGTH: 29
<212> TYPE: DNA
<213> ORGANISM: Artificial
<220> FEATURE:
<223> OTHER INFORMATION: primer

<400> SEQUENCE: 69
gctgtgcgaa gaaccgagca aaatgaacg                                29

<210> SEQ ID NO 70
<211> LENGTH: 29
<212> TYPE: DNA
<213> ORGANISM: Artificial
<220> FEATURE:
<223> OTHER INFORMATION: primer

<400> SEQUENCE: 70
cgttcatttt gctcggttct tcgcacagc                                29

<210> SEQ ID NO 71
<211> LENGTH: 29
<212> TYPE: DNA
<213> ORGANISM: Artificial
<220> FEATURE:
<223> OTHER INFORMATION: primer

<400> SEQUENCE: 71
tagcaaaatg aaccccaacc tgccgttgt                                29

<210> SEQ ID NO 72
<211> LENGTH: 29
<212> TYPE: DNA
<213> ORGANISM: Artificial
<220> FEATURE:
<223> OTHER INFORMATION: primer
```

```
<400> SEQUENCE: 72
acaacggcag gttggggttc attttgcta                                         29

<210> SEQ ID NO 73
<211> LENGTH: 29
<212> TYPE: DNA
<213> ORGANISM: Artificial
<220> FEATURE:
<223> OTHER INFORMATION: primer

<400> SEQUENCE: 73
tagcaaaatg aaccacaacc tgccgttgt                                         29

<210> SEQ ID NO 74
<211> LENGTH: 29
<212> TYPE: DNA
<213> ORGANISM: Artificial
<220> FEATURE:
<223> OTHER INFORMATION: primer

<400> SEQUENCE: 74
acaacggcag gttgtggttc attttgcta                                         29

<210> SEQ ID NO 75
<211> LENGTH: 29
<212> TYPE: DNA
<213> ORGANISM: Artificial
<220> FEATURE:
<223> OTHER INFORMATION: primer

<400> SEQUENCE: 75
cgagaacctg ccgatatacg cgttcgcta                                         29

<210> SEQ ID NO 76
<211> LENGTH: 29
<212> TYPE: DNA
<213> ORGANISM: Artificial
<220> FEATURE:
<223> OTHER INFORMATION: primer

<400> SEQUENCE: 76
tagcgaacgc gtatatcggc aggttctcg                                         29

<210> SEQ ID NO 77
<211> LENGTH: 29
<212> TYPE: DNA
<213> ORGANISM: Artificial
<220> FEATURE:
<223> OTHER INFORMATION: primer

<400> SEQUENCE: 77
gttgtacgcg ttcctgaata cgtattcca                                         29

<210> SEQ ID NO 78
<211> LENGTH: 29
<212> TYPE: DNA
<213> ORGANISM: Artificial
<220> FEATURE:
<223> OTHER INFORMATION: primer

<400> SEQUENCE: 78
tggaatacgt attcaggaac gcgtacaac                                         29

<210> SEQ ID NO 79
```

```
<211> LENGTH: 29
<212> TYPE: DNA
<213> ORGANISM: Artificial
<220> FEATURE:
<223> OTHER INFORMATION: primer

<400> SEQUENCE: 79
gttgtacgcg ttcctaaata cgtattcca                                      29

<210> SEQ ID NO 80
<211> LENGTH: 29
<212> TYPE: DNA
<213> ORGANISM: Artificial
<220> FEATURE:
<223> OTHER INFORMATION: primer

<400> SEQUENCE: 80
tggaatacgt atttaggaac gcgtacaac                                      29

<210> SEQ ID NO 81
<211> LENGTH: 29
<212> TYPE: DNA
<213> ORGANISM: Artificial
<220> FEATURE:
<223> OTHER INFORMATION: primer

<400> SEQUENCE: 81
gttgtacgcg ttccttaata cgtattcca                                      29

<210> SEQ ID NO 82
<211> LENGTH: 29
<212> TYPE: DNA
<213> ORGANISM: Artificial
<220> FEATURE:
<223> OTHER INFORMATION: primer

<400> SEQUENCE: 82
tggaatacgt attaaggaac gcgtacaac                                      29

<210> SEQ ID NO 83
<211> LENGTH: 29
<212> TYPE: DNA
<213> ORGANISM: Artificial
<220> FEATURE:
<223> OTHER INFORMATION: primer

<400> SEQUENCE: 83
gttgtacgcg ttcataaata cgtattcca                                      29

<210> SEQ ID NO 84
<211> LENGTH: 29
<212> TYPE: DNA
<213> ORGANISM: Artificial
<220> FEATURE:
<223> OTHER INFORMATION: primer

<400> SEQUENCE: 84
tggaatacgt atttatgaac gcgtacaac                                      29

<210> SEQ ID NO 85
<211> LENGTH: 29
<212> TYPE: DNA
<213> ORGANISM: Artificial
<220> FEATURE:
<223> OTHER INFORMATION: primer

<400> SEQUENCE: 85
```
gttgtacgcg ttcgccaata cgtattcca                                   29

<210> SEQ ID NO 86
<211> LENGTH: 29
<212> TYPE: DNA
<213> ORGANISM: Artificial
<220> FEATURE:
<223> OTHER INFORMATION: primer

<400> SEQUENCE: 86
tggaatacgt attggcgaac gcgtacaac                                   29

<210> SEQ ID NO 87
<211> LENGTH: 29
<212> TYPE: DNA
<213> ORGANISM: Artificial
<220> FEATURE:
<223> OTHER INFORMATION: primer

<400> SEQUENCE: 87
gtacgcgttc gctgacacgt attccactc                                   29

<210> SEQ ID NO 88
<211> LENGTH: 29
<212> TYPE: DNA
<213> ORGANISM: Artificial
<220> FEATURE:
<223> OTHER INFORMATION: primer

<400> SEQUENCE: 88
gagtggaata cgtgtcagcg aacgcgtac                                   29

<210> SEQ ID NO 89
<211> LENGTH: 29
<212> TYPE: DNA
<213> ORGANISM: Artificial
<220> FEATURE:
<223> OTHER INFORMATION: primer

<400> SEQUENCE: 89
gtacgcgttc gctacaacgt attccactc                                   29

<210> SEQ ID NO 90
<211> LENGTH: 29
<212> TYPE: DNA
<213> ORGANISM: Artificial
<220> FEATURE:
<223> OTHER INFORMATION: primer

<400> SEQUENCE: 90
gagtggaata cgttgtagcg aacgcgtac                                   29

<210> SEQ ID NO 91
<211> LENGTH: 29
<212> TYPE: DNA
<213> ORGANISM: Artificial
<220> FEATURE:
<223> OTHER INFORMATION: primer

<400> SEQUENCE: 91
cgcgttcgct aatccatatt ccactctcg                                   29

<210> SEQ ID NO 92
<211> LENGTH: 29
<212> TYPE: DNA

```
<213> ORGANISM: Artificial
<220> FEATURE:
<223> OTHER INFORMATION: primer

<400> SEQUENCE: 92
cgagagtgga atatggatta gcgaacgcg                                29

<210> SEQ ID NO 93
<211> LENGTH: 29
<212> TYPE: DNA
<213> ORGANISM: Artificial
<220> FEATURE:
<223> OTHER INFORMATION: primer

<400> SEQUENCE: 93
taatacgtat tccaaactcg atgtaagcc                                29

<210> SEQ ID NO 94
<211> LENGTH: 29
<212> TYPE: DNA
<213> ORGANISM: Artificial
<220> FEATURE:
<223> OTHER INFORMATION: primer

<400> SEQUENCE: 94
ggcttacatc gagtttggaa tacgtatta                                29

<210> SEQ ID NO 95
<211> LENGTH: 29
<212> TYPE: DNA
<213> ORGANISM: Artificial
<220> FEATURE:
<223> OTHER INFORMATION: primer

<400> SEQUENCE: 95
taatacgtat tccaagctcg atgtaagcc                                29

<210> SEQ ID NO 96
<211> LENGTH: 29
<212> TYPE: DNA
<213> ORGANISM: Artificial
<220> FEATURE:
<223> OTHER INFORMATION: primer

<400> SEQUENCE: 96
ggcttacatc gagcttggaa tacgtatta                                29

<210> SEQ ID NO 97
<211> LENGTH: 29
<212> TYPE: DNA
<213> ORGANISM: Artificial
<220> FEATURE:
<223> OTHER INFORMATION: primer

<400> SEQUENCE: 97
taatacgtat tccagactcg atgtaagcc                                29

<210> SEQ ID NO 98
<211> LENGTH: 29
<212> TYPE: DNA
<213> ORGANISM: Artificial
<220> FEATURE:
<223> OTHER INFORMATION: primer

<400> SEQUENCE: 98
ggcttacatc gagtctggaa tacgtatta                                29
```

<210> SEQ ID NO 99
<211> LENGTH: 29
<212> TYPE: DNA
<213> ORGANISM: Artificial
<220> FEATURE:
<223> OTHER INFORMATION: primer

<400> SEQUENCE: 99
taatacgtat tccaatctcg atgtaagcc                                    29

<210> SEQ ID NO 100
<211> LENGTH: 29
<212> TYPE: DNA
<213> ORGANISM: Artificial
<220> FEATURE:
<223> OTHER INFORMATION: primer

<400> SEQUENCE: 100
ggcttacatc gagattggaa tacgtatta                                    29

<210> SEQ ID NO 101
<211> LENGTH: 29
<212> TYPE: DNA
<213> ORGANISM: Artificial
<220> FEATURE:
<223> OTHER INFORMATION: primer

<400> SEQUENCE: 101
tacgtattcc acttttgatg taagcctga                                    29

<210> SEQ ID NO 102
<211> LENGTH: 29
<212> TYPE: DNA
<213> ORGANISM: Artificial
<220> FEATURE:
<223> OTHER INFORMATION: primer

<400> SEQUENCE: 102
tcaggcttac atcaaaagtg gaatacgta                                    29

<210> SEQ ID NO 103
<211> LENGTH: 29
<212> TYPE: DNA
<213> ORGANISM: Artificial
<220> FEATURE:
<223> OTHER INFORMATION: primer

<400> SEQUENCE: 103
cgatgtaagc ctgatcgacc tgcgtttac                                    29

<210> SEQ ID NO 104
<211> LENGTH: 29
<212> TYPE: DNA
<213> ORGANISM: Artificial
<220> FEATURE:
<223> OTHER INFORMATION: primer

<400> SEQUENCE: 104
gtaaacgcag gtcgatcagg cttacatcg                                    29

<210> SEQ ID NO 105
<211> LENGTH: 29
<212> TYPE: DNA
<213> ORGANISM: Artificial
<220> FEATURE:

<223> OTHER INFORMATION: primer

<400> SEQUENCE: 105
tgtaagcctg aatccgctgc gtttacaga                                29

<210> SEQ ID NO 106
<211> LENGTH: 29
<212> TYPE: DNA
<213> ORGANISM: Artificial
<220> FEATURE:
<223> OTHER INFORMATION: primer

<400> SEQUENCE: 106
tctgtaaacg cagcggattc aggcttaca                                29

<210> SEQ ID NO 107
<211> LENGTH: 29
<212> TYPE: DNA
<213> ORGANISM: Artificial
<220> FEATURE:
<223> OTHER INFORMATION: primer

<400> SEQUENCE: 107
gaatgacctg cgtatacaga ttagcttct                                29

<210> SEQ ID NO 108
<211> LENGTH: 29
<212> TYPE: DNA
<213> ORGANISM: Artificial
<220> FEATURE:
<223> OTHER INFORMATION: primer

<400> SEQUENCE: 108
agaagctaat ctgtatacgc aggtcattc                                29

<210> SEQ ID NO 109
<211> LENGTH: 29
<212> TYPE: DNA
<213> ORGANISM: Artificial
<220> FEATURE:
<223> OTHER INFORMATION: primer

<400> SEQUENCE: 109
tgacctgcgt ttaactatta gcttctttg                                29

<210> SEQ ID NO 110
<211> LENGTH: 29
<212> TYPE: DNA
<213> ORGANISM: Artificial
<220> FEATURE:
<223> OTHER INFORMATION: primer

<400> SEQUENCE: 110
caaagaagct aatagttaaa cgcaggtca                                29

<210> SEQ ID NO 111
<211> LENGTH: 29
<212> TYPE: DNA
<213> ORGANISM: Artificial
<220> FEATURE:
<223> OTHER INFORMATION: primer

<400> SEQUENCE: 111
gattagcttc tttaattatg cgctgggtg                                29

```
<210> SEQ ID NO 112
<211> LENGTH: 29
<212> TYPE: DNA
<213> ORGANISM: Artificial
<220> FEATURE:
<223> OTHER INFORMATION: primer

<400> SEQUENCE: 112
cacccagcgc ataattaaag aagctaatc                                29

<210> SEQ ID NO 113
<211> LENGTH: 29
<212> TYPE: DNA
<213> ORGANISM: Artificial
<220> FEATURE:
<223> OTHER INFORMATION: primer

<400> SEQUENCE: 113
gattagcttc tttaaatatg cgctgggtg                                29

<210> SEQ ID NO 114
<211> LENGTH: 29
<212> TYPE: DNA
<213> ORGANISM: Artificial
<220> FEATURE:
<223> OTHER INFORMATION: primer

<400> SEQUENCE: 114
cacccagcgc atatttaaag aagctaatc                                29

<210> SEQ ID NO 115
<211> LENGTH: 29
<212> TYPE: DNA
<213> ORGANISM: Artificial
<220> FEATURE:
<223> OTHER INFORMATION: primer

<400> SEQUENCE: 115
gggtgctgct gaagagattg ctaataaga                                29

<210> SEQ ID NO 116
<211> LENGTH: 29
<212> TYPE: DNA
<213> ORGANISM: Artificial
<220> FEATURE:
<223> OTHER INFORMATION: primer

<400> SEQUENCE: 116
tcttattagc aatctcttca gcagcaccc                                29

<210> SEQ ID NO 117
<211> LENGTH: 29
<212> TYPE: DNA
<213> ORGANISM: Artificial
<220> FEATURE:
<223> OTHER INFORMATION: primer

<400> SEQUENCE: 117
taataagatc aagaacacca ctgacgaat                                29

<210> SEQ ID NO 118
<211> LENGTH: 29
<212> TYPE: DNA
<213> ORGANISM: Artificial
<220> FEATURE:
<223> OTHER INFORMATION: primer
```

```
<400> SEQUENCE: 118
attcgtcagt ggtgttcttg atcttatta                                29

<210> SEQ ID NO 119
<211> LENGTH: 29
<212> TYPE: DNA
<213> ORGANISM: Artificial
<220> FEATURE:
<223> OTHER INFORMATION: primer

<400> SEQUENCE: 119
taataagatc aagaatacca ctgacgaat                                29

<210> SEQ ID NO 120
<211> LENGTH: 29
<212> TYPE: DNA
<213> ORGANISM: Artificial
<220> FEATURE:
<223> OTHER INFORMATION: primer

<400> SEQUENCE: 120
attcgtcagt ggtattcttg atcttatta                                29

<210> SEQ ID NO 121
<211> LENGTH: 29
<212> TYPE: DNA
<213> ORGANISM: Artificial
<220> FEATURE:
<223> OTHER INFORMATION: primer

<400> SEQUENCE: 121
taataagatc aagattacca ctgacgaat                                29

<210> SEQ ID NO 122
<211> LENGTH: 29
<212> TYPE: DNA
<213> ORGANISM: Artificial
<220> FEATURE:
<223> OTHER INFORMATION: primer

<400> SEQUENCE: 122
attcgtcagt ggtaatcttg atcttatta                                29

<210> SEQ ID NO 123
<211> LENGTH: 29
<212> TYPE: DNA
<213> ORGANISM: Artificial
<220> FEATURE:
<223> OTHER INFORMATION: primer

<400> SEQUENCE: 123
taataagatc aagaccacca ctgacgaat                                29

<210> SEQ ID NO 124
<211> LENGTH: 29
<212> TYPE: DNA
<213> ORGANISM: Artificial
<220> FEATURE:
<223> OTHER INFORMATION: primer

<400> SEQUENCE: 124
attcgtcagt ggtggtcttg atcttatta                                29

<210> SEQ ID NO 125
<211> LENGTH: 29
```

```
<212> TYPE: DNA
<213> ORGANISM: Artificial
<220> FEATURE:
<223> OTHER INFORMATION: primer

<400> SEQUENCE: 125
taataagatc aagagtacca ctgacgaat                                    29

<210> SEQ ID NO 126
<211> LENGTH: 29
<212> TYPE: DNA
<213> ORGANISM: Artificial
<220> FEATURE:
<223> OTHER INFORMATION: primer

<400> SEQUENCE: 126
attcgtcagt ggtactcttg atcttatta                                    29

<210> SEQ ID NO 127
<211> LENGTH: 29
<212> TYPE: DNA
<213> ORGANISM: Artificial
<220> FEATURE:
<223> OTHER INFORMATION: primer

<400> SEQUENCE: 127
agcactgttt aaagtagttc gtgaaggta                                    29

<210> SEQ ID NO 128
<211> LENGTH: 29
<212> TYPE: DNA
<213> ORGANISM: Artificial
<220> FEATURE:
<223> OTHER INFORMATION: primer

<400> SEQUENCE: 128
taccttcacg aactacttta aacagtgct                                    29

<210> SEQ ID NO 129
<211> LENGTH: 29
<212> TYPE: DNA
<213> ORGANISM: Artificial
<220> FEATURE:
<223> OTHER INFORMATION: primer

<400> SEQUENCE: 129
agcactgttt aaagtggttc gtgaaggta                                    29

<210> SEQ ID NO 130
<211> LENGTH: 29
<212> TYPE: DNA
<213> ORGANISM: Artificial
<220> FEATURE:
<223> OTHER INFORMATION: primer

<400> SEQUENCE: 130
taccttcacg aaccacttta aacagtgct                                    29

<210> SEQ ID NO 131
<211> LENGTH: 29
<212> TYPE: DNA
<213> ORGANISM: Artificial
<220> FEATURE:
<223> OTHER INFORMATION: primer

<400> SEQUENCE: 131
```
agcactgttt aaatgcgttc gtgaaggta                                                29

<210> SEQ ID NO 132
<211> LENGTH: 29
<212> TYPE: DNA
<213> ORGANISM: Artificial
<220> FEATURE:
<223> OTHER INFORMATION: primer

<400> SEQUENCE: 132
taccttcacg aacgcattta aacagtgct                                                29

<210> SEQ ID NO 133
<211> LENGTH: 29
<212> TYPE: DNA
<213> ORGANISM: Artificial
<220> FEATURE:
<223> OTHER INFORMATION: primer

<400> SEQUENCE: 133
agcactgttt aaaacagttc gtgaaggta                                                29

<210> SEQ ID NO 134
<211> LENGTH: 29
<212> TYPE: DNA
<213> ORGANISM: Artificial
<220> FEATURE:
<223> OTHER INFORMATION: primer

<400> SEQUENCE: 134
taccttcacg aactgtttta aacagtgct                                                29

<210> SEQ ID NO 135
<211> LENGTH: 29
<212> TYPE: DNA
<213> ORGANISM: Artificial
<220> FEATURE:
<223> OTHER INFORMATION: primer

<400> SEQUENCE: 135
agcactgttt aaatctgttc gtgaaggta                                                29

<210> SEQ ID NO 136
<211> LENGTH: 29
<212> TYPE: DNA
<213> ORGANISM: Artificial
<220> FEATURE:
<223> OTHER INFORMATION: primer

<400> SEQUENCE: 136
taccttcacg aacagattta aacagtgct                                                29

<210> SEQ ID NO 137
<211> LENGTH: 29
<212> TYPE: DNA
<213> ORGANISM: Artificial
<220> FEATURE:
<223> OTHER INFORMATION: primer

<400> SEQUENCE: 137
agcactgttt aaaagtgttc gtgaaggta                                                29

<210> SEQ ID NO 138
<211> LENGTH: 29
<212> TYPE: DNA
<213> ORGANISM: Artificial

```
<220> FEATURE:
<223> OTHER INFORMATION: primer

<400> SEQUENCE: 138
taccttcacg aacactttta aacagtgct                                              29

<210> SEQ ID NO 139
<211> LENGTH: 29
<212> TYPE: DNA
<213> ORGANISM: Artificial
<220> FEATURE:
<223> OTHER INFORMATION: primer

<400> SEQUENCE: 139
agcactgttt aaaaacgttc gtgaaggta                                              29

<210> SEQ ID NO 140
<211> LENGTH: 29
<212> TYPE: DNA
<213> ORGANISM: Artificial
<220> FEATURE:
<223> OTHER INFORMATION: primer

<400> SEQUENCE: 140
taccttcacg aacgttttta aacagtgct                                              29

<210> SEQ ID NO 141
<211> LENGTH: 29
<212> TYPE: DNA
<213> ORGANISM: Artificial
<220> FEATURE:
<223> OTHER INFORMATION: primer

<400> SEQUENCE: 141
atatgttcgt gaagaaaaat atactttct                                              29

<210> SEQ ID NO 142
<211> LENGTH: 29
<212> TYPE: DNA
<213> ORGANISM: Artificial
<220> FEATURE:
<223> OTHER INFORMATION: primer

<400> SEQUENCE: 142
agaaagtata tttttcttca cgaacatat                                              29

<210> SEQ ID NO 143
<211> LENGTH: 29
<212> TYPE: DNA
<213> ORGANISM: Artificial
<220> FEATURE:
<223> OTHER INFORMATION: primer

<400> SEQUENCE: 143
tcgtgaaggt aaacgtactt tctgtactc                                              29

<210> SEQ ID NO 144
<211> LENGTH: 29
<212> TYPE: DNA
<213> ORGANISM: Artificial
<220> FEATURE:
<223> OTHER INFORMATION: primer

<400> SEQUENCE: 144
gagtacagaa agtacgttta ccttcacga                                              29
```

```
<210> SEQ ID NO 145
<211> LENGTH: 29
<212> TYPE: DNA
<213> ORGANISM: Artificial
<220> FEATURE:
<223> OTHER INFORMATION: primer

<400> SEQUENCE: 145
tcgtgaaggt aaaagaactt tctgtactc                                    29

<210> SEQ ID NO 146
<211> LENGTH: 29
<212> TYPE: DNA
<213> ORGANISM: Artificial
<220> FEATURE:
<223> OTHER INFORMATION: primer

<400> SEQUENCE: 146
gagtacagaa agttctttta ccttcacga                                    29

<210> SEQ ID NO 147
<211> LENGTH: 29
<212> TYPE: DNA
<213> ORGANISM: Artificial
<220> FEATURE:
<223> OTHER INFORMATION: primer

<400> SEQUENCE: 147
taaatatact ttcagtactc ctggtcaca                                    29

<210> SEQ ID NO 148
<211> LENGTH: 29
<212> TYPE: DNA
<213> ORGANISM: Artificial
<220> FEATURE:
<223> OTHER INFORMATION: primer

<400> SEQUENCE: 148
tgtgaccagg agtactgaaa gtatattta                                    29

<210> SEQ ID NO 149
<211> LENGTH: 29
<212> TYPE: DNA
<213> ORGANISM: Artificial
<220> FEATURE:
<223> OTHER INFORMATION: primer

<400> SEQUENCE: 149
taaatatact ttctctactc ctggtcaca                                    29

<210> SEQ ID NO 150
<211> LENGTH: 29
<212> TYPE: DNA
<213> ORGANISM: Artificial
<220> FEATURE:
<223> OTHER INFORMATION: primer

<400> SEQUENCE: 150
tgtgaccagg agtagagaaa gtatattta                                    29

<210> SEQ ID NO 151
<211> LENGTH: 29
<212> TYPE: DNA
<213> ORGANISM: Artificial
<220> FEATURE:
<223> OTHER INFORMATION: primer
```

<400> SEQUENCE: 151
taaatatact ttctccactc ctggtcaca					29

<210> SEQ ID NO 152
<211> LENGTH: 29
<212> TYPE: DNA
<213> ORGANISM: Artificial
<220> FEATURE:
<223> OTHER INFORMATION: primer

<400> SEQUENCE: 152
tgtgaccagg agtggagaaa gtatattta					29

<210> SEQ ID NO 153
<211> LENGTH: 29
<212> TYPE: DNA
<213> ORGANISM: Artificial
<220> FEATURE:
<223> OTHER INFORMATION: primer

<400> SEQUENCE: 153
taaatatact ttctcaactc ctggtcaca					29

<210> SEQ ID NO 154
<211> LENGTH: 29
<212> TYPE: DNA
<213> ORGANISM: Artificial
<220> FEATURE:
<223> OTHER INFORMATION: primer

<400> SEQUENCE: 154
tgtgaccagg agttgagaaa gtatattta					29

<210> SEQ ID NO 155
<211> LENGTH: 29
<212> TYPE: DNA
<213> ORGANISM: Artificial
<220> FEATURE:
<223> OTHER INFORMATION: primer

<400> SEQUENCE: 155
taaatatact ttcgcgactc ctggtcaca					29

<210> SEQ ID NO 156
<211> LENGTH: 29
<212> TYPE: DNA
<213> ORGANISM: Artificial
<220> FEATURE:
<223> OTHER INFORMATION: primer

<400> SEQUENCE: 156
tgtgaccagg agtcgcgaaa gtatattta					29

<210> SEQ ID NO 157
<211> LENGTH: 29
<212> TYPE: DNA
<213> ORGANISM: Artificial
<220> FEATURE:
<223> OTHER INFORMATION: primer

<400> SEQUENCE: 157
taaatatact ttcgcaactc ctggtcaca					29

<210> SEQ ID NO 158

```
<211> LENGTH: 29
<212> TYPE: DNA
<213> ORGANISM: Artificial
<220> FEATURE:
<223> OTHER INFORMATION: primer

<400> SEQUENCE: 158
tgtgaccagg agttgcgaaa gtatattta                              29

<210> SEQ ID NO 159
<211> LENGTH: 29
<212> TYPE: DNA
<213> ORGANISM: Artificial
<220> FEATURE:
<223> OTHER INFORMATION: primer

<400> SEQUENCE: 159
atctgatatt tccatgtcag tatctgaac                              29

<210> SEQ ID NO 160
<211> LENGTH: 29
<212> TYPE: DNA
<213> ORGANISM: Artificial
<220> FEATURE:
<223> OTHER INFORMATION: primer

<400> SEQUENCE: 160
gttcagatac tgacatggaa atatcagat                              29

<210> SEQ ID NO 161
<211> LENGTH: 29
<212> TYPE: DNA
<213> ORGANISM: Artificial
<220> FEATURE:
<223> OTHER INFORMATION: primer

<400> SEQUENCE: 161
tatttccatt tcagcctctg aactgggtt                              29

<210> SEQ ID NO 162
<211> LENGTH: 29
<212> TYPE: DNA
<213> ORGANISM: Artificial
<220> FEATURE:
<223> OTHER INFORMATION: primer

<400> SEQUENCE: 162
aacccagttc agaggctgaa atggaaata                              29

<210> SEQ ID NO 163
<211> LENGTH: 29
<212> TYPE: DNA
<213> ORGANISM: Artificial
<220> FEATURE:
<223> OTHER INFORMATION: primer

<400> SEQUENCE: 163
tatttccatt tcagcatctg aactgggtt                              29

<210> SEQ ID NO 164
<211> LENGTH: 29
<212> TYPE: DNA
<213> ORGANISM: Artificial
<220> FEATURE:
<223> OTHER INFORMATION: primer

<400> SEQUENCE: 164
```

```
aacccagttc agatgctgaa atggaaata                                             29

<210> SEQ ID NO 165
<211> LENGTH: 29
<212> TYPE: DNA
<213> ORGANISM: Artificial
<220> FEATURE:
<223> OTHER INFORMATION: primer

<400> SEQUENCE: 165
gacccacctg atgctaatga gcgatgtta                                              29

<210> SEQ ID NO 166
<211> LENGTH: 29
<212> TYPE: DNA
<213> ORGANISM: Artificial
<220> FEATURE:
<223> OTHER INFORMATION: primer

<400> SEQUENCE: 166
taacatcgct cattagcatc aggtgggtc                                              29

<210> SEQ ID NO 167
<211> LENGTH: 29
<212> TYPE: DNA
<213> ORGANISM: Artificial
<220> FEATURE:
<223> OTHER INFORMATION: primer

<400> SEQUENCE: 167
tacgccaatc tattatcgcc cgacccgta                                              29

<210> SEQ ID NO 168
<211> LENGTH: 29
<212> TYPE: DNA
<213> ORGANISM: Artificial
<220> FEATURE:
<223> OTHER INFORMATION: primer

<400> SEQUENCE: 168
tacgggtcgg gcgataatag attggcgta                                              29

<210> SEQ ID NO 169
<211> LENGTH: 29
<212> TYPE: DNA
<213> ORGANISM: Artificial
<220> FEATURE:
<223> OTHER INFORMATION: primer

<400> SEQUENCE: 169
caacggttct attttccgtg cgatcaaat                                              29

<210> SEQ ID NO 170
<211> LENGTH: 29
<212> TYPE: DNA
<213> ORGANISM: Artificial
<220> FEATURE:
<223> OTHER INFORMATION: primer

<400> SEQUENCE: 170
atttgatcgc acggaaaata gaaccgttg                                              29

<210> SEQ ID NO 171
<211> LENGTH: 29
<212> TYPE: DNA
```

-continued

```
<213> ORGANISM: Artificial
<220> FEATURE:
<223> OTHER INFORMATION: primer

<400> SEQUENCE: 171
tctgagaacg gaatacgatg gctggttct                                29

<210> SEQ ID NO 172
<211> LENGTH: 29
<212> TYPE: DNA
<213> ORGANISM: Artificial
<220> FEATURE:
<223> OTHER INFORMATION: primer

<400> SEQUENCE: 172
agaaccagcc atcgtattcc gttctcaga                                29

<210> SEQ ID NO 173
<211> LENGTH: 29
<212> TYPE: DNA
<213> ORGANISM: Artificial
<220> FEATURE:
<223> OTHER INFORMATION: primer

<400> SEQUENCE: 173
tctgagaacg gaacaagatg gctggttct                                29

<210> SEQ ID NO 174
<211> LENGTH: 29
<212> TYPE: DNA
<213> ORGANISM: Artificial
<220> FEATURE:
<223> OTHER INFORMATION: primer

<400> SEQUENCE: 174
agaaccagcc atcttgttcc gttctcaga                                29

<210> SEQ ID NO 175
<211> LENGTH: 29
<212> TYPE: DNA
<213> ORGANISM: Artificial
<220> FEATURE:
<223> OTHER INFORMATION: primer

<400> SEQUENCE: 175
gccggatcat atcattacga ctgaatgct                                29

<210> SEQ ID NO 176
<211> LENGTH: 29
<212> TYPE: DNA
<213> ORGANISM: Artificial
<220> FEATURE:
<223> OTHER INFORMATION: primer

<400> SEQUENCE: 176
agcattcagt cgtaatgata tgatccggc                                29

<210> SEQ ID NO 177
<211> LENGTH: 29
<212> TYPE: DNA
<213> ORGANISM: Artificial
<220> FEATURE:
<223> OTHER INFORMATION: primer

<400> SEQUENCE: 177
gccggatcat atcaatacga ctgaatgct                                29
```

<210> SEQ ID NO 178
<211> LENGTH: 29
<212> TYPE: DNA
<213> ORGANISM: Artificial
<220> FEATURE:
<223> OTHER INFORMATION: primer

<400> SEQUENCE: 178
agcattcagt cgtattgata tgatccggc                                29

<210> SEQ ID NO 179
<211> LENGTH: 29
<212> TYPE: DNA
<213> ORGANISM: Artificial
<220> FEATURE:
<223> OTHER INFORMATION: primer

<400> SEQUENCE: 179
gccggatcat atctgtacga ctgaatgct                                29

<210> SEQ ID NO 180
<211> LENGTH: 29
<212> TYPE: DNA
<213> ORGANISM: Artificial
<220> FEATURE:
<223> OTHER INFORMATION: primer

<400> SEQUENCE: 180
agcattcagt cgtacagata tgatccggc                                29

<210> SEQ ID NO 181
<211> LENGTH: 29
<212> TYPE: DNA
<213> ORGANISM: Artificial
<220> FEATURE:
<223> OTHER INFORMATION: primer

<400> SEQUENCE: 181
gccggatcat atccagacga ctgaatgct                                29

<210> SEQ ID NO 182
<211> LENGTH: 29
<212> TYPE: DNA
<213> ORGANISM: Artificial
<220> FEATURE:
<223> OTHER INFORMATION: primer

<400> SEQUENCE: 182
agcattcagt cgtctggata tgatccggc                                29

<210> SEQ ID NO 183
<211> LENGTH: 29
<212> TYPE: DNA
<213> ORGANISM: Artificial
<220> FEATURE:
<223> OTHER INFORMATION: primer

<400> SEQUENCE: 183
gccggatcat atccccacga ctgaatgct                                29

<210> SEQ ID NO 184
<211> LENGTH: 29
<212> TYPE: DNA
<213> ORGANISM: Artificial
<220> FEATURE:

<223> OTHER INFORMATION: primer

<400> SEQUENCE: 184
agcattcagt cgtggggata tgatccggc                                    29

<210> SEQ ID NO 185
<211> LENGTH: 29
<212> TYPE: DNA
<213> ORGANISM: Artificial
<220> FEATURE:
<223> OTHER INFORMATION: primer

<400> SEQUENCE: 185
gccggatcat atccctacga ctgaatgct                                    29

<210> SEQ ID NO 186
<211> LENGTH: 29
<212> TYPE: DNA
<213> ORGANISM: Artificial
<220> FEATURE:
<223> OTHER INFORMATION: primer

<400> SEQUENCE: 186
agcattcagt cgtagggata tgatccggc                                    29

<210> SEQ ID NO 187
<211> LENGTH: 29
<212> TYPE: DNA
<213> ORGANISM: Artificial
<220> FEATURE:
<223> OTHER INFORMATION: primer

<400> SEQUENCE: 187
gccggatcat atcccgacga ctgaatgct                                    29

<210> SEQ ID NO 188
<211> LENGTH: 29
<212> TYPE: DNA
<213> ORGANISM: Artificial
<220> FEATURE:
<223> OTHER INFORMATION: primer

<400> SEQUENCE: 188
agcattcagt cgtcgggata tgatccggc                                    29

<210> SEQ ID NO 189
<211> LENGTH: 29
<212> TYPE: DNA
<213> ORGANISM: Artificial
<220> FEATURE:
<223> OTHER INFORMATION: primer

<400> SEQUENCE: 189
gccggatcat atctcaacga ctgaatgct                                    29

<210> SEQ ID NO 190
<211> LENGTH: 29
<212> TYPE: DNA
<213> ORGANISM: Artificial
<220> FEATURE:
<223> OTHER INFORMATION: primer

<400> SEQUENCE: 190
agcattcagt cgttgagata tgatccggc                                    29

```
<210> SEQ ID NO 191
<211> LENGTH: 29
<212> TYPE: DNA
<213> ORGANISM: Artificial
<220> FEATURE:
<223> OTHER INFORMATION: primer

<400> SEQUENCE: 191
gctgcgttct gactatacct ggcacggct                              29

<210> SEQ ID NO 192
<211> LENGTH: 29
<212> TYPE: DNA
<213> ORGANISM: Artificial
<220> FEATURE:
<223> OTHER INFORMATION: primer

<400> SEQUENCE: 192
agccgtgcca ggtatagtca gaacgcagc                              29

<210> SEQ ID NO 193
<211> LENGTH: 29
<212> TYPE: DNA
<213> ORGANISM: Artificial
<220> FEATURE:
<223> OTHER INFORMATION: primer

<400> SEQUENCE: 193
cggcaccatg agcccatttg gtattccgg                              29

<210> SEQ ID NO 194
<211> LENGTH: 29
<212> TYPE: DNA
<213> ORGANISM: Artificial
<220> FEATURE:
<223> OTHER INFORMATION: primer

<400> SEQUENCE: 194
ccggaatacc aaatgggctc atggtgccg                              29

<210> SEQ ID NO 195
<211> LENGTH: 29
<212> TYPE: DNA
<213> ORGANISM: Artificial
<220> FEATURE:
<223> OTHER INFORMATION: primer

<400> SEQUENCE: 195
cgaacatggc atcttagttg agaaaaccg                              29

<210> SEQ ID NO 196
<211> LENGTH: 29
<212> TYPE: DNA
<213> ORGANISM: Artificial
<220> FEATURE:
<223> OTHER INFORMATION: primer

<400> SEQUENCE: 196
cggttttctc aactaagatg ccatgttcg                              29

<210> SEQ ID NO 197
<211> LENGTH: 29
<212> TYPE: DNA
<213> ORGANISM: Artificial
<220> FEATURE:
<223> OTHER INFORMATION: primer
```

<400> SEQUENCE: 197
cgaacatggc atcctggttg agaaaaccg                                29

<210> SEQ ID NO 198
<211> LENGTH: 29
<212> TYPE: DNA
<213> ORGANISM: Artificial
<220> FEATURE:
<223> OTHER INFORMATION: primer

<400> SEQUENCE: 198
cggttttctc aaccaggatg ccatgttcg                                29

<210> SEQ ID NO 199
<211> LENGTH: 29
<212> TYPE: DNA
<213> ORGANISM: Artificial
<220> FEATURE:
<223> OTHER INFORMATION: primer

<400> SEQUENCE: 199
gttcctgttc agctgcggta tcgataaga                                29

<210> SEQ ID NO 200
<211> LENGTH: 29
<212> TYPE: DNA
<213> ORGANISM: Artificial
<220> FEATURE:
<223> OTHER INFORMATION: primer

<400> SEQUENCE: 200
tcttatcgat accgcagctg aacaggaac                                29

<210> SEQ ID NO 201
<211> LENGTH: 29
<212> TYPE: DNA
<213> ORGANISM: Artificial
<220> FEATURE:
<223> OTHER INFORMATION: primer

<400> SEQUENCE: 201
gttcctgttc agccttggta tcgataaga                                29

<210> SEQ ID NO 202
<211> LENGTH: 29
<212> TYPE: DNA
<213> ORGANISM: Artificial
<220> FEATURE:
<223> OTHER INFORMATION: primer

<400> SEQUENCE: 202
tcttatcgat accaaggctg aacaggaac                                29

<210> SEQ ID NO 203
<211> LENGTH: 29
<212> TYPE: DNA
<213> ORGANISM: Artificial
<220> FEATURE:
<223> OTHER INFORMATION: primer

<400> SEQUENCE: 203
gttcctgttc agcctaggta tcgataaga                                29

<210> SEQ ID NO 204
<211> LENGTH: 29

```
<212> TYPE: DNA
<213> ORGANISM: Artificial
<220> FEATURE:
<223> OTHER INFORMATION: priemr

<400> SEQUENCE: 204
tcttatcgat acctaggctg aacaggaac                                  29

<210> SEQ ID NO 205
<211> LENGTH: 29
<212> TYPE: DNA
<213> ORGANISM: Artificial
<220> FEATURE:
<223> OTHER INFORMATION: primer

<400> SEQUENCE: 205
cggtatcgat aaggcgaaag cactgagcc                                  29

<210> SEQ ID NO 206
<211> LENGTH: 29
<212> TYPE: DNA
<213> ORGANISM: Artificial
<220> FEATURE:
<223> OTHER INFORMATION: primer

<400> SEQUENCE: 206
ggctcagtgc tttcgcctta tcgataccg                                  29

<210> SEQ ID NO 207
<211> LENGTH: 29
<212> TYPE: DNA
<213> ORGANISM: Artificial
<220> FEATURE:
<223> OTHER INFORMATION: primer

<400> SEQUENCE: 207
cggtatcgat aaggctaaag cactgagcc                                  29

<210> SEQ ID NO 208
<211> LENGTH: 29
<212> TYPE: DNA
<213> ORGANISM: Artificial
<220> FEATURE:
<223> OTHER INFORMATION: primer

<400> SEQUENCE: 208
ggctcagtgc tttagcctta tcgataccg                                  29

<210> SEQ ID NO 209
<211> LENGTH: 29
<212> TYPE: DNA
<213> ORGANISM: Artificial
<220> FEATURE:
<223> OTHER INFORMATION: primer

<400> SEQUENCE: 209
cggtatcgat aagtctaaag cactgagcc                                  29

<210> SEQ ID NO 210
<211> LENGTH: 29
<212> TYPE: DNA
<213> ORGANISM: Artificial
<220> FEATURE:
<223> OTHER INFORMATION: primer

<400> SEQUENCE: 210
```

```
ggctcagtgc tttagactta tcgataccg                                    29
```

<210> SEQ ID NO 211
<211> LENGTH: 29
<212> TYPE: DNA
<213> ORGANISM: Artificial
<220> FEATURE:
<223> OTHER INFORMATION: primer

<400> SEQUENCE: 211

```
cggtatcgat aagtccaaag cactgagcc                                    29
```

<210> SEQ ID NO 212
<211> LENGTH: 29
<212> TYPE: DNA
<213> ORGANISM: Artificial
<220> FEATURE:
<223> OTHER INFORMATION: primer

<400> SEQUENCE: 212

```
ggctcagtgc tttggactta tcgataccg                                    29
```

<210> SEQ ID NO 213
<211> LENGTH: 29
<212> TYPE: DNA
<213> ORGANISM: Artificial
<220> FEATURE:
<223> OTHER INFORMATION: primer

<400> SEQUENCE: 213

```
cggtatcgat aagcctaaag cactgagcc                                    29
```

<210> SEQ ID NO 214
<211> LENGTH: 29
<212> TYPE: DNA
<213> ORGANISM: Artificial
<220> FEATURE:
<223> OTHER INFORMATION: primer

<400> SEQUENCE: 214

```
ggctcagtgc tttaggctta tcgataccg                                    29
```

<210> SEQ ID NO 215
<211> LENGTH: 29
<212> TYPE: DNA
<213> ORGANISM: Artificial
<220> FEATURE:
<223> OTHER INFORMATION: primer

<400> SEQUENCE: 215

```
cggtatcgat aagccgaaag cactgagcc                                    29
```

<210> SEQ ID NO 216
<211> LENGTH: 29
<212> TYPE: DNA
<213> ORGANISM: Artificial
<220> FEATURE:
<223> OTHER INFORMATION: primer

<400> SEQUENCE: 216

```
ggctcagtgc tttcggctta tcgataccg                                    29
```

<210> SEQ ID NO 217
<211> LENGTH: 29
<212> TYPE: DNA
<213> ORGANISM: Artificial

```
<220> FEATURE:
<223> OTHER INFORMATION: primer

<400> SEQUENCE: 217
cgataagacc aaaagcctga gcctgctgc                                29

<210> SEQ ID NO 218
<211> LENGTH: 29
<212> TYPE: DNA
<213> ORGANISM: Artificial
<220> FEATURE:
<223> OTHER INFORMATION: primer

<400> SEQUENCE: 218
gcagcaggct caggcttttg gtcttatcg                                29

<210> SEQ ID NO 219
<211> LENGTH: 29
<212> TYPE: DNA
<213> ORGANISM: Artificial
<220> FEATURE:
<223> OTHER INFORMATION: primer

<400> SEQUENCE: 219
gactccgtat gcttgtttcc agaaagagc                                29

<210> SEQ ID NO 220
<211> LENGTH: 29
<212> TYPE: DNA
<213> ORGANISM: Artificial
<220> FEATURE:
<223> OTHER INFORMATION: primer

<400> SEQUENCE: 220
gctctttctg gaaacaagca tacggagtc                                29

<210> SEQ ID NO 221
<211> LENGTH: 29
<212> TYPE: DNA
<213> ORGANISM: Artificial
<220> FEATURE:
<223> OTHER INFORMATION: primer

<400> SEQUENCE: 221
gactccgtat gcttttttcc agaaagagc                                29

<210> SEQ ID NO 222
<211> LENGTH: 29
<212> TYPE: DNA
<213> ORGANISM: Artificial
<220> FEATURE:
<223> OTHER INFORMATION: primer

<400> SEQUENCE: 222
gctctttctg gaaaaaagca tacggagtc                                29

<210> SEQ ID NO 223
<211> LENGTH: 29
<212> TYPE: DNA
<213> ORGANISM: Artificial
<220> FEATURE:
<223> OTHER INFORMATION: primer

<400> SEQUENCE: 223
gactccgtat gctttcttcc agaaagagc                                29
```

<210> SEQ ID NO 224
<211> LENGTH: 29
<212> TYPE: DNA
<213> ORGANISM: Artificial
<220> FEATURE:
<223> OTHER INFORMATION: primer

<400> SEQUENCE: 224
gctctttctg gaagaaagca tacggagtc                                29

<210> SEQ ID NO 225
<211> LENGTH: 29
<212> TYPE: DNA
<213> ORGANISM: Artificial
<220> FEATURE:
<223> OTHER INFORMATION: primer

<400> SEQUENCE: 225
gactccgtat gctcagttcc agaaagagc                                29

<210> SEQ ID NO 226
<211> LENGTH: 29
<212> TYPE: DNA
<213> ORGANISM: Artificial
<220> FEATURE:
<223> OTHER INFORMATION: primer

<400> SEQUENCE: 226
gctctttctg gaactgagca tacggagtc                                29

<210> SEQ ID NO 227
<211> LENGTH: 29
<212> TYPE: DNA
<213> ORGANISM: Artificial
<220> FEATURE:
<223> OTHER INFORMATION: primer

<400> SEQUENCE: 227
tgctgcattc caggtggagc tgcacggta                                29

<210> SEQ ID NO 228
<211> LENGTH: 29
<212> TYPE: DNA
<213> ORGANISM: Artificial
<220> FEATURE:
<223> OTHER INFORMATION: primer

<400> SEQUENCE: 228
taccgtgcag ctccacctgg aatgcagca                                29

<210> SEQ ID NO 229
<211> LENGTH: 29
<212> TYPE: DNA
<213> ORGANISM: Artificial
<220> FEATURE:
<223> OTHER INFORMATION: primer

<400> SEQUENCE: 229
gaccgaagaa gtttgtctcg acgaaatgg                                29

<210> SEQ ID NO 230
<211> LENGTH: 29
<212> TYPE: DNA
<213> ORGANISM: Artificial
<220> FEATURE:
<223> OTHER INFORMATION: primer

```
<400> SEQUENCE: 230
ccatttcgtc gagacaaact tcttcggtc                                              29

<210> SEQ ID NO 231
<211> LENGTH: 29
<212> TYPE: DNA
<213> ORGANISM: Artificial
<220> FEATURE:
<223> OTHER INFORMATION: primer

<400> SEQUENCE: 231
gaccgaagaa gttcccctcg acgaaatgg                                              29

<210> SEQ ID NO 232
<211> LENGTH: 29
<212> TYPE: DNA
<213> ORGANISM: Artificial
<220> FEATURE:
<223> OTHER INFORMATION: primer

<400> SEQUENCE: 232
ccatttcgtc gagggaact tcttcggtc                                               29

<210> SEQ ID NO 233
<211> LENGTH: 29
<212> TYPE: DNA
<213> ORGANISM: Artificial
<220> FEATURE:
<223> OTHER INFORMATION: primer

<400> SEQUENCE: 233
aggtcgtatt aacttgaata tgatccttc                                              29

<210> SEQ ID NO 234
<211> LENGTH: 29
<212> TYPE: DNA
<213> ORGANISM: Artificial
<220> FEATURE:
<223> OTHER INFORMATION: primer

<400> SEQUENCE: 234
gaaggatcat attcaagtta atacgacct                                              29

<210> SEQ ID NO 235
<211> LENGTH: 29
<212> TYPE: DNA
<213> ORGANISM: Artificial
<220> FEATURE:
<223> OTHER INFORMATION: primer

<400> SEQUENCE: 235
aggtcgtatt aacatcaata tgatccttc                                              29

<210> SEQ ID NO 236
<211> LENGTH: 29
<212> TYPE: DNA
<213> ORGANISM: Artificial
<220> FEATURE:
<223> OTHER INFORMATION: primer

<400> SEQUENCE: 236
gaaggatcat attgatgtta atacgacct                                              29

<210> SEQ ID NO 237
```

```
<211> LENGTH: 29
<212> TYPE: DNA
<213> ORGANISM: Artificial
<220> FEATURE:
<223> OTHER INFORMATION: primer

<400> SEQUENCE: 237
tattaacgcc aattctatcc ttccgtacc                                    29

<210> SEQ ID NO 238
<211> LENGTH: 29
<212> TYPE: DNA
<213> ORGANISM: Artificial
<220> FEATURE:
<223> OTHER INFORMATION: primer

<400> SEQUENCE: 238
ggtacggaag gatagaattg gcgttaata                                    29

<210> SEQ ID NO 239
<211> LENGTH: 29
<212> TYPE: DNA
<213> ORGANISM: Artificial
<220> FEATURE:
<223> OTHER INFORMATION: primer

<400> SEQUENCE: 239
tattaacgcc aattccatcc ttccgtacc                                    29

<210> SEQ ID NO 240
<211> LENGTH: 29
<212> TYPE: DNA
<213> ORGANISM: Artificial
<220> FEATURE:
<223> OTHER INFORMATION: primer

<400> SEQUENCE: 240
ggtacggaag gatggaattg gcgttaata                                    29
```